United States Patent
Prakash et al.

(10) Patent No.: US 8,942,928 B2
(45) Date of Patent: Jan. 27, 2015

(54) ULTRASONIC METHOD OF MONITORING PARTICLE SIZE DISTRIBUTION OF A MEDIUM

(75) Inventors: Anand Prakash, London (CA); Abhishek Shukla, London (CA); Sohrab Rohani, London (CA)

(73) Assignee: The University of Western Ontario, London, ON (CA)

( * ) Notice: Subject to any disclaimer, the term of this patent is extended or adjusted under 35 U.S.C. 154(b) by 552 days.

(21) Appl. No.: 13/319,990

(22) PCT Filed: Jan. 18, 2010

(86) PCT No.: PCT/CA2010/000071
§ 371 (c)(1),
(2), (4) Date: Jan. 23, 2012

(87) PCT Pub. No.: WO2010/130024
PCT Pub. Date: Nov. 18, 2010

(65) Prior Publication Data
US 2012/0111117 A1   May 10, 2012

Related U.S. Application Data

(60) Provisional application No. 61/177,029, filed on May 11, 2009.

(51) Int. Cl.
| | | |
|---|---|---|
| G01N 15/02 | (2006.01) | |
| G01N 29/11 | (2006.01) | |
| G06F 19/00 | (2011.01) | |
| G01N 29/032 | (2006.01) | |
| G01N 29/44 | (2006.01) | |

(52) U.S. Cl.
CPC .......... *G01N 29/032* (2013.01); *G01N 29/4418* (2013.01); *G01N 29/4472* (2013.01); *G01N 2291/02416* (2013.01); *G01N 2291/0289* (2013.01)

USPC .......... 702/29; 73/61.41; 73/61.75; 73/64.53; 702/22

(58) Field of Classification Search
CPC .................. G01N 2291/02416; G01N 29/032; G01N 15/02; G01N 2291/015; G01N 2291/02809; G01N 2291/02836; G01N 29/221; G01N 29/46; G01N 2291/0289; G01N 29/4418; G01N 29/4472; G01S 15/885
USPC .......... 702/22, 29; 73/61.41, 61.75, 596, 599, 73/865.5, 64.63
See application file for complete search history.

(56) References Cited

U.S. PATENT DOCUMENTS

| | | |
|---|---|---|
| 5,121,629 A | 6/1992 | Alba |
| 6,119,510 A | 9/2000 | Carasso et al. |

(Continued)

FOREIGN PATENT DOCUMENTS

WO   2007003058   1/2007

*Primary Examiner* — John H Le
(74) *Attorney, Agent, or Firm* — Hill & Schumacher; Lynn C. Schumacher; Stephen W. Leonard

(57) ABSTRACT

Methods and are provided for determining, monitoring or detecting particle size distribution of a medium. An example method includes comparing a measured ultrasound attenuation spectrum of the medium with a calculated attenuation spectrum, where the calculated attenuation spectrum is obtained by accounting for the scattering of ultrasound waves into the receiver. The methods of the present invention can be used to determine particle size distribution in a dense suspension of particles in the intermediate wavelength regime. In other aspects, methods of the present invention may also be used to monitor changes in particle size distribution, infer the shape of particles, provide feedback to a process involving a change in particle size, and determine the completion of a dissolution process.

32 Claims, 49 Drawing Sheets

(56) References Cited

U.S. PATENT DOCUMENTS

| | | | |
|---|---|---|---|
| 6,748,815 B2 * | 6/2004 | Povey et al. | 73/865.5 |
| 7,010,979 B2 * | 3/2006 | Scott | 73/596 |
| 7,260,482 B2 | 8/2007 | Volker et al. | |
| 8,364,421 B2 * | 1/2013 | Chen et al. | 702/25 |
| 2005/0262927 A1 | 12/2005 | Scott | |
| 2006/0211128 A1 | 9/2006 | Johnson et al. | |

* cited by examiner

ULTRASONIC METHOD OF MONITORING PARTICLE SIZE DISTRIBUTION OF A MEDIUM

CROSS-REFERENCE TO RELATED APPLICATION

This application is a National Phase application claiming the benefit of PCT/CA2010/000071 filed on Jan. 18, 2010, in English, which further claims priority to U.S. Provisional Application No. 61/177,029, filed on May 11, 2009, the entire contents of which are incorporated herein by reference.

FIELD OF THE INVENTION

This invention relates to methods of monitoring particulate mixtures using ultrasonic attenuation measurements and simulations. More particularly, the invention relates to methods of monitoring particle size distributions and/or controlling processes based on an inferred particle size distribution. The invention also relates to methods of monitoring dissolution processes using ultrasonic attenuation.

BACKGROUND OF THE INVENTION

The monitoring of particle size distribution (PSD) in media such as suspensions is important in many industrial and diagnostic applications. Control or monitoring of operations such as crystallization, filtration, combustion, mineral processing, preparation of reaction feed streams, degree of reaction and the like, often depend on the ability to monitor and control the size of particles that are components of gas or liquid process streams.

Crystallizers are widely used in industrial processes for the production of chemicals, food products and pharmaceuticals. Crystallization processes are dynamic in nature and variations in crystal (particle) content and size are expected in real-time. Monitoring of these changes in particle content and size is essential to obtain/maintain desirable operating conditions, avoid complications in down stream processing and ensure product quality/conformity.

A number of methods of monitoring PSD are known in the art. The most widely accepted standard for PSD measurements is based on laser diffraction which, however, is restricted to diluted suspensions. A prior art laser-based method capable of operating in dense suspensions is the Focused Beam Reflectance Method (FBRM). However, this method measures the chord length distribution and not the particle size distribution. This method is also prone to errors caused by particle shadowing (due to fine particles), particle masking (due to coarse particles), and assumes that the entire particle projection area has perfect back reflectance. Furthermore, measurement samples are localized and not representative of the bulk and medium transparency is essential.

Ultrasonic attenuation spectroscopy has widely been accepted as one of the most promising techniques for measuring PSD in dense and opaque suspensions. However, its applicability for online measurement in dense suspensions generally has been restricted to smaller particles (colloids and emulsions) primarily due to the unavailability of a theoretical model for larger particle sizes.

A model for predicting PSD requires accurate measurement of an attenuation spectrum at different frequencies. Recent advances in hardware and measurements for ultrasound generation have provided the ability to accurately measure the attenuation spectrum over a wide range of frequencies. The measured attenuation spectrum is then compared with the predictions of a theoretical model which requires the physical properties of the particles and suspension medium along with an assumed size distribution. A deconvolution algorithm optimizes the parameters of the assumed size distribution to minimize the error between the measured and predicted attenuation spectrum. However, the accuracy of the predicted PSD is limited by the accuracy of its theoretical model and the adequacy with which the deconvolution algorithm is able to simulate the actual conditions existing during the measurement of the attenuation spectrum.

In colloidal and emulsion systems the wavelength ($\lambda$) of the ultrasonic signal is much larger than the particle size ($\lambda \gg r$) and absorption losses are dominant. This regime of wave propagation is known as the long wave regime and predominates where the ratio of particle circumference and wavelength is less than $0.1^1$. This ratio is a non-dimensional quantity and is known as the wave number. Short wave regime of propagation exists when the wavelength is much smaller than the particle size ($\lambda \ll r$). The regime of wave propagation between these two extreme limits is known as the intermediate regime.

U.S. Pat. No. 5,121,629 discloses a method of determining size distribution and concentration of particles in suspension using ultrasonic attenuation. A measured attenuation spectrum is obtained at selected discrete frequencies over a selected frequency range and compared to calculated attenuation spectra to derive an approximate match between the calculated and measured spectra. The particle size distribution and concentration used to calculate the spectra are used to derive a new set values for the particle size distribution that corresponds to the measured attenuation spectrum.

U.S. Pat. No. 7,010,979 discloses a particle size distribution monitor in liquid using ultrasonic attenuation, means of generating and receiving the ultrasonic wave and attenuation spectrum, calculation using FFT for particles suspended in the liquid. This is followed by a means of determining an estimated PSD, and a means of determining the goodness of fit.

Current ultrasonic attenuation based instruments (OPUS™—Sympatec Inc., UltraPS—CSIRO) with the capability of online monitoring of PSD in dense suspensions of large particles (particles outside the long wave regime) are based on pre-measured attenuation coefficient spectrum of various particle size fractions. The deconvolution algorithm used by these products is highly iterative and can be unstable in the absence of any real theoretical relationship between attenuation coefficients, physical properties of the particles and size parameters. These instruments have to be extensively calibrated and customized for specific particulate systems, and the calibration process is specific for a given type and size range of particles.

Despite significant improvements in the methods and instruments available to measure PSD in media, there remain certain applications where such measurement is difficult. For example, in media with relatively larger particle size (intermediate wave propagation regime), in media that are optically opaque—such as crude oil—or where particle concentration is high, and where measurements are required on a rapid basis—even on a real-time basis—and without dilution of the fluid, conventional PSD systems are unsuitable. Accordingly, it would be useful to provide a method for measuring PSD in dense or optically opaque media in the intermediate wave propagation regime. It would also be useful to provide such a method that could provide such measurements on a rapid, or real-time basis and without extensive calibration. It would also be useful if such a method could perform these measurements without diluting the fluid in which the particles are carried.

SUMMARY OF THE INVENTION

The present invention relates to novel methods for determining, monitoring, and detecting particle size distribution in a medium. The methods of the present invention can be used to determine particle size distribution in a dense suspension operating in the intermediate regime of wave propagation. In aspects, the methods of the present invention may also be used to monitor changes in particle size distribution in a medium. In further aspects, the methods of the present invention are online methods for calculating particle size distribution in a medium.

Accordingly, in a first aspect of the invention, there is provided a method of determining a particle size distribution of particles within a sample medium, comprising the steps of:

providing an ultrasonic transmitter and receiver separated by a fixed path length for transmitting and receiving ultrasonic waves;

measuring an ultrasonic attenuation spectrum of the sample medium;

calculating a simulated attenuation spectrum obtained from a model comprising the calculation of a scattering cross-section, wherein the scattering cross-section accounts for ultrasonic waves scattered into the receiver;

varying parameters of the model to minimize an error between the simulated attenuation spectrum and the measured attenuation spectrum, thereby obtaining optimized parameters; and calculating the particle size distribution from the optimized parameters.

In another aspect of the invention, a frequency-dependent weight factor may be employed to provide improved signal-to-noise when determining a particle size distribution, where the weight factor is dependent on the relative transmitted power at a given frequency. According, this aspect provides a method of determining a particle size distribution of particles within a sample medium, comprising the steps of:

providing an ultrasonic transmitter and receiver separated by a fixed path length for transmitting and receiving ultrasonic waves;

measuring an ultrasonic attenuation spectrum of the sample medium;

calculating a simulated attenuation spectrum obtained from a model comprising the calculation of a scattering cross-section;

calculating a frequency-dependent weight factor, the weight factor obtained by determining, at each frequency interval within the measured attenuation spectrum, a value related to a ratio of the transmitted ultrasonic power within the frequency interval to the total transmitted ultrasonic power;

multiplying the measured attenuation spectrum and the calculated attenuation spectrum by the weight factor;

varying parameters of a model to minimize an error between the multiplied simulated attenuation spectrum and the multiplied measured attenuation spectrum, thereby obtaining optimized parameters; and calculating the particle size distribution from the optimized parameters.

In yet another embodiment of the invention, a method is provided of monitoring a process involving particle size variation in a sample medium, the method comprising the steps of:

a) providing an ultrasonic transmitter and receiver separated by a fixed path length for transmitting and receiving ultrasonic waves;

b) measuring an ultrasonic transmission spectrum of the sample medium;

c) determining a peak transmission frequency; and d) repeating steps b)-c) for monitoring the peak frequency over a time duration.

In another aspect of the invention, there is provided an integrated ultrasonic probe for measuring transmission of ultrasonic waves within a medium, the probe comprising an ultrasonic transmitter and an ultrasonic receiver separated by a connecting member defining a fixed transmission path length, the transmitted and receiver oriented along a common transmission axis, wherein the connecting member is positioned to allow uninterrupted transmission of ultrasonic waves between the transmitter and receiver along the transmission axis.

In an additional aspect of the invention, there is provided a system for measuring transmission of ultrasonic waves within a medium, the system comprising:

a probe comprising an ultrasonic transmitter and an ultrasonic receiver separated by a connecting member defining a fixed transmission path length, the transmitted and receiver oriented along a common transmission axis, wherein the connecting member is positioned to allow uninterrupted transmission of ultrasonic waves between the transmitter and receiver along the transmission axis;

an ultrasonic controller for providing power to the ultrasonic transmitter and detecting a signal from the ultrasonic receiver.

In another aspect of the invention, there is provided a method of determining the completion of a particle dissolution process in a medium sample, the method comprising the steps of:

a) providing an ultrasonic transmitter and receiver separated by a fixed path length for transmitting and receiving ultrasonic waves;

b) monitoring time-dependent transmission of an ultrasonic pulse through the sample;

c) calculating a time-dependent acoustic velocity, total attenuation, and attenuation spectrum for the sample medium; and d) inferring a completion of the dissolution process based a rate of change of the acoustic velocity, total attenuation, and attenuation spectrum.

A further understanding of the functional and advantageous aspects of the invention can be realized by reference to the following detailed description and drawings.

BRIEF DESCRIPTION OF THE DRAWINGS

The embodiments of the present invention are described with reference to the attached figures, wherein.

DETAILED DESCRIPTION OF THE INVENTION

Figure 1:
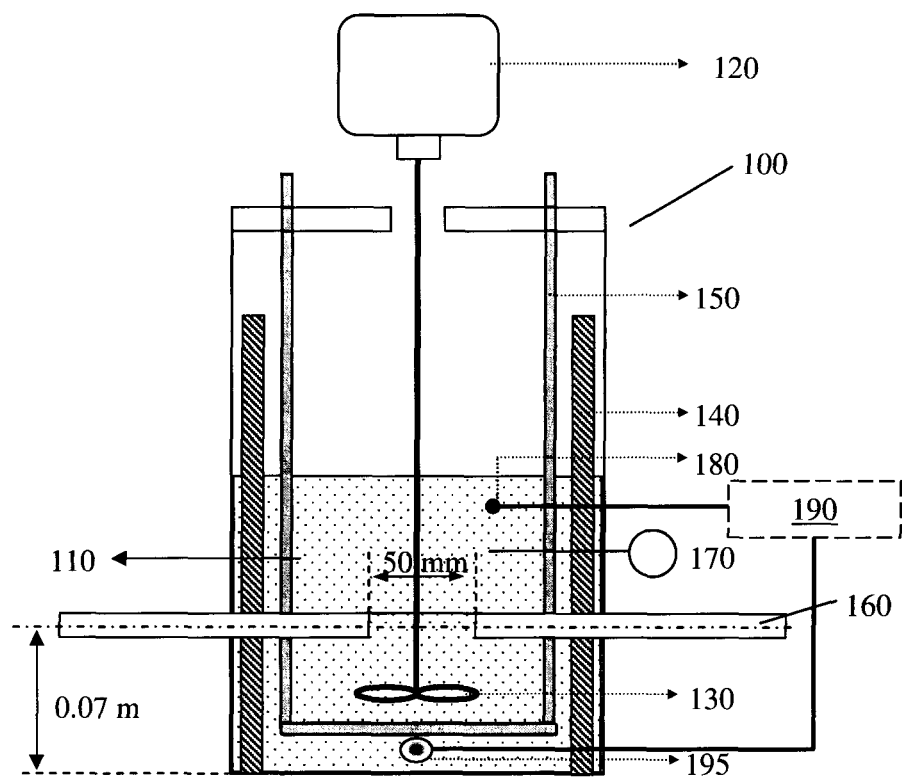
FIG. 1 shows a schematic diagram of a system according to one embodiment of the invention involving the use of ultrasonic measurements in a stirred tank.

Generally speaking, the systems described herein are directed to methods of monitoring the particle size distribution of a medium. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to methods of monitoring the particle size distribution of a medium involving crystallization and dissolution.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the terms "about" and "approximately, when used in conjunction with ranges of dimensions of particles, compositions of mixtures or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the coordinating conjunction "and/or" is meant to be a selection between a logical disjunction and a logical conjunction of the adjacent words, phrases, or clauses. Specifically, the phrase "X and/or Y" is meant to be interpreted as "one or both of X and Y" wherein X and Y are any word, phrase, or clause.

The present invention provides embodiments relating to the determination of the particle size distribution of a medium using ultrasound attenuation spectroscopy, and the application of such methods to process monitoring and control. Aspects of the invention are disclosed in the following sections. Section 1 introduces the experimental apparatus and methods referred (as non-limiting examples) in Sections 2 and 3. Section 2 motivates the need for a new and inventive method of determining the particle size distribution in the intermediate wave propagation regime. Section 3 discloses embodiments of the invention in which forward low-angle scattering into a finite sized detector is addressed. In section 4, an inventive approach of incorporating a weighing factor is disclosed, whereby signal components having high signal to noise ratios are emphasized in the calculation of a particle size distribution. Section 5 provides preferred embodiments for estimating the particle size distribution of a sample using the methods disclosed in Sections 3 and 4. Section 6 provides a specific an example in which an embodiment of the invention is applied to the online monitoring of a crystallization process. Section 7 discloses an improved ultrasonic transducer system for use in monitoring particle size distributions. In Section 8, additional embodiments of the invention related to process control are disclosed. Section 9 provides a glossary of mathematical symbols used in the specification.

SECTION 1

Experimental Apparatus and Methods Employed in Sections 2 and 3

In Sections 2 and 3, aspects of the invention are demonstrated using non-limiting experimental examples involving ultrasonic measurements of particle mixtures comprising glass beads. They should not be considered as a limitation on the scope of the invention, but merely as being illustrative and representative thereof. Those skilled in the art will readily appreciate that the specific methods disclosed herein may be applied to a wide variety of material systems within the scope of the present invention.

Attenuation measurements were made at different frequencies in liquid-solid suspension of glass beads in de-ionized (DI) water using Fallon Ultrasonic® pulser/receiver unit. The experiments were conducted in a stirred tank made of plexiglass with diameter 0.1 m and height 0.252 m.

A schematic representation of the system used according to embodiments of the invention is shown in FIG. 1. The tank 100 contains suspension 110 and includes a stirrer 120 having a 45° pitched blade impeller 130, baffles 140, and integrated cooling tubes 150 connected to a water bath. An ultrasonic transducer pair 160 is provided within the tank, consisting of a transmitted and receiver. Temperature is monitored with temperature probe 170, thermo regulator 180 and a temperature control unit 190, and a heater 195 is included for temperature control. The tank is also equipped with radial ports (not shown) for mounting the transducers.

The stirrer speed was maintained about 10% above the minimum speed required for good particle suspension.[1] The glass beads had a mean size of 43, 85, 114, 119, 156, 202-μm and the suspension concentration was varied from 2 to 20-vol. % with 2-vol. % increments. Measurements were also made in concentrated slurries of 119-μm glass beads in canola oil and 112-μm aluminum oxide in DI-water. Acoustic parameters were measured using the Fallon pulser/receiver unit in through transmission mode. The acoustic pulse was generated using broadband transducers and the instrument reported the peak amplitude of the pulse. The pulser/receiver unit activates the receiving transducer at a time fixed by the delay and for duration of the gate width to measure the flight time of the signal. The pulse repetition rate was 1 kHz and the sampling interval was 1 s. Hence, each sampled value of transit time and amplitude represent the average of 1000 acoustic pulses. Transducer separation used during this study was 50 mm and experiments were conducted using two sets of transducers with central frequencies of 3.4 and 1.2 MHz. This arrangement of transducers is intrusive in nature but was preferred to maximize signal strength. The transducers were enclosed in a cylindrical housing to minimize resistance to the flow of slurry. Small ratio of the particle size to the distance between transducers also reduced distortions to particles motion in the stirred tank. A TDS 210 (Tektronix) digital oscilloscope was used to visualize, select and capture the pulse.

SECTION 2

The Need for an Improved Method of Determining the Particle Size Distribution in the Intermediate Wave Propagation Regime In this section, a discussion is provided addressing the failure of prior art methods to achieve suitable particle size distribution determination in the intermediate wave propagation regime. The section begins with a discussion of ultrasound attenuation measurements and models, and then addresses the application of these models for particle size determination.

A transmission technique for measuring acoustic attenuation and velocity has evolved from the work of Pellam and Galt[2] and Pinkerton[3]. They used narrow band-width transducers in pulse-echo mode and variable path lengths to calculate the acoustic velocity and attenuation. Andrea and Joyce[4] modified this technique to incorporate through-transmission mode of operation and multiple frequency measurements using tone-burst signals. Multiple frequency measurements were further enhanced by the use of wide bandwidth video signals.[5] These signals consist of a range of frequencies as opposed to the finite cycle tone-bursts at different frequencies. The frequency component from wide bandwidth signals is extracted using Fast Fourier Transforms (FFT) and forms the basis of modern ultrasonic particle sizing technique.

Recent advances in the hardware required for ultrasound generation and measurement has provided the ability to accurately measure the attenuation spectra over a wide range of frequencies. However, the accuracy of particle size distributions (PSD) generated is limited by the adequacy of the underlying theoretical model. In general the model for acoustic particle sizing should meet the following criteria to enable its applicability in industrial processes:

1. Valid for large particle size range.
2. Valid for concentrated suspensions.

These criteria are achieved if the theoretical models account for the various attenuation mechanisms, preferably along with particle-particle interaction.

The attenuation mechanism and extent of attenuation in an inhomogeneous medium is dependent on the physical properties of the liquid and solid phases along with particle size, pulse frequency and particles concentration. Various models available in literature for prediction of attenuation include the work of Riebel6, McClements[7], Dukhin and Goetz[8], Epstein and Carhart[9] and Allegra and Hawley[10]. The different mechanisms of wave propagation have been discussed in detail by Dukhin and Goetz[8] and can be broadly categorized under absorption (viscous and thermal losses) and scattering losses. The extent of these losses is a function of the wave propagation regimes, which are defined using the non-dimensional wave number (kr). The wave number is the ratio of particle radius to pulse wavelength and can be calculated using Equation 1. Different wave propagation regimes identified based on this number is also shown in the equation given below.

$$kr = \frac{\omega}{c}r = \frac{2\pi f}{c}r = \frac{2\pi r}{\lambda} \quad (1)$$

$kr \ll 1; \quad \lambda \gg r \quad$ Long wave regime
$kr \sim 1; \quad \lambda \sim r \quad$ Intermediate wave regime
$kr \gg 1; \quad \lambda \ll r \quad$ Short wave regime There are two approaches to determine the total attenuation caused by various energy loss mechanisms. The traditional approach has been to develop a unified theory accounting for each of the loss mechanisms. The most widely used unified theory is the ECAH[9,10] model and accounts for the viscous, thermal and scattering losses. It is based on the superposition of single particle attenuation to obtain the total energy loss. This theory is limited to long wave regime of propagation, wherein the particles are much smaller than the wavelength. It also does not account for particle-particle interactions and hence is limited to dilute concentrations. The various modifications/extensions to increase the applicability of the ECAH theory include the work of McClements et al.[11], Watermann and Truell[12], Lloyd and Berry[13], Harker and Temple[14], Gibson and Toksoz[15] and Temkin[16]. However, these modifications are still unable to meet the two basic criteria required for a truly universal particle sizing technique. An alternative approach to determine total attenuation was suggested by Dukhin and Goetz[8]. This approach is based on the well known extinction theory proposed by Bohren and Huffman[17]. This theory was originally proposed for light but is also relevant for sound and states that the various energy losses are additive (Extinction=Absorption+Scattering). Hence, the various attenuation losses can be independently determined using individual theories for scattering ($\alpha_{sc}$), viscous ($\alpha_v$) and thermal ($\alpha_t$), loss mechanisms.

$$\alpha = \alpha_{sc} + \alpha_v + \alpha_t \quad (2)$$

However, Dukhin and Goetz[8] have concentrated their efforts to develop a rigorous model for viscous and thermal dissipation and only refer to simplified scattering model as their focus was on particle sizing in the colloidal and emulsion region (long wave regime).

As discussed in Section 2, aspects of the present invention involve experimentally measured attenuation in the intermediate wave propagation regime (kr) where both viscous and scattering losses are present. In this regime the viscous losses are dominant at lower wave numbers and scattering losses gain significance at higher wave numbers. However, neither of these losses is small enough to be completely neglected. The theoretical model used in preferred embodiments of the invention is adapted from the work of Morse and Ingard[18] and extended to account for multiple frequencies and polydispersity.

Prior to discussing the model of Morse and Ingard and its adaptation according to selected embodiments of the invention, the following discussion provides further insight into the need to improve methods in the intermediate wave propagation regime, by way of non-limiting experimental examples.

Figure 2:
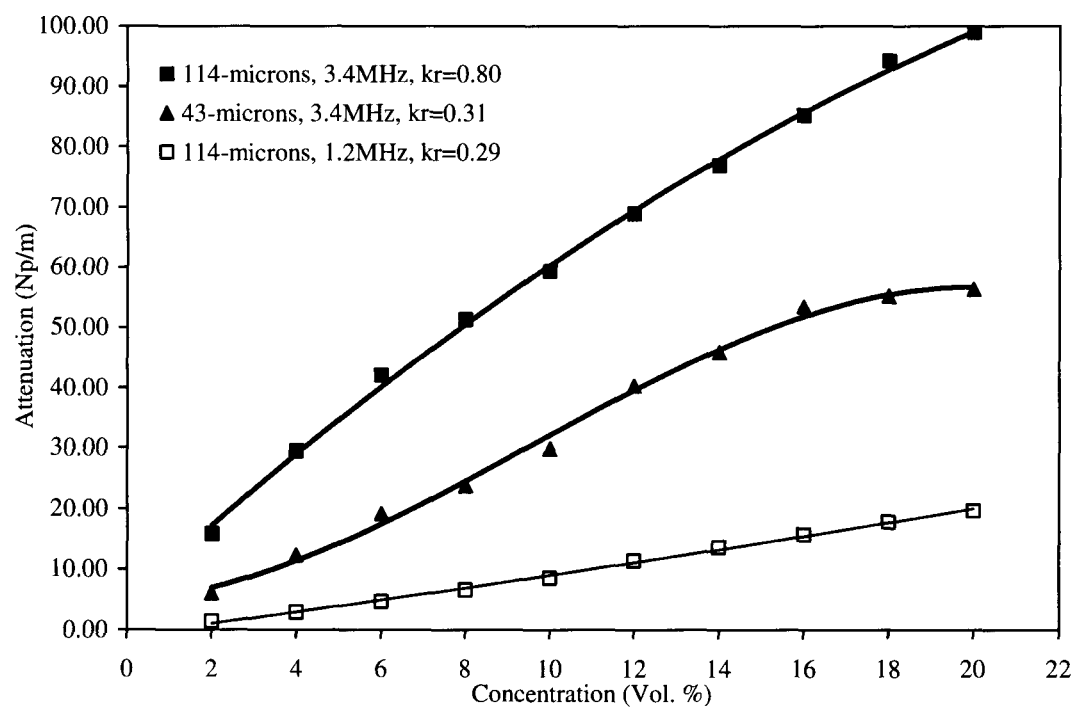
FIG. 2 plots the change in attenuation (Np/m) with concentration for 114 and 43-µm particles using 1.2 and 3.4 MHz transducers.

FIG. 2 shows the change in attenuation at peak frequency with concentration for 43 and 114-μm particles using 3.4 and 1.2 MHz transducers. Attenuation was calculated using Equation 3 and shows an increase with concentration for both particle sizes.

$$\alpha_m(\text{Np}/m) = \sum_{i=1}^{m} \frac{1}{x} \ln\left(\frac{A_{i-1}}{A_i}\right) \quad (3)$$

In the above equation $A_{i-1}$ and $A_i$ are the measured amplitudes before and after incremental solids addition respectively and x is the propagation distance. The total attenuation at a given solids concentration is the summation of incremental attenuations at the preceding concentrations. This procedure was developed to account for increase in gain which was increased at regular concentration intervals required to make up for the loss in signal strength due to attenuation. At a given concentration the maximum gain level is limited to avoid saturation of the signal.

FIG. 2 shows that the measured attenuation is higher for larger particles at 3.4 MHz frequency and is similar to results obtained in literature studies[19-21]. The wave numbers (kr) for the mean particle size at different central frequencies are also shown in FIG. 2. Experimental measurements show a significant difference in measured attenuation for similar kr values obtained using different particle sizes and frequencies. The kr values of 114 and 43 µm particles at 1.2 and 3.4 MHz frequency are 0.29 and 0.31 respectively. Similar attenuation was expected for these suspensions as the relative difference between their kr values is small and indicates the presence of a common wave propagation regime. Theoretical models suggested in literature show that the attenuation within a propagation regime are scaled according to the frequency[20,21]. Hence, the effect of measurement frequency on attenuation needs to be normalized for the comparison of these coefficients obtained at different frequencies. This can be achieved by calculating the attenuation per unit frequency as shown in Equation 4[7].

$$\alpha_M (Np/m/MHz) = \frac{1}{f} \sum_{i=1}^{m} \frac{1}{x} \ln\left(\frac{A_{i-1}}{A_i}\right) \quad (4)$$

Figure 3:
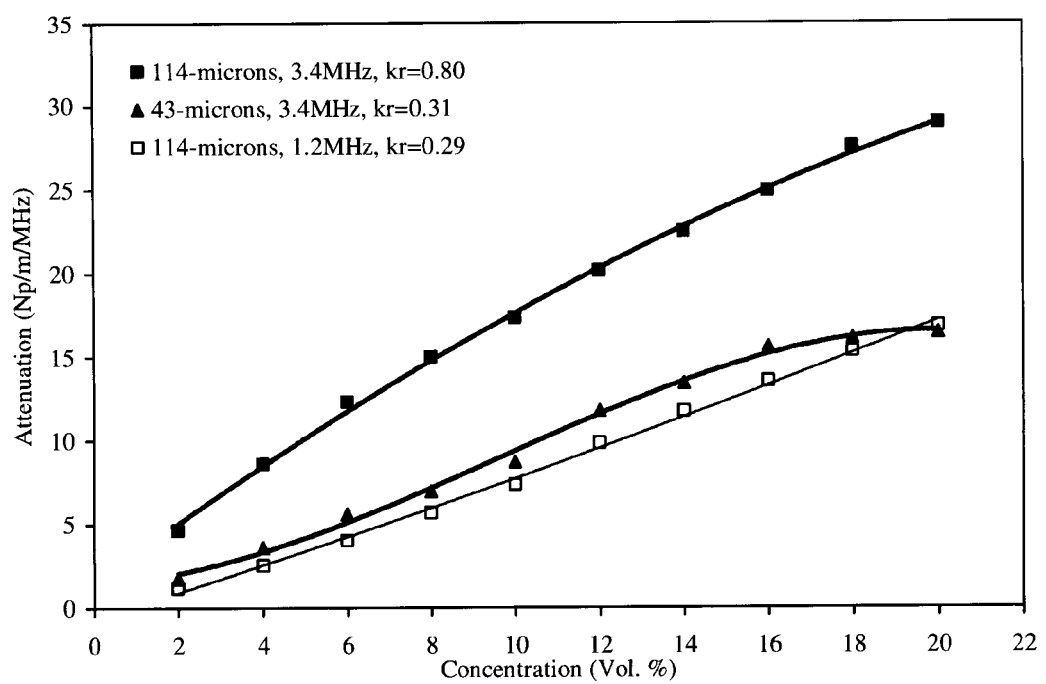
FIG. 3 plots the change in attenuation/central frequency (Np/m/MHz) with concentration for 114 and 43-µm particles using 1.2 and 3.4 MHz transducers.

FIG. 3 shows that attenuation per MHz of frequency for 43 and 114-µm particles are similar for similar kr values when they are scaled with respect to the frequency.

Figure 4:
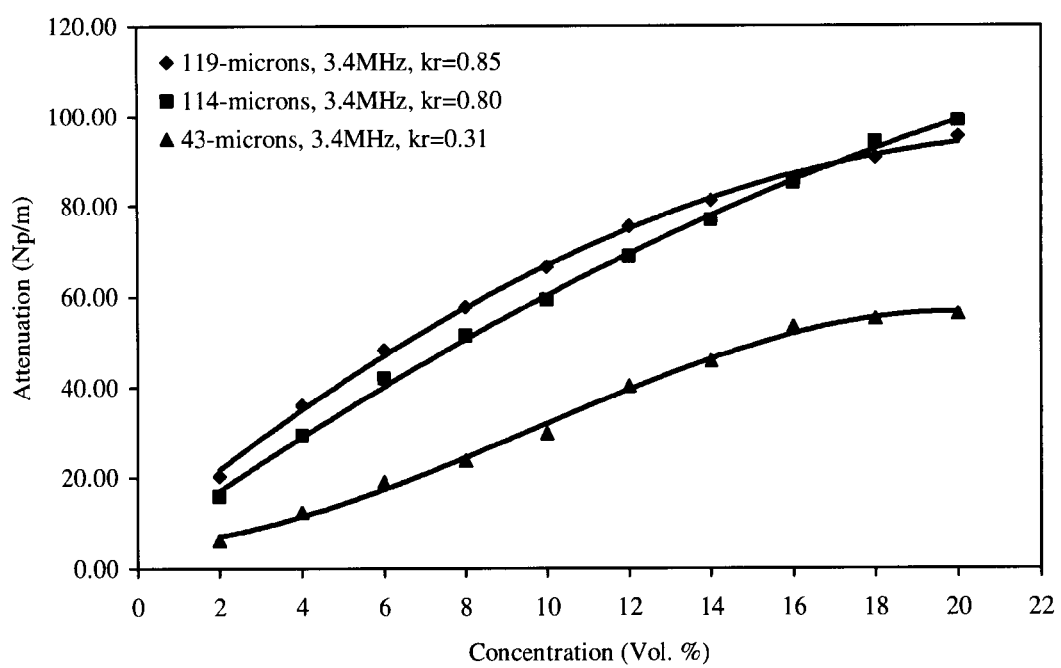
FIG. 4 shows a comparison of the change in attenuation (Np/m) with concentration for 43, 114 and 119-µm particles using 3.4 MHz transducer.
Figure 5:
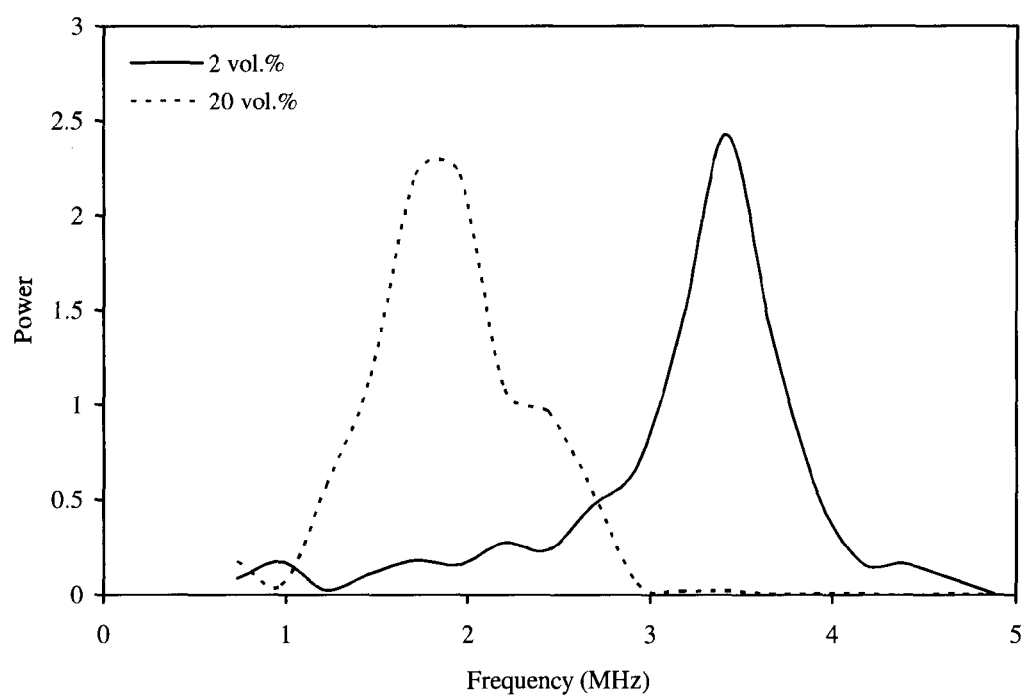
FIG. 5 plots the power spectrum of 119-μm particles using 3.4 MHz transducer.

FIG. 4 shows that change in attenuation in Np/m is linear with increase in concentration up to 6 vol. % for 119, 114-µm particles and up to 18 vol. % for 43-µm particles. Non-linearity of attenuation with increase in concentration can be attributed to particle-particle interactions at high concentration and is dependent on the dominant mechanism of attenuation[8]. It is shown by these authors that viscous attenuation is linear up to 14 vol. % concentrations and scattering attenuation is linear up to 40 vol. % concentrations. This indicates that the observed non-linearity of the attenuation with concentration for 114 and 119-µm particles cannot be due to particle-particle interactions. An alternative explanation for this observation can be attributed to the pulse bandwidth. FIG. 5 shows the acoustic pulse in the frequency domain at 2 and 20 vol. % for 119-µm particle suspension. Both the measured pulses are characterized by a peak frequency at which maximum attenuation occurs. However, the peak frequency location changes significantly with increase in concentration.

In the intermediate wave propagation regime, scattering attenuation increases with increase in the frequency of the acoustic pulse.[20,8] Hence, for a broadband acoustic pulse, energy at higher frequencies will dissipate at a faster rate as compared to lower frequencies and will eventually lead to total loss of power at higher frequencies. As a result of this the measured peak amplitude by the unit gradually shifts to lower frequencies. Since energy dissipation at lower frequencies is smaller, the attenuation appears to become less sensitive to concentration increase in dense suspensions. Furthermore, the change in peak frequency occurs after incremental solids addition. Hence, the peak powers '$P_i$' and '$P_{i-1}$' measured by the pulser/receiver unit are at different frequencies. This error can be avoided by using the FFT to obtain the attenuation measurements at the peak frequency of the received pulse (Equation 5).

$$\alpha_{f_{peak}} (Np/m/MHz) = \frac{1}{f_{peak}} \sum_{i=1}^{m} \frac{1}{2x} \ln\left(\frac{P_{i-1}}{P_i}\right) \quad (5)$$

Figure 6:
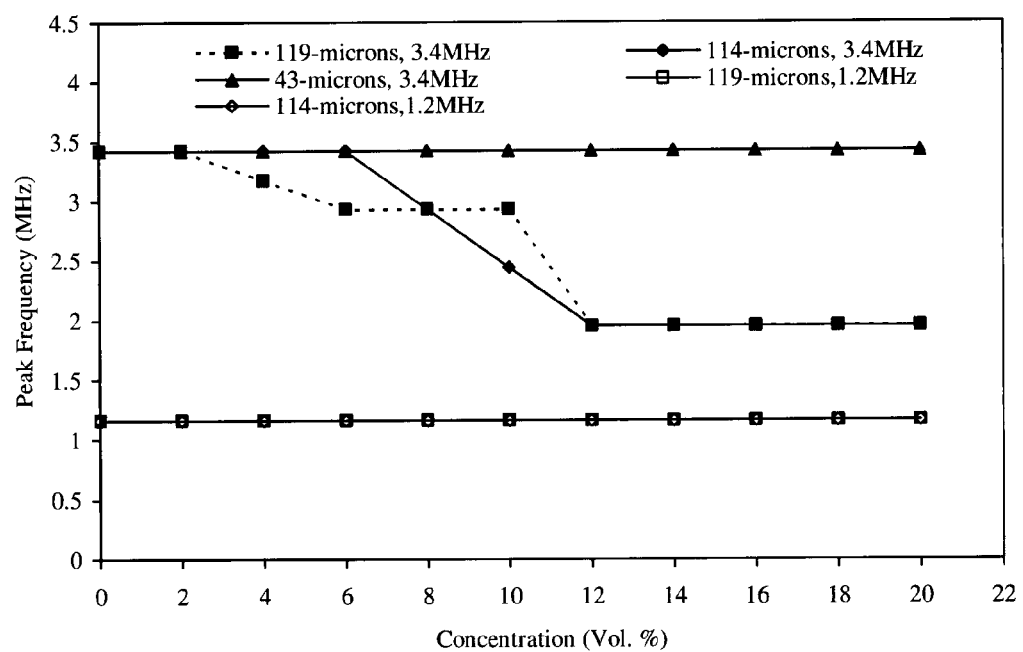
FIG. 6 plots the change in peak frequency with concentration for 43, 114 and 119-μm particles using 3.4 and 1.2 MHz frequency transducers.

The peak frequencies of the received pulse for different particle sizes obtained using FFT are shown in FIG. 6. The figure shows that the shift in peak frequency only occurs for particles predominantly in the intermediate wave propagation regime (average kr~0.8) where the scattering mechanism is dominant.

Figure 7:
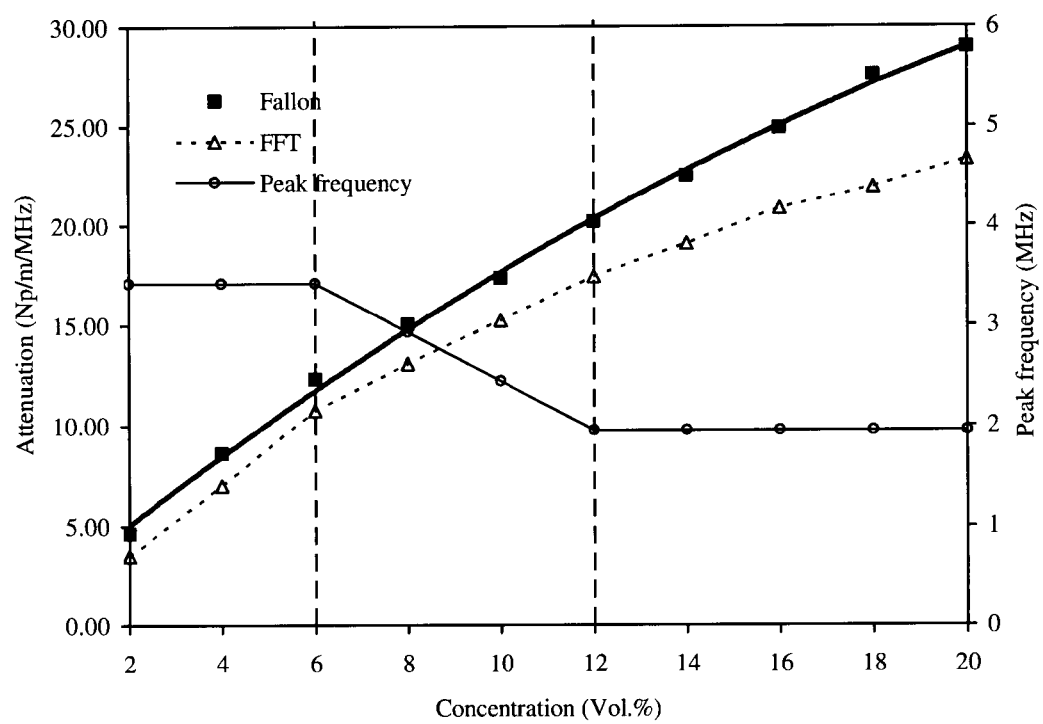
FIG. 7 provides a comparison of attenuation/peak frequency (114-μm at 3.4 MHz) calculated using measurements from the Fallon instrument and FFT along with the change in measured peak frequency.

FIG. 7 shows a comparison of the normalized attenuation at the peak frequency obtained using the pulser/receiver and FFT along with the peak frequency at different concentrations of 114-µm particles (3.4 MHz transducer). The calculated attenuations using the two techniques are similar till a change in the peak frequency after 6-vol. % occurs. Above this concentration higher attenuations are calculated from the amplitude measurements obtained using the Fallon instrument as measured amplitudes '$A_i$' and '$A_{i-1}$' are at different frequencies. The attenuation measurements obtained from the FFT is linear even at high concentrations provided the measurement frequency does not change.

Figure 8:
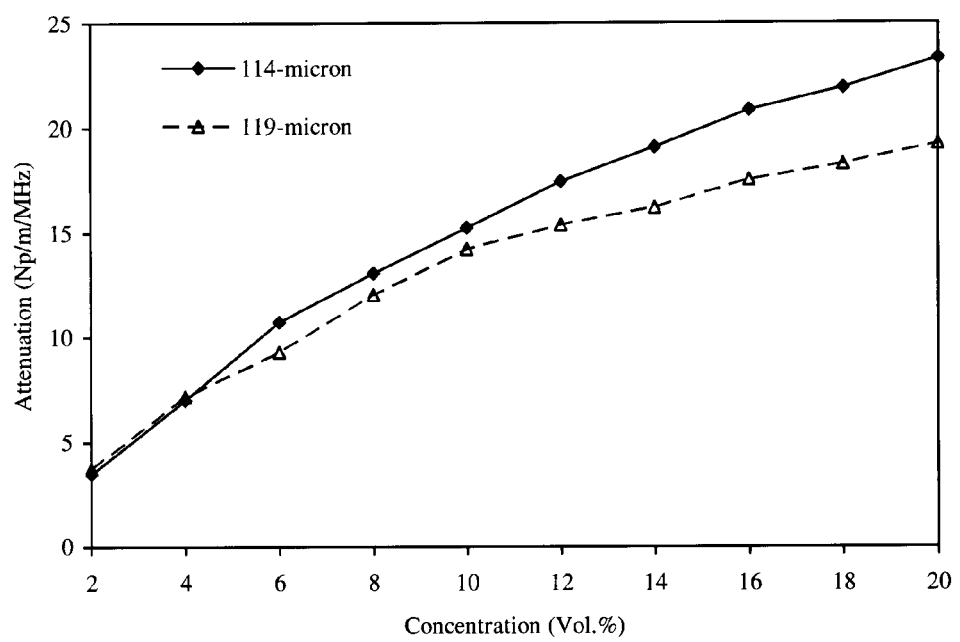
FIG. 8 plots a comparison of attenuation/peak frequency (FFT) for 114 and 119-μm particles using 3.4 MHz transducer.
Figure 9:
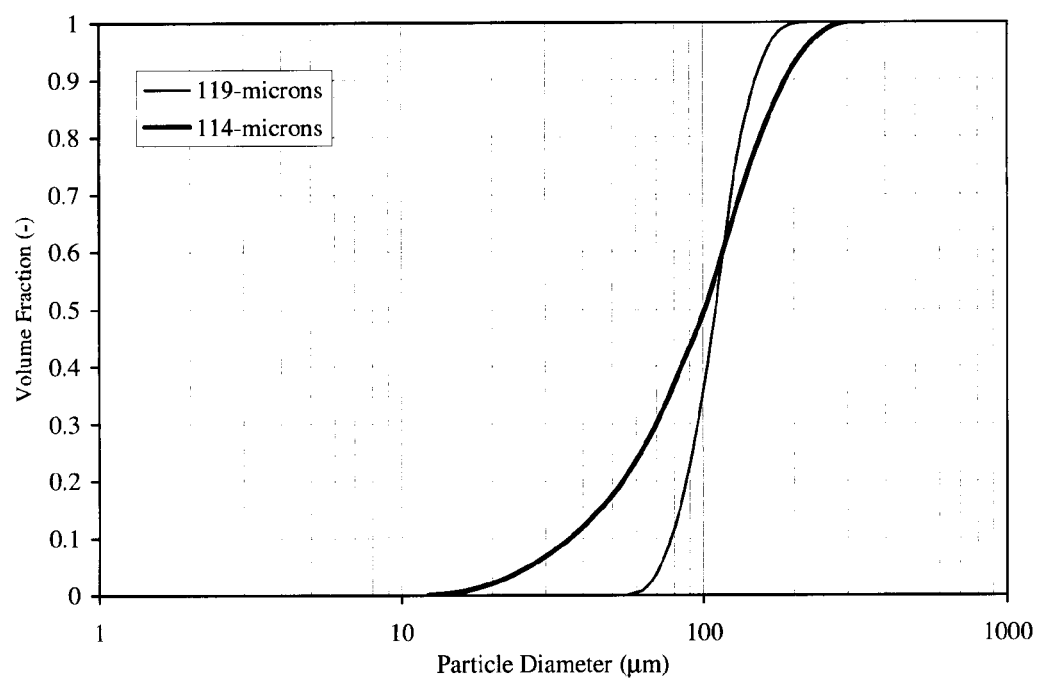
FIG. 9 plots the particle Size Distribution of 114 and 119-μm particles (according to the Malvern Mastersizer®).

An interesting observation was made from comparison of normalized attenuation at peak frequency obtained from FFT with 114 and 119-µm particles and 3.4 MHz transducers (FIG. 8). Significant difference between measured attenuation for these particles with similar mean size was observed above 4-vol. % concentration. At intermediate concentrations (4 to 12-vol. %) the observed deviation could be attributed to change in the peak frequency. However, the average change in peak frequency for both particles from 2 to 20-vol. % was similar and hence the measured attenuations at 20-vol. % should have been comparable. The observed difference in the attenuation measurements in FIG. 8 can be attributed to the nature of size distribution of the two particle samples. FIG. 9 shows the PSD obtained using the Malvern Mastersizer® of 114 and 119-µm particles. The size distribution of 114-µm particles is wide and ~25% of particles are smaller and ~10% of particles are larger than the minimum and maximum particle size in the 119-µm particle sample. The average kr values of the smaller and larger particle fractions in 114-µm samples at 3.4 MHz are 0.21 and 1.8, respectively. Since the kr values of larger particle fraction in 114-µm sample is ~2 times the average kr value of 119-µm particles, the extent of scattering will be higher. The resolution of attenuation measurements increases for concentrations greater than 1 vol. % and has been experimentally shown for mixed particle systems of varying sizes[19,22]. Above 14 vol. % the fraction of particles between 200-300 µm in the 114-µm sample exceeds 1 vol. %. Furthermore, although scattering attenuation for the lower size fraction in the 114-µm particle decreases, the viscous dissipation effect will rise. Hence, difference in attenuation measurements of 114 and 119-µm particles appears to be due to the nature of their size distributions.

Figure 10:
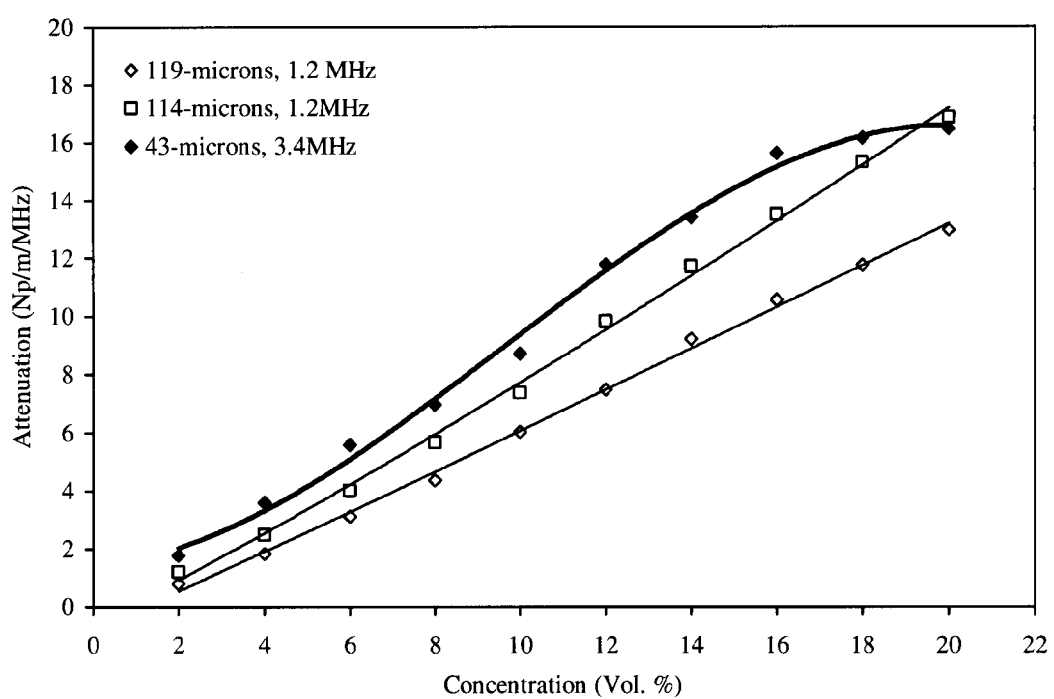
FIG. 10 plots the comparison of attenuation/peak frequency for 114 and 119-μm particles using 1.2 MHz transducer.

The trend of attenuation of 114 and 119-µm particles with concentration showed significant difference when, the kr values were reduced from 0.8 to 0.3. In this region viscous attenuation is the dominant mode of energy loss and no change in the peak frequency was observed. FIG. 10 shows the attenuation measurements at kr~0.3 for 114 and 119 µm particle samples (at 1.2 MHz) along with 43-µm particles (at 3.4 MHz frequency). Unlike measurements at 3.4 MHz, the attenuation of 114-µm particles are higher than 119-µm particles even at low concentration. Higher attenuation measured in the suspension of 43-µm particles shows that the contribution of viscous attenuation increases with decrease in particle size and is in agreement with literature.[8] Hence, the difference in attenuation of 114 and 119-µm particles can be attributed to small particles in the 114-µm sample. FIG. 9 shows that 25% of 114-µm particles are below 60-µm. With increase in concentration from 4 vol. % to 20 vol. % the concentration of smaller particles (<60-µm, kr~0.15) in 114-µm particle suspension increases from 1 to 5 vol. % and starts contributing significantly to the total attenuation. This results in an increase in attenuation measurements of 114 compared to 119-µm particles at higher concentrations.

Unlike 43-micron particles at 3.4 MHz (kr~0.3) no effect of particle-particle interactions was observed with 114 and 119-µm particles even though the kr values are similar. Particle-particle interactions during viscous dissipation are dependent on the viscous layer thickness and the inter-particle separation. The viscous layer thickness is affected by the viscosity, density of the medium and the frequency of the acoustic pulse.[18]

$$\delta_v = \sqrt{\frac{2\mu_f}{\omega\rho_f}} \tag{6}$$

Particle-particle effects are caused when the viscous layers of adjacent particles interact and the likelihood of such interactions increases with increase in the number of particles. The viscous layer thickness obtained at 1.2 MHz frequency is ~1.6 times the thickness at 3.4 MHz frequency. However, the average number of particles at 18 vol. % for 43-µm particle size is more than that of 114,119-µm by ~19 times. Hence, the onset of particle-particle interactions for 43-µm particles occurs at a lower concentration as compared to 114 and 119-µm particles.

In light of the above explanation, it is clear that particle sizing using attenuation spectroscopy relies on the extent of attenuation variation with frequency. Hence, attenuation has to be measured over a broad range of frequencies to enable PSD determination. Traditional model based methods for PSD determination has been restricted to the long wave propagation regime. However, this regime cannot be achieved for particles much larger than 10-µm over a sufficiently broad frequency range. This limitation is further discussed below by comparing the measured attenuations at low kr values with calculated attenuations using Allegra and Hawley[10] model.

Figure 11:
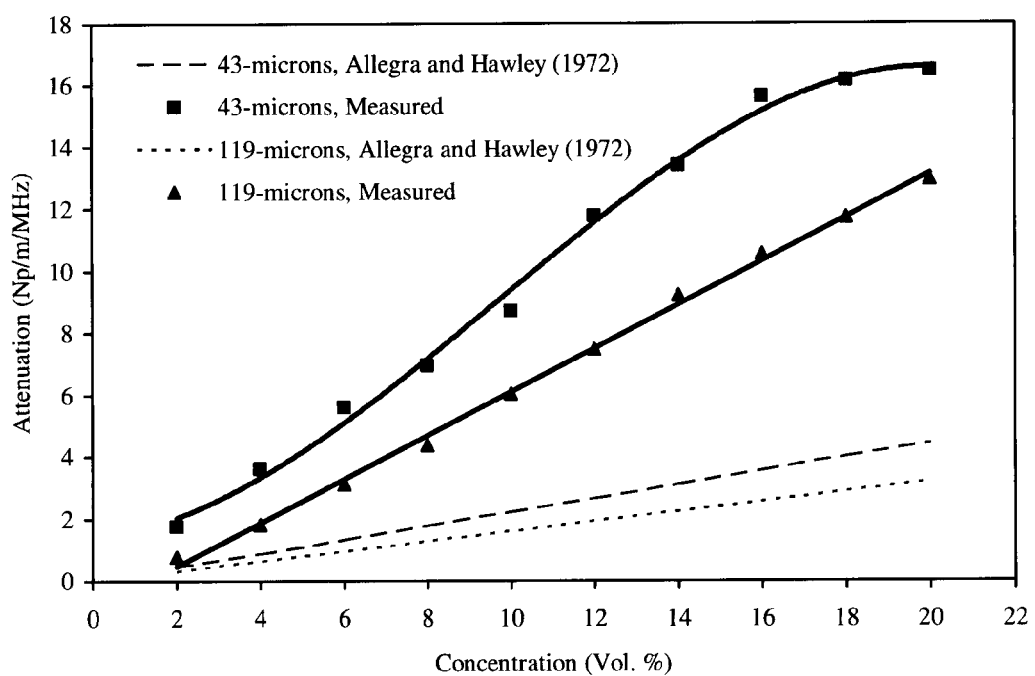
FIG. 11 provides a comparison between measured and predicted (Allegra and Hawley[9]) attenuation/peak frequency at 0.3 kr.

Allegra and Hawley[10] model is based on the equation of continuity (mass conservation) and Navier-Stokes equation (momentum conservation) which are used to derive the wave equations for the compressional, shear and thermal propagation. The model generates attenuation for mono-sized particles in the long wave propagation regime i.e ($\lambda \gg r$). The attenuation in polydispersed suspensions can be calculated using Equation 8 and is compared with measurements of 119-µm at 1.2 MHz and 43-µm at 3.4 MHz (FIG. 11). The explicit equations used for the calculation of attenuation of monosized particles were obtained from Allegra and Hawley[10]. The measured and calculated attenuations show an agreement only up to 2 vol. % concentration. The Allegra and Hawley[10] model fails when the wavenumber exceeds 0.1. The deviation of measurements from calculated attenuations can be attributed to the relatively high wave number of the particles used in this study. This indicates that even for 100-µm particles the maximum measurement frequency should be below 1 MHz to enable PSD predictions using long wave regime models. With further increase in particle size the available bandwidth is further diminished as frequencies below 40 kHz lie in the region of cavitation and cannot be used for particle sizing.

This drawback can be overcome by making measurements in the intermediate regime of propagation. In this regime absorption losses are dominant at lower wave numbers and scattering losses gain significance at higher wave numbers. However, neither of these losses is small enough to be completely neglected. Hence, the maximum frequency should be limited to avoid the regions of multiple scattering for large particle fractions. The minimum frequency should be high enough to avoid particle-particle interactions in the absorption region which occur due to the overlap of the viscous layers of neighboring particles. Limiting the wave propagation to this regime is advantageous as simple scattering and absorption models can be used for attenuation calculations.

Morse and Ingard[18] present a model to estimate attenuation in the intermediate regime of wave propagation. This model calculates the power lost in terms of scattering and absorption cross sectional areas of monodispersed particles at a given frequency. The power lost due to absorption or scattering divided by the power per unit area of the incident wave gives the absorption and scattering cross sections ($\Sigma_a, \Sigma_s$) of the particle. Hence, attenuation is the power contained in this cross sectional area of the incident beam which is lost during wave propagation. The power of a wave propagating through a medium filled with 'N' particles per unit volume of medium is given by Equation 9 and the attenuation can be calculated using Equation 10.

$$P_1 = P_o e^{-N(\Sigma_s + \Sigma_a)x} \tag{7}$$

$$\alpha = \frac{1}{2x}\ln\left(\frac{P_{i-1}}{P_i}\right) = \frac{1}{2}N\left(\sum_s + \sum_a\right)\left(\frac{\text{Np}}{\text{length}}\right) \tag{8}$$

$$\text{where, } N = \frac{3\phi}{4\pi r^3}$$

The scattering and absorption cross-sections for a spherical particle suspended in a fluid can be calculated by Equations 11 and 12 given by Morse and Ingard.[18]

$$\sum_s = 2\pi \int_0^\pi |\Phi(\vartheta)|^2 \sin\vartheta d\vartheta \text{ (length}^2) \tag{9}$$

$$|\Phi(\vartheta)|^2 = \left|\frac{i}{2k}\sum_{m=0}^\infty 2(2m+1)\frac{j'_m(kr) + i\beta_m j_m(kr)}{h'_m(kr) + i\beta_m h_m(kr)}P_m(\cos\vartheta)\right|^2 \tag{10}$$

$$\sum_a = \frac{k^4 r^4}{4\pi r^2}\sum_{m=0}^\infty \frac{(2m+1)\text{Re}(\beta_m)}{[h'_m(kr) + i\text{Im}(\beta_m)h_m(kr)]^2} \text{ (length}^2) \tag{11}$$

Where, '$h_m(kr)$' and '$j_m(kr)$' are spherical Hankel and Bessel functions of the order 'm' and '$h'_m(kr)$' and '$j'_m(kr)$' are their respective derivatives.

$$h_m(kr) = \frac{i^{-m}}{ikr}\sum_{s=0}^m \frac{(m+s)!}{s!(m+s)!}\left(\frac{i}{2kr}\right)^s e^{ikr} \tag{12}$$

$$j_m(kr) = \text{Re}[h_m(kr)] \tag{13}$$

$$\beta_m(kr) = i\frac{\rho_f c_f}{\rho_p c_p}\left(\frac{j'_m(k_f r)}{j_m(k_p r)}\right) + \frac{1}{2}(1-i)\left(\frac{m(m+1)}{r^2}k\delta_v\right) \tag{14}$$

$$c_f = \frac{1}{\rho_f \kappa_f}; c_p = \frac{1}{\rho_p \kappa_p} \tag{15}$$

The sound speed 'c' in fluid and particle are given by Equation 17 where, 'κ' and 'ρ' are their compressibility and density.

Theoretical models for the calculation of energy loss due to different propagation mechanisms, such as the model discussed above, have to account for the effect of pulse frequency, particle size and the physical properties of the different phases. Models available in literature for determination of absorption and scattering losses are based on the superposition principle. These models, such as the Morse and Ingard[18] model, are developed for monosized particles at a single frequency and the total attenuation is obtained by multiplying the attenuation caused by a single particle with the total number of particles present.

$$\alpha_{T,MD} = N\alpha \tag{16}$$

For polydispersed suspensions the normalized total attenuation can be calculated by superposing the effect of different size fractions.

$$\alpha_{T,PD} = \frac{1}{f} \sum_{i=1}^{i=n} N_i \alpha_i; \; N_i = \frac{3\phi}{4\pi r_i^3} \tag{17}$$

However, Equation 8 can only be used if there are no particle-particle effects in the system. This condition exists if the concentration of fines (viscous dissipation) is below the limit of inter-particle interactions and the regime of propagation for larger particles is in the region of single scattering (e.g. within the intermediate wave propagation regime).

Figure 12:
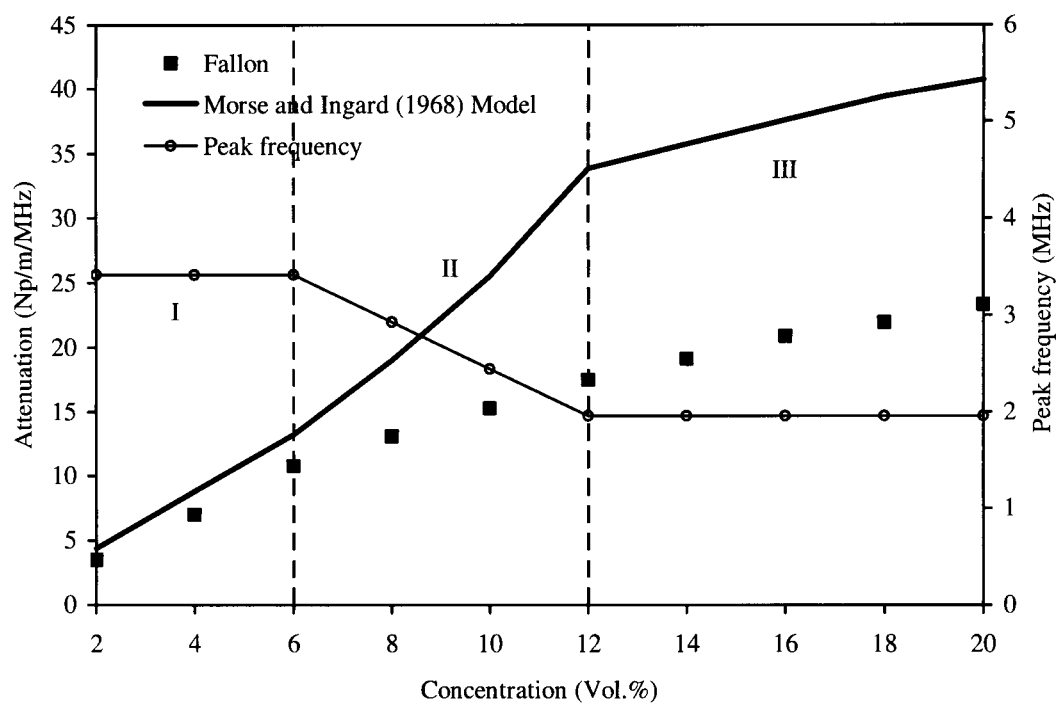
FIG. 12 provides a comparison between measured and calculated[17] attenuation/peak frequency for 114-μm particles using 3.4 MHz transducer.
Figure 13:
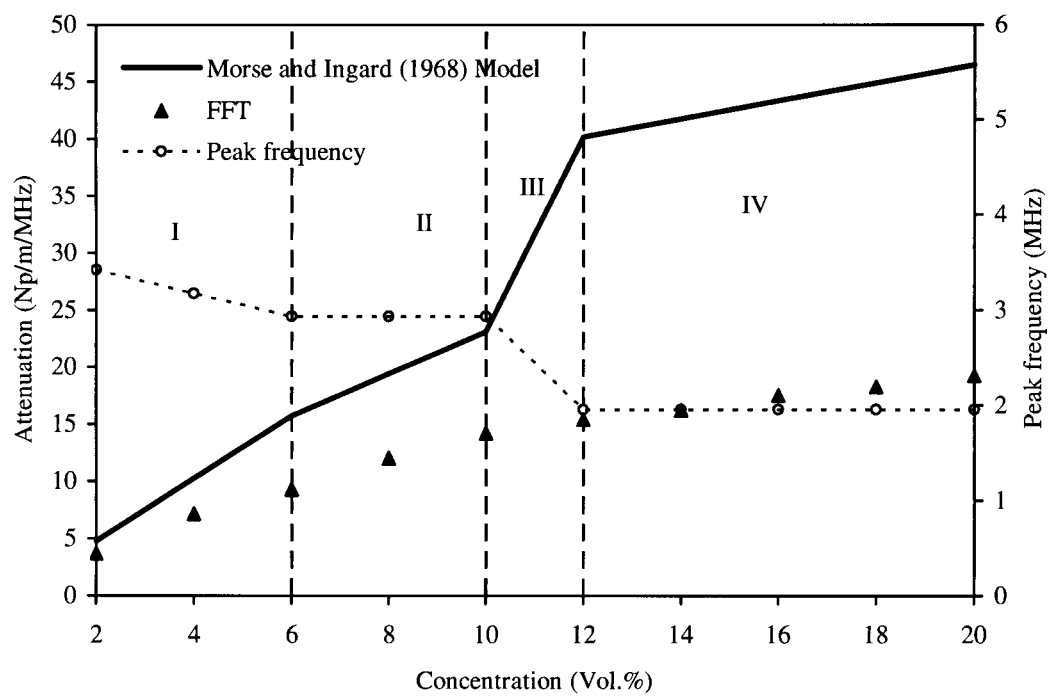
FIG. 13 plots a comparison between measured and calculated[17] attenuation/peak frequency for 119-μm particles using 3.4 MHz transducer FIG. 14 provides a polar plot of scattering intensity distribution for kr of 0.5, 1, 1.5 and 2.

FIGS. 12 and 13 show the comparison of normalized measured and calculated attenuation (Morse and Ingard[18]) at the peak frequency for 114 and 119-μm particles, respectively. The changes in peak frequency with concentration are also shown in the figures. The particle size distribution used for calculating total attenuation was measured using Malvern® Mastersizer. FIG. 12 shows a good agreement between measured and calculated attenuations for 114 μm particle suspension up to 6 vol. % concentration (Region I).

The calculated attenuation in Region II deviates away from the measurements even though there is a decrease in the peak frequency. This observation is contrary to expectations since attenuation in this regime has an inverse relationship with frequency. In Region III the rate of change in attenuation with frequency was constant and is likely due to no change in the peak frequency.

FIG. 13 shows the measured and calculated attenuation with change in concentration at the measured peak frequencies for 119-μm particles with 3.2 MHz transducer. Good agreement between measured and calculated attenuations was only obtained at 2 vol. %. Similar to 114-μm particles the rate of change in attenuation remains constant in Region II and IV when the peak frequency does not shift and rises rapidly in Region III with a decrease in the peak frequency.

The ability of the model to make reasonable attenuation predictions at low concentrations indicates that the deviations at higher concentrations are due to increase in particles concentrations. Dukhin and Goetz[8] have shown that particle-particle interaction in the scattering regime is minimal up to 40 vol. % concentration and should not be the reason for erroneous model calculations. A comparison of the magnitude of calculated attenuations from 12 to 20 vol. % in FIGS. 12 and 13 shows that higher attenuations were obtained for 119-μm particles even though the measurement frequency remains constant at about 2 MHz. This is contrary to the measurements as the attenuation of 114-μm particle is higher than 119-μm particles at these concentrations (FIG. 8). The PSD of these particles (FIG. 9) show that the 119-μm sample has a narrow distribution of predominantly large particles. This indicates that large attenuations calculated for 119-μm as compared to 114-μm particles is most likely due to the inability of the model to account for higher concentrations of larger particles.

Selected embodiments of the present invention, as disclosed below, address this problem by adapting models such as the Morse and Ingard[18] model to dense suspensions in the intermediate wave propagation regime.

SECTION 3

Accounting for Low-Angle Scattering into the Detector in the Intermediate Wave Propagation Regime The present inventors have discovered that the failure of prior art models such as the Morse and Ingard[18] model in dense suspension can be remedied by correcting the model for the finite size of the detector and the consequences of this finite size on scattering calculations.

Figure 14:
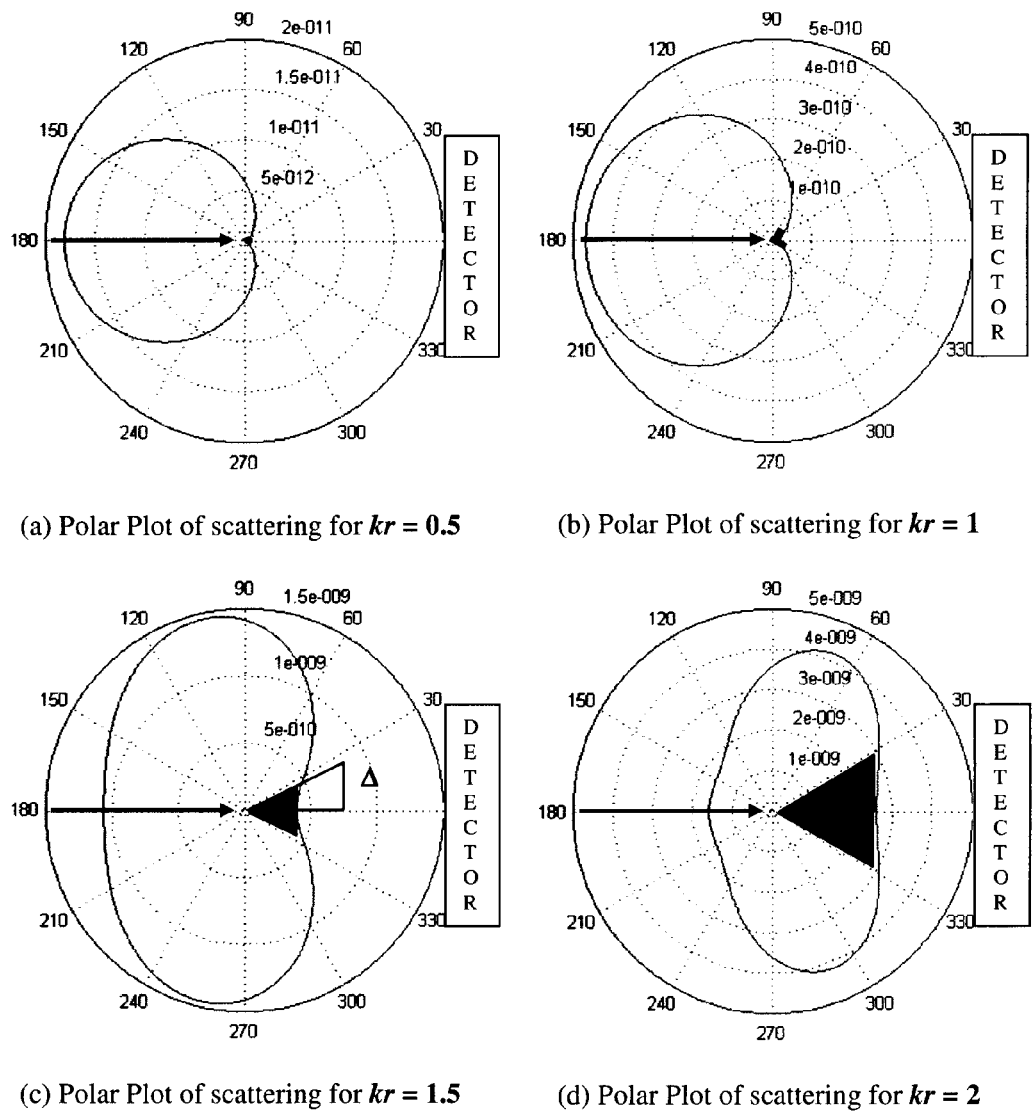

Mathematically speaking with reference to the Morse and Ingard[18] model, the power of the scattered wave at different angles in the scattering cross section can be calculated using Equation 12 where '$|\Phi(\theta)|^2$' is the angle-distribution factor of the scattered wave and 'θ' is the scattering angle.[18] FIG. 14 shows the polar plots of '$|\Phi(\theta)|^2$' at 0.5, 1, 1.5 and 2 kr calculated at a frequency of 3.4 MHz.

The scattering angle 'θ' is shown on the angular co-ordinate and the scattered power is shown on the radial co-ordinate and the direction of wave propagation is indicated on the figure. If the detector is infinitesimally small and is located at the point where the angle 'θ=0' then the integral in Equation 11 will give the total power abstracted from the incident beam due to scattering. Generally, however, the detector has a finite size and will subtend a measurement angle 'Δ' on the particles and is shown in FIG. 14c. Morse and Ingard[18] have shown that 'Δ~0' when the following relationship is satisfied.

$$\lambda << \frac{4r}{\Delta}. \tag{18}$$

Equation 11 can be simplified to the following form when the above condition is satisfied using the orthogonal property of the Legendre polynomial between the limits of 0 to $\pi$.[18]

$$\sum_s = \frac{4\pi}{k^2} \sum_{m=0}^{\infty} (2m+1) \left| \frac{j'_m(kr) + i\beta_m j_m(kr)}{h'_m(kr) + i\beta_m h_m(kr)} \right|^2 \; (\text{length}^2) \tag{19}$$

Morse and Ingard[18] have shown that the relationship in Equation 18 is true in the long wave regime of wave propagation where the forward scattering is negligible. However, the average kr value of the selected particles in the examples provided above (114 and 119-μm particles) is well above the long wave regime of wave propagation. At these kr values the measurement angle 'Δ' cannot be considered close to zero.

In the intermediate wave propagation regime, the power scattered within this angle will be measured by the detector and the experimental attenuation will be lower than the attenuation calculated using Equation 11. The effect of low angle scattering on measured attenuation will also increase with concentration as the number of particles increases. Good agreement of calculated attenuation with measurements up to 2 vol. % in FIGS. 12 and 13 indicates that this is negligible at low concentrations. At higher concentrations, however, the agreement will be poor as prior art models will incorrectly calculate the contribution of power scattered into the angle Δ to the predicted attenuation spectrum.

Therefore, a preferred embodiment of the present invention provides a method of determining and/or monitoring a particle concentration involving a model in which the size and position of the detector is accounted for in the calculation of the spectral attenuation. Preferably, the detector is accounted for by calculating the scattering cross section for only those angles that do not lie within the detector angle $\Delta$. In a preferred embodiment in the context of a model incorporating a scattering cross section calculated according to equation 11, this may be achieved by calculating the scattering cross section by integrating between the limits of '$\theta=\Delta$' and '$\theta=\pi-\Delta$' to account for the measurement of low angle scattered waves:

$$\Sigma_s = 2\pi \int_\Delta^{\pi-\Delta} |\Phi(\theta)|^2 \sin(\theta) d\theta. \quad (20)$$

The measurement angle '$\Delta$' is required for the calculation of the attenuation cross section using Equation 20. This angle may be obtained according to multiple methods, as discussed below.

In one embodiment, the measurement angle may be obtained from geometrical measurements relating to the size of the detector and the location of the scattering mixture relative to the detector. In a non-limiting example, the angle '$\Delta$' may be approximated as the average angle subtended by a point lying on the circumference of the receiver to the maximum and minimum location on the receiver/detector axis. This simple geometrical definition equates $\Delta$ to approximately the average angle subtended by scattering media relative to the detector. Those skilled in the art will appreciate that other related geometrical definitions and/or approximations for the angle $\Delta$ may alternatively be used to obtain an improvement relative to prior art methods. However, the simple geometrical definition will only be approximately valid as long as the effect of re-scattering of the scattered wave is not prominent, which is expected to be valid up to 40 vol. % concentration[8].

In yet another embodiment, the angle $\Delta$ may be obtained through a calibration procedure in which a sample with a known particle distribution is measured. In this embodiment, which is discussed further below, an initial guess of made for the angle $\Delta$ (for example, using the geometric estimation method provided above), and a particle distribution is estimated. The angle $\Delta$ is then varied from the initial guess value and the process is repeated one or more times. The angle $\Delta$ is then selected to be the angle that provides the best correspondence between the calculated particle distribution and the known particle distribution.

With the above inventive improvement to the calculation of the scattering cross-section, it follows that the total attenuation in a polydispersed suspension at the peak frequency can now be calculated by combining Equations 8, 10, 13 and 20 as shown below.

$$\alpha_{T,PD} = \frac{1}{2f} \sum_{i=1}^{i=n} N_i \left( \sum_{si} + \sum_{ai} \right) \left( \frac{Np}{\text{length} \cdot \text{MHz}} \right) \quad (21)$$

Figure 15:
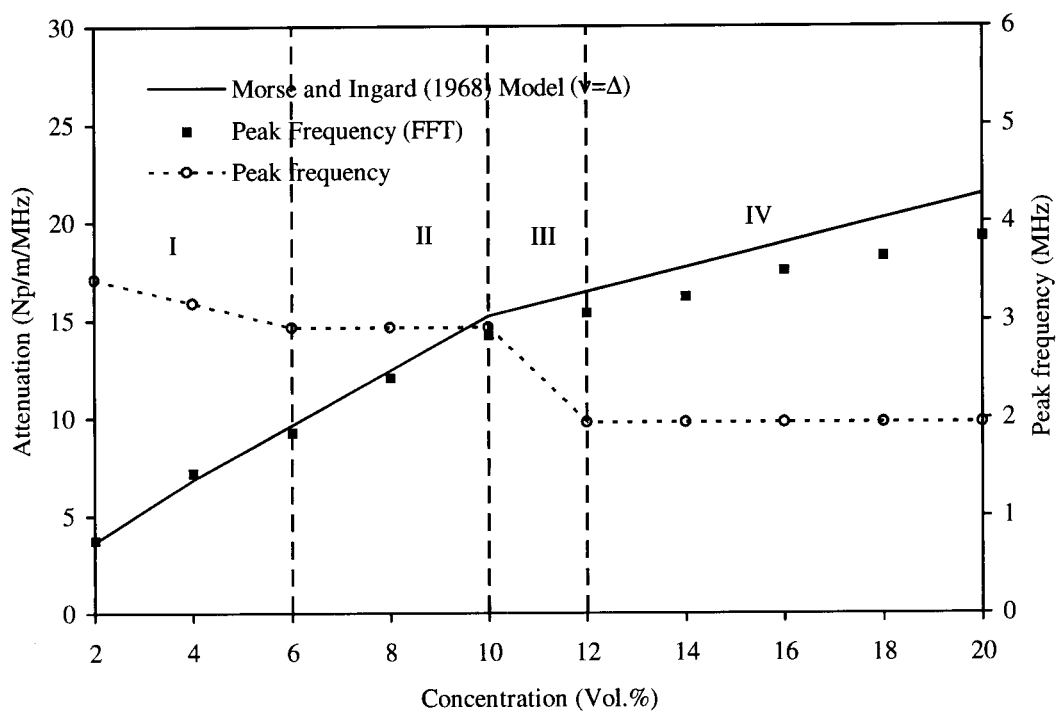
FIG. 15 shows a comparison between measured and calculated attenuation/peak frequency (with low angle scattering) for 119-μm particles using 3.2 MHz transducer.

The approximation proposed above was tested to predict the attenuation at different concentrations for 119-μm particles based on a known particle size distribution and is shown in FIG. 15. The figure shows good agreement between the measured and calculated attenuations when the low angle scattering is included in model calculations. Similar improvement in model predicted attenuations were also obtained for 114-μm particles.

Figure 16:
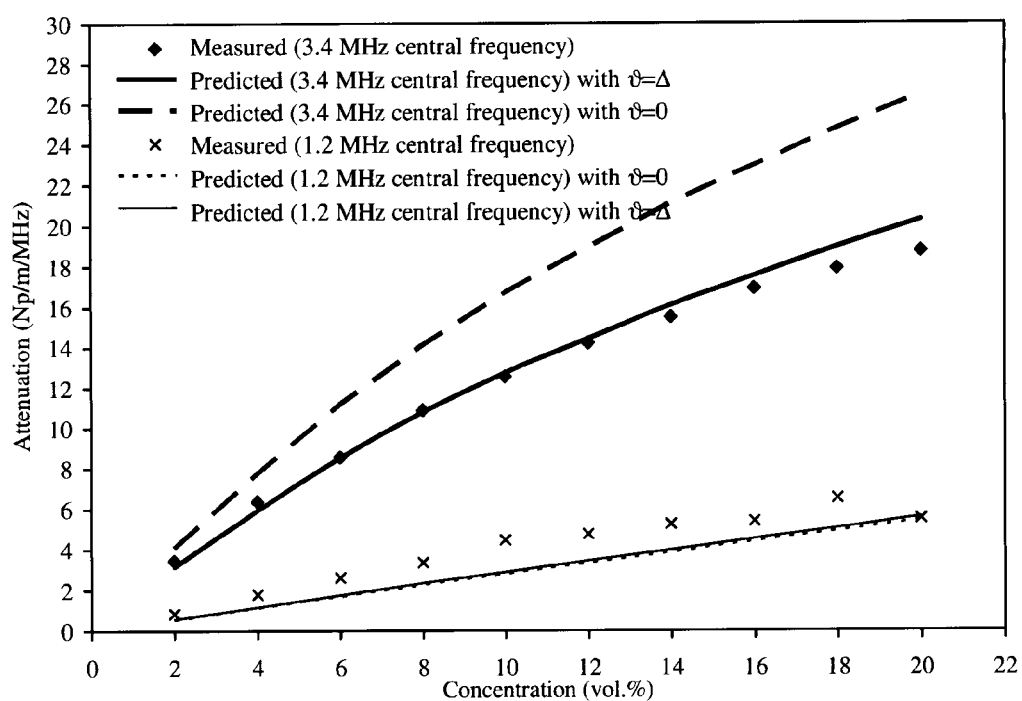
FIG. 16 plots the change in measured and calculated total attenuation with concentration for 119-μm particles using original Morse and Ingard[17] model and with model modification according to a preferred embodiment of the invention.
Figure 17:
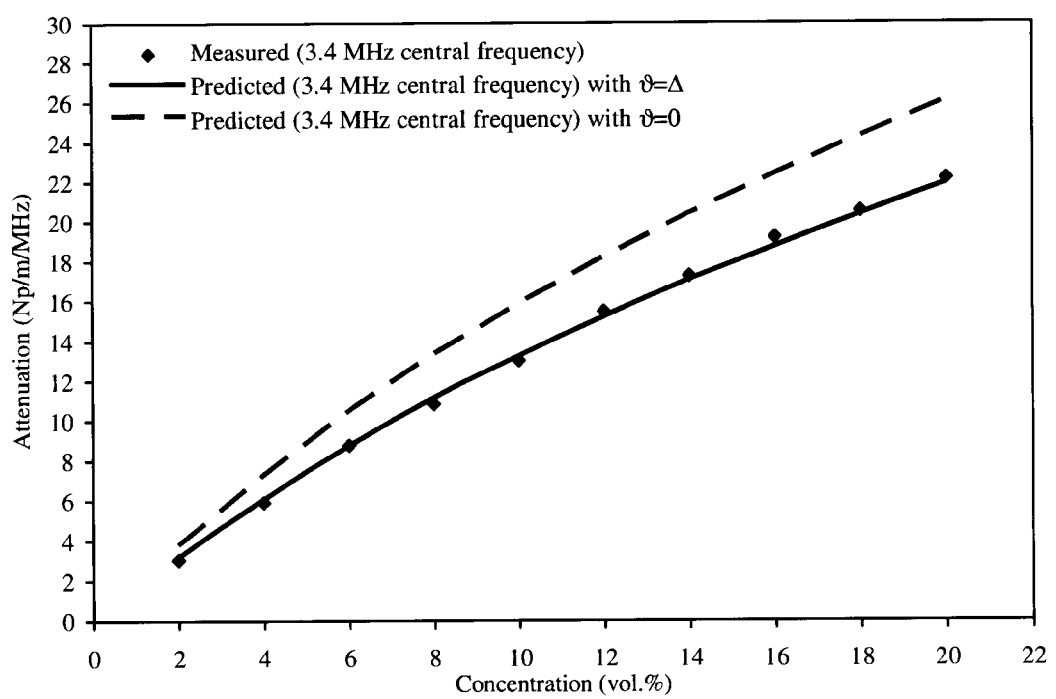
FIG. 17 plots the change in measured and calculated total attenuation with concentration for 114-μm particles using original Morse and Ingard[17] model and with model modification according to a preferred embodiment of the invention.

FIG. 16 compares the measured and calculated effective attenuations (at $\theta=0$ and $\theta=\Delta$) for 119-μm particles using 3.4 and 1.2 MHz central frequency transducers. As expected the effect of measurement angle '$\Delta$' is significant for higher frequency transducer due to dominance of scattering attenuation. However, at 1.2 MHz its effect can be neglected as both equations predict similar attenuations. FIG. 17 shows good agreement between measured and predicted total attenuation for the 114-μm sample measured using 3.4 MHz central frequency transducers. The proposed modifications to the model (along with the use of weighting factor discussed below) to replicate the measurement conditions in model calculations shows that good agreement with measured attenuations can be obtained in dense suspensions. Hence, the modified form of the Morse and Ingard[18] model is a suitable candidate for the deconvolution algorithm to obtain model based PSD in dense suspensions.

SECTION 4

Improvement Involving Frequency-Dependent Weight Factor

As discussed above, Equation 22 can be used to obtain the normalized attenuation at different frequencies from the FFT of a broad band acoustic pulse.

$$\alpha_f = \frac{1}{2xf} \ln\left(\frac{P_{i-1,f}}{P_{i,f}}\right) \left(\frac{Np}{\text{length} \cdot \text{MHz}}\right) \quad (22)$$

The calculated attenuation using the aforementioned modification of the Morse and Ingard[18] model can be tested at different frequencies using the above equation. However, due to the shift in the frequency spectrum a consistent set of frequencies is not available for the entire concentration range. This will impair the calculation of a particle size distribution by introducing and/or amplifying unwanted and unnecessary noise contributions in a measurement system.

The effect of shift in the frequency spectrum can be accounted for by using a weighting factor that scales the contribution of the different components of the attenuation spectrum based on their relative power content. In a preferred embodiment, this may be achieved using a linear or proportional scaling as shown in equations 23 and 24 below. This modified attenuation spectrum is then used for comparison with a calculated attenuation spectrum for an improved comparison with less presence of noise.

$$\alpha_{f,m}(\text{Np}/m/\text{MHz}) = w_f \frac{1}{2x \cdot f} \ln\left(\frac{P_{f,i-1}}{P_{f,i}}\right) \quad (23)$$

$$w_f = \frac{P_{f,i}}{\sum_{f_{min}}^{f_{max}} P_{f,i}} \quad (24)$$

The weighting factor ($w_f$) scales the attenuation at each frequency according to its strength in the measured signal. This scaling will exclude attenuations at higher frequencies when their power content becomes less than the acceptable minimum limit. It also allows the inclusion of attenuations at lower frequencies which become significant with increase in concentration. Another advantage of attenuation scaling is that it gives greater weight to frequencies with higher power content. Hence, errors caused due to measurement uncertainties at frequencies with low power content are reduced. While the form of the weighing function shown in 24 represents a preferred embodiment of the invention, those skilled in the art will appreciate that other forms may be used to achieve a similar improvement.

In an alternative embodiment, the weight factor may be set to zero at frequencies where the weight factor, as calculated above, falls below a pre-defined threshold. In a preferred embodiment, the threshold is a fixed threshold, and is preferably in the range of approximately 0.3 to 0.5, and is more preferably about 0.4.

The total effective measured attenuation of the acoustic pulse can then be obtained using Equation 25.

$$\alpha_{T,M}(Np/m/MHz) = \sum_{f_{min}}^{f_{max}} w_f \frac{1}{2x \cdot f} \ln\left(\frac{P_{f,i-1}}{P_{f,i}}\right) \quad (25)$$

For comparison between measured and predicted attenuation, as utilized in embodiments of the invention for the determination of a particle size distribution, the weighting factor should also be used in Equation 21 to replicate the frequency spectrum in model calculations.

SECTION 5

Improved Method of Particle Size Determination

Figure 18:
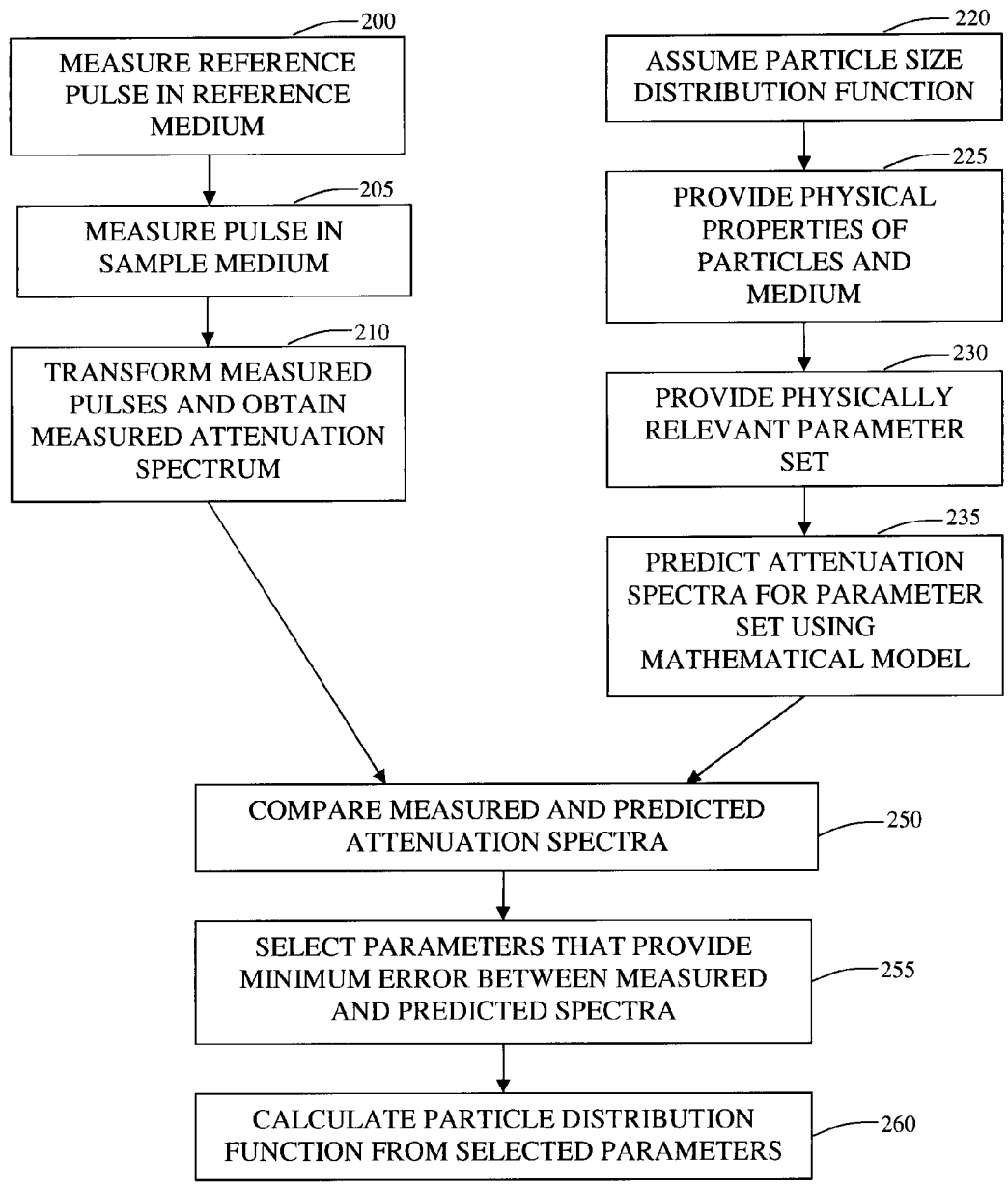
FIG. 18 is a flow chart illustrating a deconvolution algorithm for particle size distribution determination.

As discussed above, the particle size distribution of a sample can be obtained by measuring the attenuation spectrum and subsequently optimizing the parameters of an assumed size distribution to minimize the error between measured and predicted attenuation spectra. An overview of this method is illustrated in FIG. 18, which provides a flow chart showing an embodiment involving a global search method.

In step 200, a reference time-domain pulse measurement is obtained by measuring the transmission of an ultrasonic pulse through a reference medium, such as a particle-free liquid characteristic of the sample to be measured. The sample having an unknown particle size is subsequently measured in step 205. Both pulse measurements are converted to the frequency domain in step 210, for example, by the application of a fast Fourier transform algorithm.

In step 235, a simulated attenuation spectrum is obtained using a model that can predict an attenuation spectrum. An example of a suitable model is the Morse and Ingard[18] model discussed above. The inputs to the model include a selection of the functional form of a particle distribution function (provided in step 220) and physical properties of the particles and the mixture liquid (provided in step 225). Physical properties of the particles may include, but are not limited to, the density of the fluid and the suspended solids, the compressibility of the medium and the suspended solids, and the viscosity of the medium. The functional form of the distribution function is selected based on the type of sample. For example, a log-normal distribution function is a widely used analytical size distribution for describing distribution of particles. Alternatively, other functional forms of the distribution function may be used, such as the bimodal distribution, as described in reference 8.

In the ensuing steps of the method, the particle size distribution is estimated by obtaining the best fit of the parameters of distribution function. One preferred method is the global search technique, which is described in FIG. 18. The global search method involves finding the optimum distribution parameters for best-fit particle size distribution.

In step 235 of the flow chart, the theoretical attenuation spectra are calculated for all physically feasible parameters to obtain the error matrix. In the exemplary case of a log-normal distribution, the functional form of the distribution function is shown below:

$$\varphi_d^{\mu,\sigma} = \frac{1}{d\sigma\sqrt{2\pi}} e^{\frac{-(ln(d)-\mu)^2}{2\sigma^2}} \quad (26)$$

The two parameters used for defining this distribution are its geometric mean ($\mu$) and standard deviation ($\sigma$). In a preferred embodiment, the possible values which can be achieved by the parameters '$\mu$' and '$\sigma$' can be restricted by defining the minimum ($d_{min}$) and maximum ($d_{max}$) particle size which can be present in the system. Hence, for a given '$\mu$' ($d_{min} < e^\mu < d_{max}$) the values of '$\sigma$' should satisfy Equation 27.

$$\varphi_{d_i}^{\mu,\sigma} \begin{cases} \varphi_{d_i}^{\mu,\sigma} & \text{if } \sum_{i=1}^{n} \varphi_{d_i}^{\mu,\sigma} \approx 1 \\ 0 \end{cases} \quad (27)$$

In a preferred embodiment of the invention, the parameters are varied in sufficiently small increments to generate a desired resolution. For example, the parameter $\mu$ may be incremented by steps of 1 $\mu$m when generating the physically relevant parameters. Similarly, the parameter $\sigma$ may be incremented in sufficiently small steps to provide desired resolution (and for example, provided that the computation time is maintained below a desired duration). In cases where the physically relevant particle size range is not known a priori, the range can be increased to accommodate a wider range of possible solutions.

Having provided the set of physically relevant parameters, the attenuation spectra due to each particle size at a given frequency can be calculated using the model in step 235. The calculated attenuation spectra are then compared to the measured attenuation spectra in step 240, and a global search algorithm (known to those skilled in the art) can be employed to select the parameters that provide the best fit between the calculated and measured spectra. Finally, in step 245, the selected parameters may be used to calculate the estimated particle distribution function.

Figure 19:
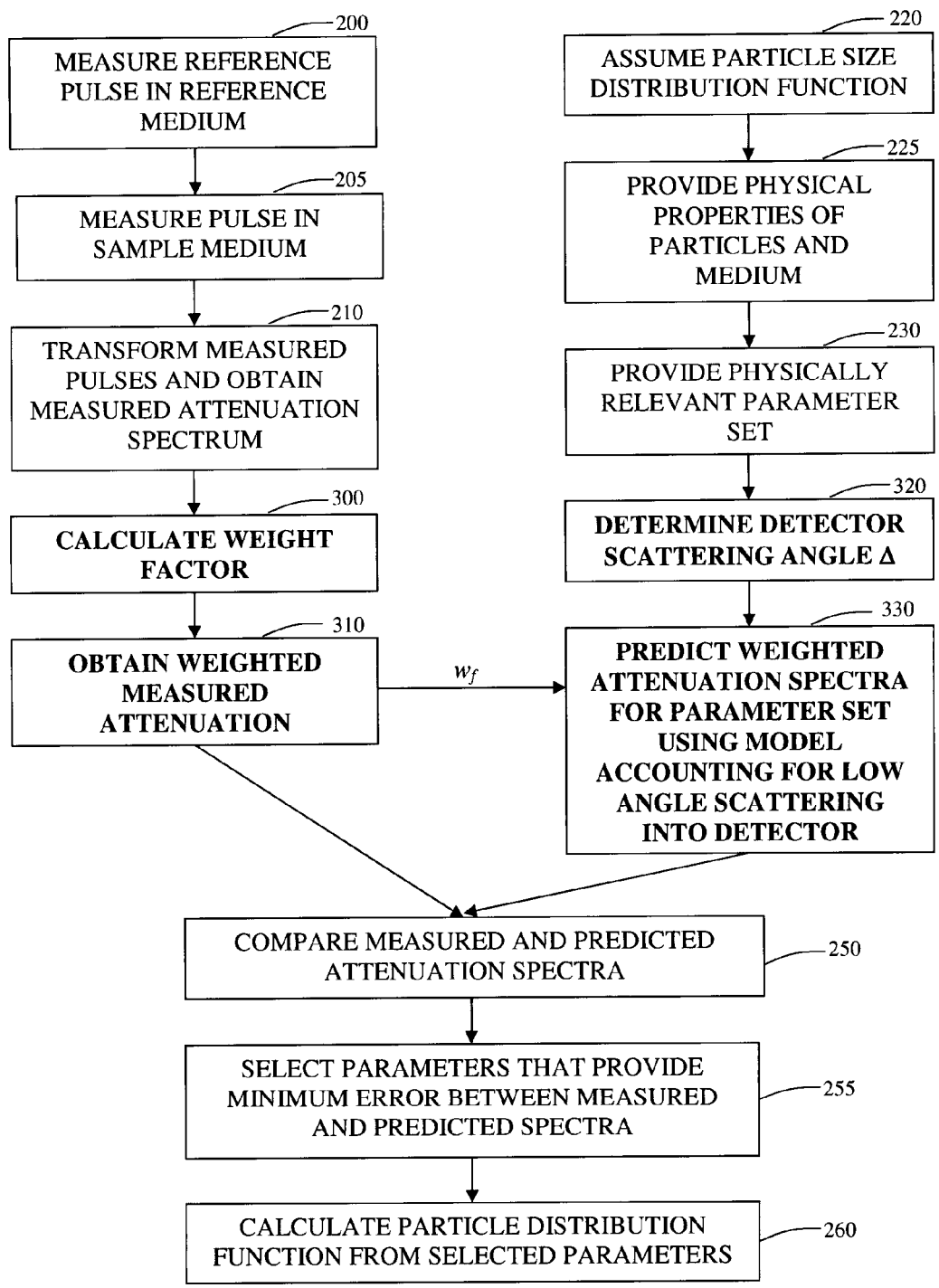
FIG. 19 is a flow chart illustrating an improved deconvolution algorithm for particle size distribution determination according to selected embodiments of the invention.

As discussed in Section 3, the application of such a method in the intermediate wave propagation regime often fails when the particle concentration is increased beyond small values. FIG. 19 illustrates a preferred embodiment of the invention in which an improved method of estimating the particle distribution size is provided. Preferably, the bandwidth of the ultrasonic transmitter and detector employed in the measurement are selected to produce and measure ultrasonic pulses having frequency content corresponding to the intermediate wave propagation regime.

The flow chart shown in FIG. 19 includes several additional steps that lead to an improved estimate for the particle size distribution. Generally, the method adapts the method shown in FIG. 18 to include the inventive improvements discussed in Sections 3 and 4, namely the refinement of the attenuation spectra model to account for low angle scattering into the detector, and also the use of a weighing factor that limits the contribution of noise in the measured attenuation spectra and accounts for an effective frequency shift of the transmitted pulse. While both of these improvements are incorporated into the improved method illustrated in FIG. 19, it is to be understood that these two improvements are operatively independent of each other, and either or both can be employed to improve the estimation of the particle size density.

Referring to FIG. 19, in the portion of the method involving the measurement of the attenuation spectrum, additional step 300 includes the calculation of weight factor. This weight factor is preferably calculated according to the method disclosed in Section 4 above. For example, equation 24 may be employed for the calculation of the weight factor. This weight factor is subsequently used in step 310 (preferably according to equation 25) to modify the measured attenuation spectrum, effectively emphasizing the high-power transmitted spectral components. Additionally, the weight factor is employed in step 330, where it is applied to the calculation of the predicted attenuation spectra. As discussed above, the inclusion of the weight factor according to the present embodiment of the invention improves the signal-to-noise ratio and generally produces a more accurate determination of the particle size distribution.

FIG. 19 also includes modifications that account for low angle scattering effects in the predicted attenuation spectrum, particularly the effect of low angle forward scattered power into the detector. As discussed in Section 3, this effect is known to occur in the intermediate wave propagation regime and can have a significant effect on the estimated particle size distribution. Step 320 involves the estimation of the angle $\Delta$, which was discussed extensively in Section 3.

As described above, the angle $\Delta$ may be obtained from geometrical measurements relating to the size of the detector and the location of the scattering mixture relative to the detector. Again, in a non-limiting example, the angle '$\Delta$' may be approximated as the average angle subtended by a point lying on the circumference of the receiver to the maximum and minimum location on the receiver/detector axis. An alternative approach to determining the angle $\Delta$ with improved accuracy is described below.

After having determined the angle $\Delta$, it is used in step 330 to provide a more accurate estimate of the attenuation spectrum for a given set of physical parameters. In a preferred embodiment, step 330 involves predicting attenuation spectra by limiting the scattering angle to exclude losses due to scattering into the collection aperture of the detector. In a more preferred embodiment, this is achieved by calculating a scattering cross section $\Sigma_s$ according to equation 20. The inclusion of these modifications to the procedure for predicting the attenuation spectra provides for an improved particle size distribution estimate when performing steps 250-260 when the frequency bandwidth is selected to overlap the intermediate wave propagation regime.

As discussed above, the angle $\Delta$ may be obtained based on a simple geometrical approximation. However, depending on the exact nature of the experimental apparatus, particularly the physical properties of the transmitter and detector, the value obtained using the geometrical estimate may not be the best value.

Figure 20:
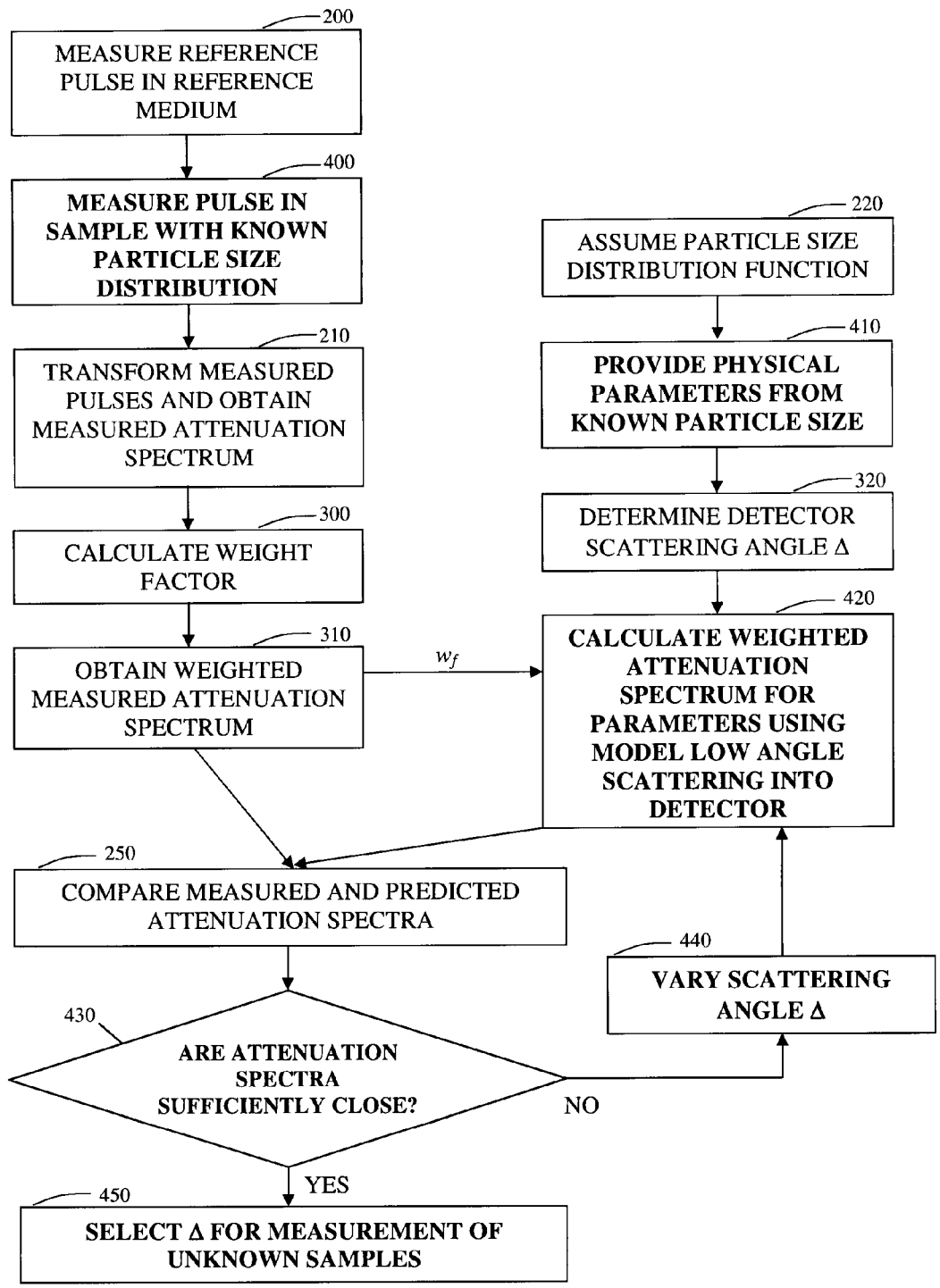
FIG. 20 is a flow chart illustrating method of determining the angle Δ.

FIG. 20 provides a method for obtaining an improved estimate of the angle $\Delta$ using an iterative approach based on the measurement of a sample with a known particle size distribution. The method is similar to that of FIG. 19, with one major difference being that in step 400, a sample with a known particle size distribution is measured instead of an unknown sample. As in FIG. 19, an estimated value for the angle $\Delta$ is provided in step 320 (e.g. using a geometrical estimate). The knowledge of the particle size distribution allows one to directly provide (in step 410) known parameters for use in the calculation of attenuation spectrum in step 420 using the estimated value for the angle $\Delta$.

The calculated attenuation spectrum is then compared with the measured attenuation spectrum in step 250, and in step 430, an assessment is made as to whether or not the predicted attenuation sufficiently matches the measured attenuation spectrum. The assessment may be made based on convergence criteria, such as the percentage offset between the two curves at a given frequency. If the match is sufficiently close, then the value of the angle $\Delta$ used in calculated attenuation spectrum is selected for use in subsequent measurements of unknown samples. Alternatively, if the match is not sufficiently close, the value of the angle $\Delta$ is varied, and the attenuation spectrum is re-calculated and again compared to the measured attenuation spectrum. This process is repeated until a sufficiently close match is found, at which point the corresponding value of the angle $\Delta$ is selected and retained for use in subsequent measurements of unknown samples.

The following discussion provides specific details regarding a non-limiting example of how the global search method may be applied in the context of a particle size distribution having a log-normal functional form. The weight factor described above is incorporated into the calculations according to Equation 28 for all distributions defined by the possible values of '$\mu$' and '$\sigma$'. The total weighted attenuation due to all particle sizes at a given frequency is given by Equation 29 and the calculated effective attenuation of the pulse can then be obtained using Equation 30. Preferably, the scattering cross section $\Sigma_s$ is obtained according to equation 20, as discussed above.

$$C_{d_i,f} = w_f \frac{3\varphi_{d_i}^{\mu,\sigma}}{4\pi r_i^3}\left(\sum_s + \sum_a\right) \tag{28}$$

$$\alpha_{w_f}^C = \sum_{i=1}^{n} C_{d_i,f} \tag{29}$$

$$\alpha_{\mathit{eff}}^C = \sum_{f_{min}}^{f_{max}} \alpha_{wf}^C \tag{30}$$

Similarly, the measured weighted attenuation at each frequency and the measured effective attenuation of the pulse can be obtained using Equations 31 and 32.

$$\alpha_{wf}^M = \alpha_f^M w_f^M \tag{31}$$

$$\alpha_{\mathit{eff}}^M = \sum_{f_{min}}^{f_{max}} \alpha_{wf}^M \tag{32}$$

The volume fraction of particles in the system can be predicted using the superposition principle (Equation 33) and the error between known and predicted concentration is given by Equation 34.

$$\phi^C = \frac{\alpha_{\mathit{eff}}^M}{\alpha_{\mathit{eff}}^C} \tag{33}$$

$$\Delta_\phi = |\phi - \phi^C| \tag{34}$$

The following constraints have to be satisfied by the predicted attenuation for the log-normal parameters to define the particle size distribution in the system.

$$\sum_{f_{min}}^{f_{max}} \alpha_{wf}^C \phi^C \approx \sum_{f_{min}}^{f_{max}} \alpha_{wf}^M \quad (35)$$

and, $\Delta_\phi \to 0$

Hence, the best-fit of the parameters of log-normal distribution can be obtained by minimizing the sum of absolute errors between measured and predicted attenuation and the error in attenuation due to '$\Delta_\phi$' at each frequency. This minimization procedure may be achieved using known numerical methods that are best adapted for execution on a computing environment such as a personal computer.

$$E^{\mu,\sigma} = \sum_{f_{min}}^{f_{max}} (|\alpha_{wf}^M - \phi^C \cdot \alpha_{wf}^C| + \Delta_\phi \alpha_{wf}^C) \quad (36)$$

$$\min\{E^{\mu,\sigma}\} \to \varphi_d^{\mu,\sigma}$$

After performing the error minimization, the average size and standard deviation of particles in the system are calculated from the best-fit log-normal parameters '$\mu$' and '$\sigma$' using the relationships given in Equation 37.

$$d_{avg} e^{\mu+0.5\sigma^2}$$

$$\sigma_{Dist} = \sqrt{(e^{\sigma^2}-1)e^{2\mu+\sigma^2}} \quad (37)$$

The embodiments described above have been provided with reference to non-limiting models for calculating the scattering cross section, for using in determining the particle size distribution. However, those skilled in the art will appreciate that an appropriate absorption model should be employed to obtain the absorption losses and absorption cross section. Such losses are also present to a much lesser extent (but not insignificant), and freely available models known to those skilled in the art may be employed for their calculation. In the present example the absorption model used was adapted from the Morse and Ingard model discussed above. Those skilled in the art will recognize that various alternative absorption models known in the art may alternatively be used.

The aforementioned description of embodiments related to the determination of the particle size distribution have been provided using a non-limiting inversion algorithm involving a global search. However, those skilled in the art will readily appreciate that other inversion algorithms may be used, such as those disclosed in references 25, and 26, within the scope of the present embodiments.

Figure 21:
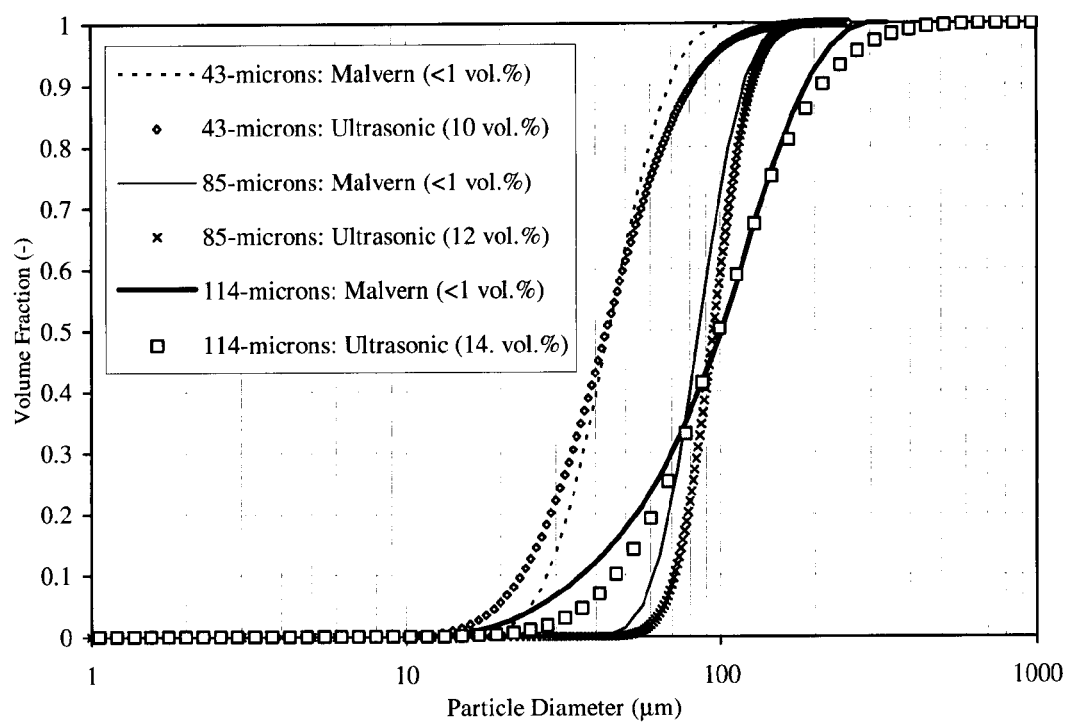
FIG. 21 plots a comparison of measured PSD using ultrasonic technique and Malvern Mastersizer® for 43, 85 and 114-μm particles suspension in DI-water.
Figure 22:
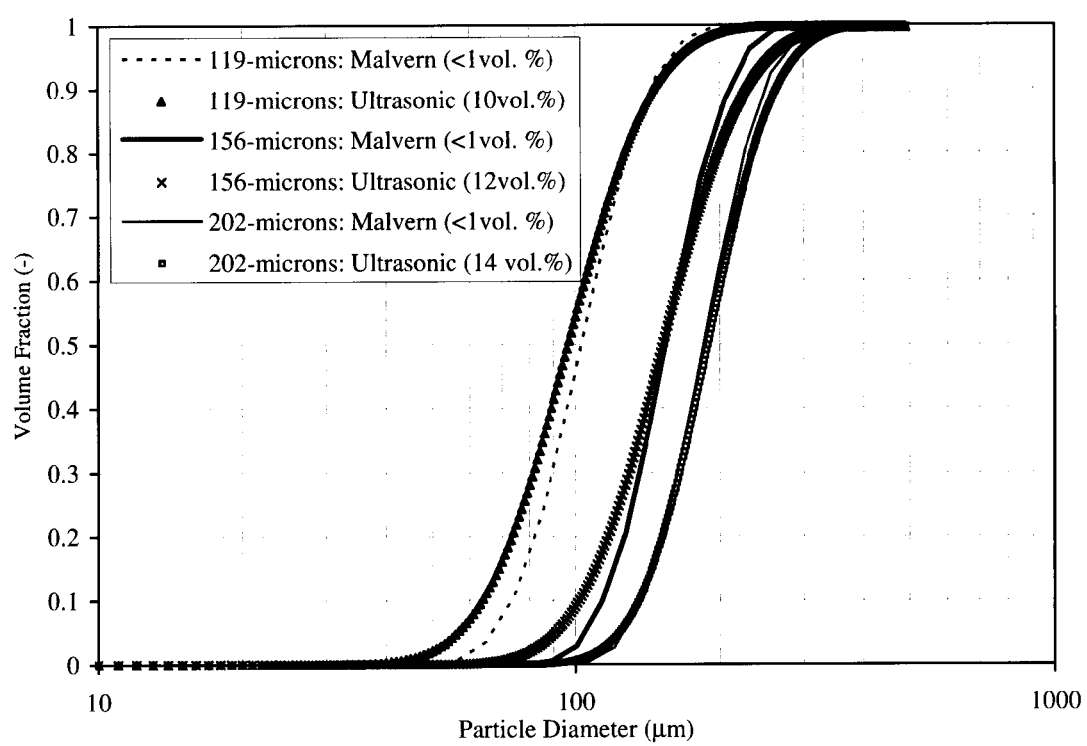
FIG. 22 provides a comparison of measured PSD using ultrasonic technique and Malvern Mastersizer® for 119, 156 and 202-μm particles suspension in DI-water.
Figure 23:
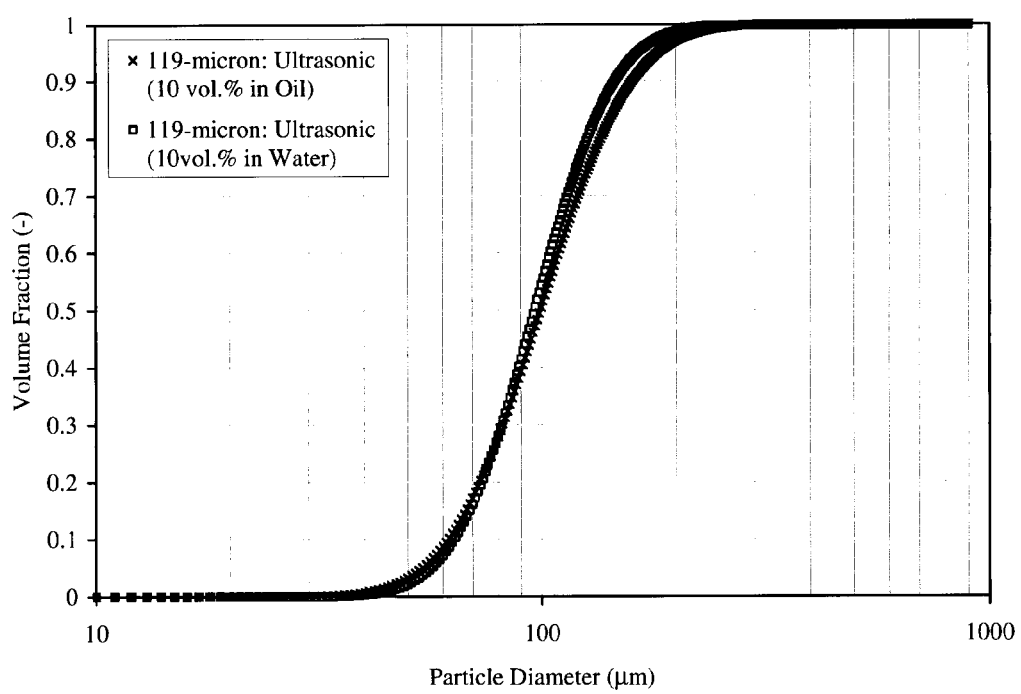
FIG. 23 plots a comparison of measured PSD using ultrasonic technique for 119-μm glass beads suspension (10 vol. %) in DI-water and canola oil.
Figure 24:
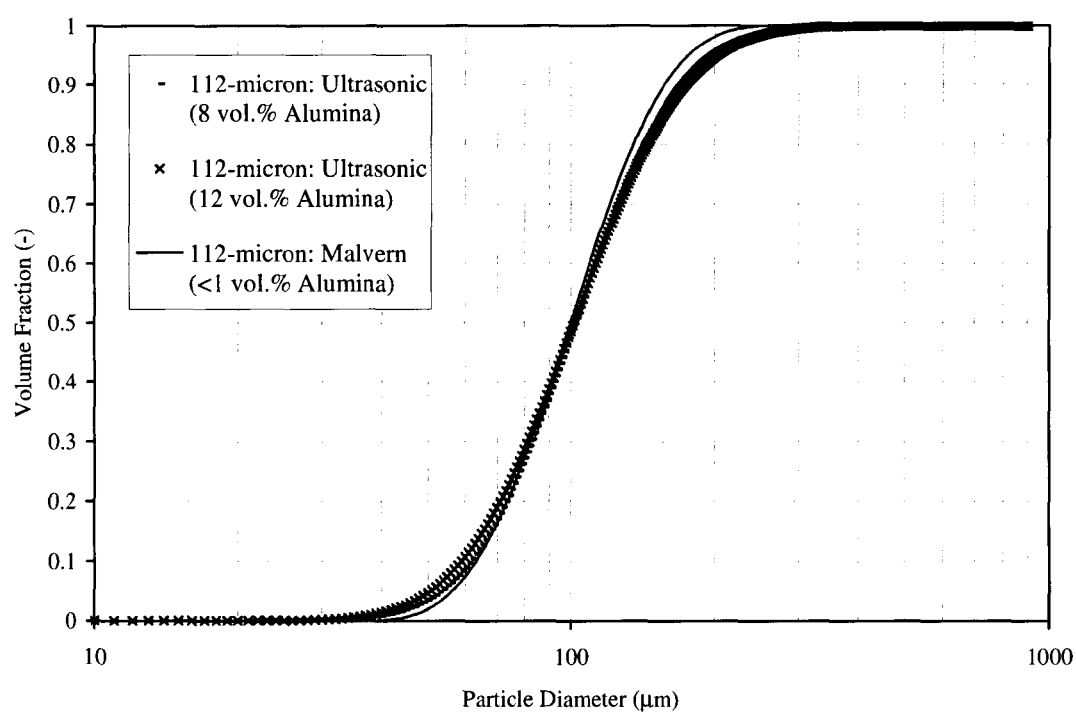
FIG. 24 plots a comparison of measured PSD using ultrasonic technique for 112-μm aluminum oxide suspension (8 and 10 vol. %) in DI-water with the measurements of Malvern Mastersizer®.

FIG. 19 shows the measured PSD using ultrasonic technique for 43, 85 and 114-μm particles at 10, 12 and 14 vol. %, respectively. FIG. 20 shows the measured PSD using ultrasonic technique for 119, 156 and 202-μm particles at 10, 12 and 14 vol. %, respectively. Offline PSD measured using Malvern Mastersizer® at concentrations less than 1 vol. % are also shown in these figures. Performance of the novel ultrasonic spectroscopy technique was also tested for glass beads suspension in canola oil and aluminum oxide suspension in DI-water. FIG. 21 shows that the measured PSDs for 119-μm glass beads (10 vol. %) in canola oil is similar to the measurements obtained in the DI-water suspension. FIG. 22 shows a comparison of the PSDs measured using ultrasound at 8 and 12 vol. % concentration for 112-μm aluminum oxide with the results obtained using Malvern Mastersizer® (<1 vol. %). The PSDs measurements were made using 3.4 MHz transducer with the search domain set between '$d_{min}$=1-μm' to '$d_{max}$=1000-μm' and the attenuations were predicted using the modifications proposed to the Morse and Ingard[18] model. The PSD measurements were obtained from the average of five pulses sampled at each concentration to obtain the mean attenuation spectrum.

Ultrasonic technique uses the volume-weighted absorption and scattering losses as opposed to projected surface area based laser diffraction measurements (Malvern Masterizer®) for PSD calculations. Based on the measurement principle different characteristics of the particle are measured and hence some differences between the PSDs generated by different measurement techniques are unavoidable. The measurements obtained using ultrasonic technique is more representative as compared to Malvern Mastersizer® which operates at concentrations less than 1 vol. % and can lead to significant sampling errors. Ultrasound has a good penetration depth (~50 mm) even under dense conditions and unlike laser diffraction measurements it can operate in opaque suspensions. Furthermore, the PSD measurements in the current study are based on the average of five pulses sampled at each concentration to obtain the mean attenuation spectrum. Higher data acquisition rate will enable signal averaging and hence generate a more representative spectrum.

Attenuation measurements in dense suspensions of particles were investigated to study the effect of particles concentration and measurement frequency in the intermediate wave propagation regime. Non-linearity in the measured attenuation with increase in concentration was attributed to the effect of shift in the frequency spectrum. Particle polydispersity effects on the attenuation measurements were studied using particles with the same average size but different distributions. It was observed that higher concentration of larger particles resulted in a decrease in the measured attenuation. The deviations at higher concentrations were attributed to the measurement of low-angle scattered waves by the detector. The inclusion of detector size in the calculation of attenuation using the Morse and Ingard[18] model resulted in good agreement with the measurements. A weighting factor was used to replicate the measurement conditions in the calculated attenuation spectrum. The PSD determined using the improvements proposed in this study showed that a model based technique can be used for measurements in the intermediate wave propagation regime at high suspension concentrations. The measured PSDs showed good agreement with the results of off-line Malvern Mastersizer®. Further improvements in the ultrasonic based measurements can be obtained using higher sampling rates and wider pulse bandwidth.

SECTION 6

System for Improved Measurement of Particle Size Distribution

Figure 25:
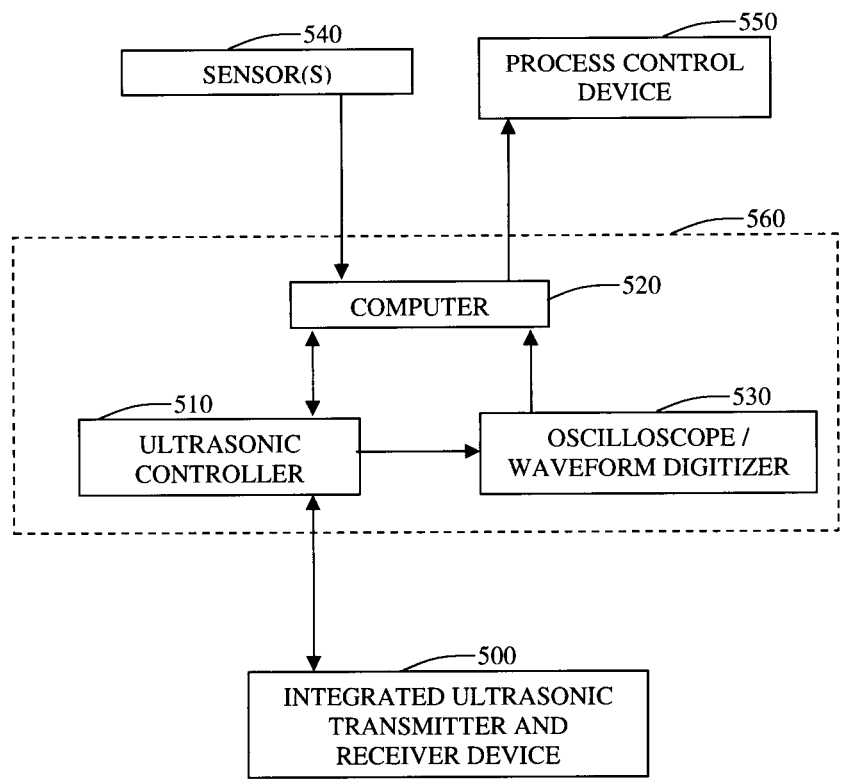
FIG. 25 provides a schematic of an ultrasonic measurement system according to a preferred embodiment of the invention.

FIG. 25 provides a non-limiting example of a system for implementing embodiments of the invention disclosed above. The system includes an integrated ultrasonic transmitter and receiver device 500 that maintains a fixed angle between the transmitter and receiver during operation. This integrated ultrasonic device is discussed in further detail below with reference to FIG. 26. The ultrasonic transmitter housed in the device is driven by an ultrasonic controller 510 (for example, a Fallon Ultrasonic® pulser/receiver unit), which preferably also interfaces with the ultrasonic receiver for receiving signals corresponding to transmitted ultrasonic pulses. The received signals may be processed directly by a computer (for example, a computer equipped with a data capture card) or may be first provided to an oscilloscope 530 for the capture and optional visualization of the received signal waveform. The computer is optionally interfaced with one or more sensors 540 that are provided to measure physical parameters related to the mixture being measured. Non-limiting examples of sensors include temperature, viscosity and pressure sensors. The computer includes a processor and is preferably programmed to determine the particle size distribution using embodiments of the invention disclosed above. Preferably, the computer is interfaced with one or more process control devices 550. Non-limiting examples of process control devices include a switch for turning off a process related device such as a mixing device, or an audible alarm for indicating that a desirable particle size distribution has been achieved.

While the computer 520, ultrasonic controller 510 and oscilloscope 530 are shown as separate devices in the system shown in FIG. 25, it is to be understood that alternate system configurations are possible within the scope of the present embodiment. In a preferred embodiment, these systems may be unified into a single device 560 that integrates the ultrasonic controller and waveform capture functions with the computer processor for the determination of a particle size distribution.

Additionally, although embodiments of the present invention have been disclosed using the non-limiting example of transducers and controllers providing ultrasonic pulses for attenuation measurements, those skilled in the art will appreciate that other forms of ultrasonic generation may be employed, such as, but not limited tone bursts and chirp signals.

Figure 26:
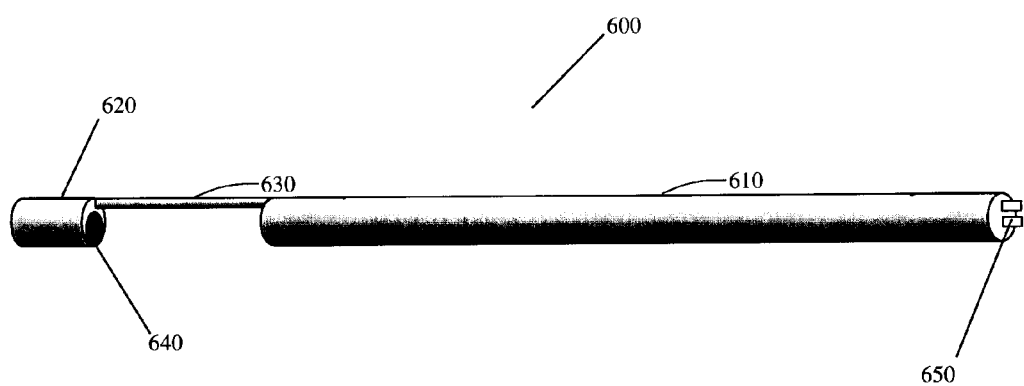
FIG. 26 is an illustration of an integrated coaxial ultrasonic device.

FIG. 26 illustrates a preferred embodiment of the invention in which an ultrasonic transmitter and receiver are provided as an integrated coaxial ultrasonic device. The device 600 comprises a first housing 610 for supporting an ultrasonic transmitter or receiver, and a second housing 620 for supporting a corresponding transmitter or receiver (shown at 640), such that the device comprises at least one transmitter and receiver pair. Preferably, the first housing 610 comprises an ultrasonic transmitter. Both housings are watertight to prevent the damage of the internally supported transducers and related electronics.

The first housing 610 and second housing 620 are aligned along a common longitudinal axis, thereby providing a fixed coaxial orientation for the measurement of ultrasonic attenuation. The first and second housings are attached through connecting member 630, which preferably comprises an internal conduit for the routing of signal carrying wires between the first and second housing. As shown, connecting member does not impede the transmission of ultrasound waves between the transmitter and receiver. In a preferred embodiment, connecting member 630 is a hollow rod. The ultrasonic transmitter and receiver housed within the integrated device 600 connect to external electronic devices through connectors 650 that are preferably microdot connectors. In a preferred embodiment, the integrated probe includes at least one additional ultrasonic receiver, or more preferably an array of receivers, arranged at angles relative to the transmission axis for the detection of scattered waves.

It will be apparent to those skilled in the art that the dimensions of the integrated coaxial ultrasonic device may vary over a broad range to accommodate different measurement applications. In a preferred embodiment, the first and second housings have a diameter of approximately 0.5", the axial lengths of the first and second housings are 8" and 0.5", respectively, the axial length of the connecting member is approximately 2", and the diameter of the connecting member is approximately 0.1".

The aforementioned embodiment is well suited for ultrasonic particle size distribution measurements which do not require obtaining attenuation measurements at each discrete measurement frequency with the transmitter and receiver transducers at different distances apart. Accordingly, preferred embodiments of the present invention do not need to change the relative positioning of the transducer's transmitter and receiver. This avoids the requirements of any moving parts in the measurement technique. Furthermore, dynamic processes can change significantly during the time required to make measurements at multiple positions and result in unreliable measurements, problems which are avoided according to embodiments disclosed herein.

Figure 27:
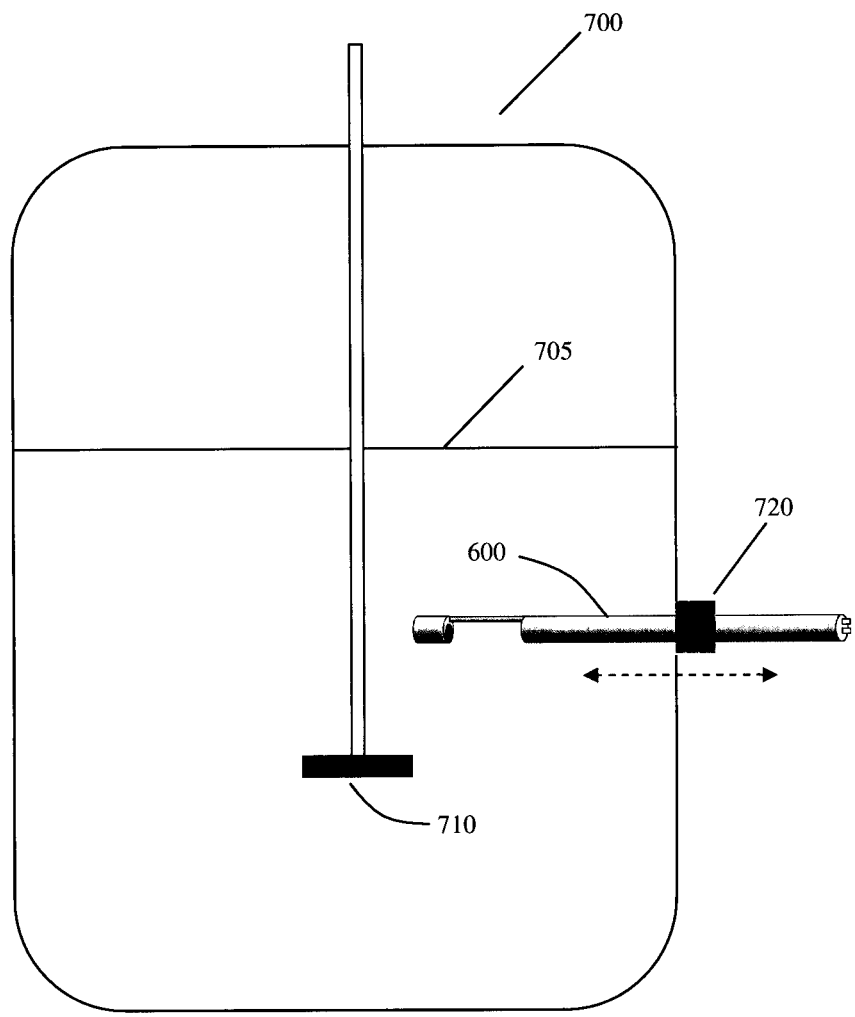
FIG. 27 illustrates the use of an integrated coaxial ultrasonic device in measuring a liquid contained within a vessel.
Figure 28:
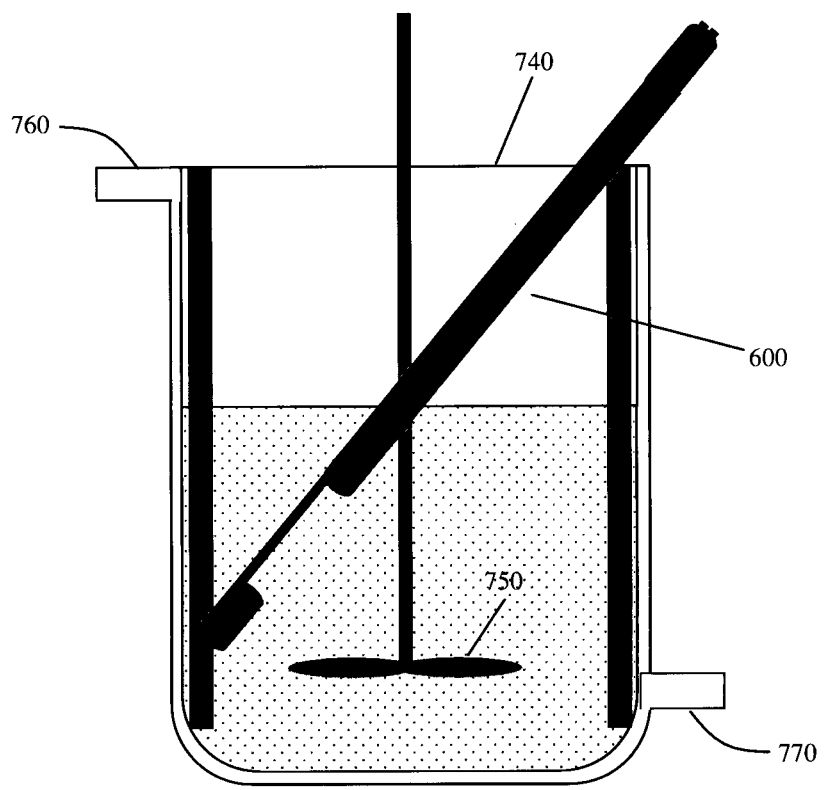
FIG. 28 illustrates an angled use of an integrated coaxial ultrasonic device within a jacketed glass reactor.

FIG. 27 illustrates the use of the aforementioned integrated coaxial ultrasonic device 600 for the measurement of a mixture 705 contained within a vessel 700. The integrated coaxial ultrasonic device 600 is preferably inserted into the vessel through a water-tight access port 720. In a preferred embodiment, the access port allows the insertion of the integrated coaxial ultrasonic device 600 at a variable internal depth. The vessel also preferably includes a mixing device such as impeller 710 to promote homogeneous dispersion of particles contained in the mixture. In another preferred embodiment, the integrated coaxial ultrasonic device 600 may be inserted into the vessel from above at an angle, in order to minimize the occurrence of particles settling on the transducer surface (as shown in FIG. 28).

SECTION 7

Application of Embodiments of the Invention for Online Monitoring of Crystal Growth Crystallizers are widely used in industrial processes for the production of chemicals and pharmaceutical. Crystallization processes are dynamic in nature and variations in crystal content and size are expected in real-time. Monitoring of these changes is essential to obtain/maintain desirable operating conditions, avoid complications in down stream processing and ensure product quality/conformity. Ideally, the particle size distribution (PSD) should be measured under the temperature and mother liquor conditions of the process vessel itself so that no artificial crystallization dynamics are introduced. This section investigates the modified model performance for online measurement of particle size distribution during the crystallization of paracetamol from paracetamol-isopropanol-water solution under natural cooling conditions.

Experiments were conducted to monitor change in PSD during batch crystallization of paracetamol from paracetamol-isopropanol-water (30 wt. % water, solute free) solution. As shown in FIG. 28, a jacketed glass reactor 740 of diameter 0.115 m and height 0.25 m was used for the crystallization experiment. It was equipped with a 45°-pitched blade impeller 750 of diameter 0.05 m and vortex formation was minimized using four stainless steel baffles. Water was circulated through the reactor jacket (though inlet 760 and outlet 770) to reduce the temperature of the saturated solution from 40° C. to 22° C. A custom designed broadband ultrasonic transmitter/receiver assembly 600 (as described in Section 6) with 3.4 MHz central frequency was used to generate and receive the ultrasonic pulse. The transducer is 0.025 m in diameter and the measurement path length was 0.05 m. The transducer was inserted at a 45° angle in the reactor to minimize particle settling on the sensor surface.

Figure 29:
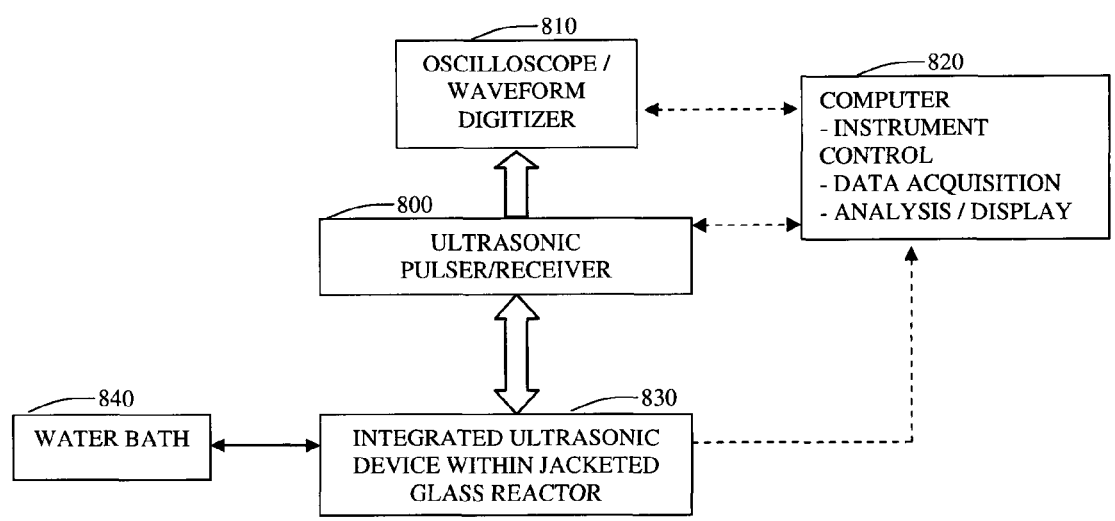
FIG. 29 shows a block diagram of the experimental apparatus for monitoring crystallization.

A block diagram of the experimental setup is shown in FIG. 29. The ultrasonic pulse was generated and its characteristics were controlled using the Fallon Ultrasonic® pulser/receiver unit 800 with a pulse repetition frequency of 1 kHz. A TDS 210 (Tektronix, Beaverton, Oreg., USA.) digital oscilloscope 810 was used to visualize, select and capture the pulse using a RS232 port of a computer 820. The solution temperature was measured using a thermocouple mounted on the transmitter/receiver device 830 and acquired using a RS232 port. Water was circulated with water bath 840. A graphical user interface was developed in Labview 8.0 to acquire the ultrasonic and temperature signals for analysis and display of results. The pulse processing and analysis is done using Fortran Dynamic Link Libraries (DLLs), which are accessed by the GUI. The calculated acoustic parameters include acoustic velocity, frequency spectrum (using Fast Fourier Transform), mean/peak pulse frequency, attenuation spectrum and total attenuation. A Fortran DLL is then used to calculate the PSD from the attenuation spectrum data using aforementioned attenuation spectroscopy embodiments. The integrated software was earlier tested extensively in concentrated suspensions (up to 30 vol. %) of glass beads with known mean sizes.

The model requires input of density and compressibility of the phases present at the operating temperature. The solubility data from Hojjati and Rohani[23] was used for the preparation of solutions of paracetamol, isopropanol and de-ionized water containing 30% water by weight (solute free) and 70% isopropanol. Paracetamol (4-Acetamidophenol) was obtained from Sigma Aldrich (St. Louis, Mo.) and isopropanol (99.9%) from Caledon Laboratories (Georgetown, ON, Canada). The solution compressibility was estimated from measured acoustic velocity and density of the solution using Equation 2.[24]

$$v_{sol} = \sqrt{\frac{1}{\rho_{sol}\kappa_{sol}}} \qquad (38)$$

Figure 30:
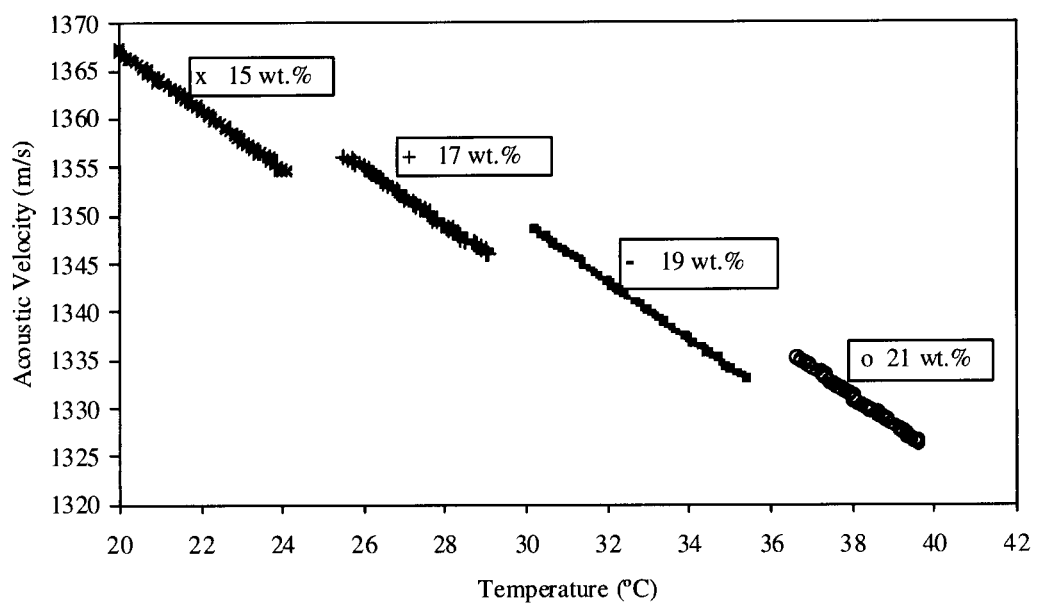
FIG. 30 plots the change in acoustic velocity with temperature for 15, 17, 19 and 21 wt. % of paracetamol in solution.

The solution density was measured for varying solute concentration and solution temperatures. These measurements were used to develop empirical equations for calculating the solution density for different solute concentrations and temperatures. The acoustic velocity was measured in under-saturated solutions of paracetamol in water (30 wt. %)-isopropanol. FIG. 30 shows the acoustic velocity measurements with 15, 17, 19 and 21 wt. % (paracetamol) between 20-24, 26-30, 31-34 and 36-40° C. respectively. The acoustic velocity showed a linear decrease with increase in solution temperature irrespective of the solute concentration. These measurements were used to develop linear least square fit equations between acoustic velocity and temperature. The equations were then used to estimate the acoustic velocity for various solute concentrations at 30° C. It was observed that the acoustic velocity showed an increase of ~6 m/s for every 2 wt. % increase in the paracetamol concentration. The validity of this approach for acoustic velocity prediction was tested by cooling saturated paracetamol solution from 40 to 30° C. The average cooling rate was about 1.5° C./minute and no nucleation was observed during this period. The measured acoustic velocity at 30° C. was 1395 m/s and showed good agreement with the predicted acoustic velocity (1394 m/s) using the above method. The predicted density and acoustic velocity using the semi-empirical methods discussed above were then used to estimate the solution compressibility using Equation 2.

To start a crystallization run, a saturated solution of paracetamol in isoprapanol-water (30 wt. % water) was prepared at 40° C. The saturated solution was then heated up to 45° C. and transferred to the jacketed glass reactor for crystallization. The cooling water temperature to jacket inlet was maintained at 20° C. using a water bath. At 40° C. the reference ultrasonic pulse was captured and stored for calculation of the attenuation spectrum after nucleation. The change in various pulse parameters and the calculated PSD were displayed every 7 seconds.

Figure 31:
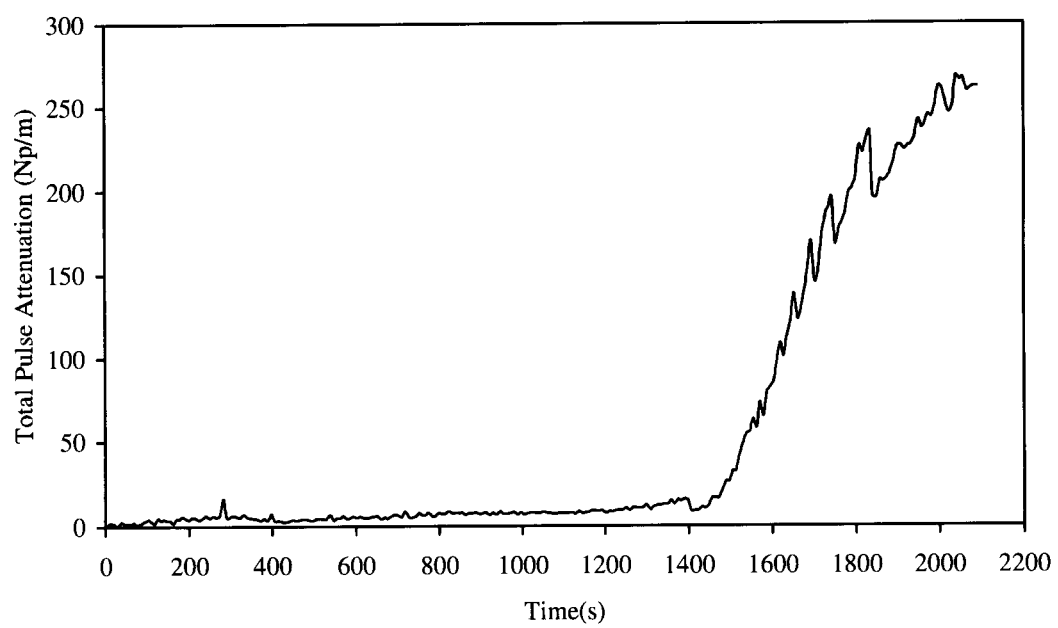
FIG. 31 plots the measured total attenuation during crystallization of paracetamol from paracetamol-isopropanol-water solution.
Figure 32:
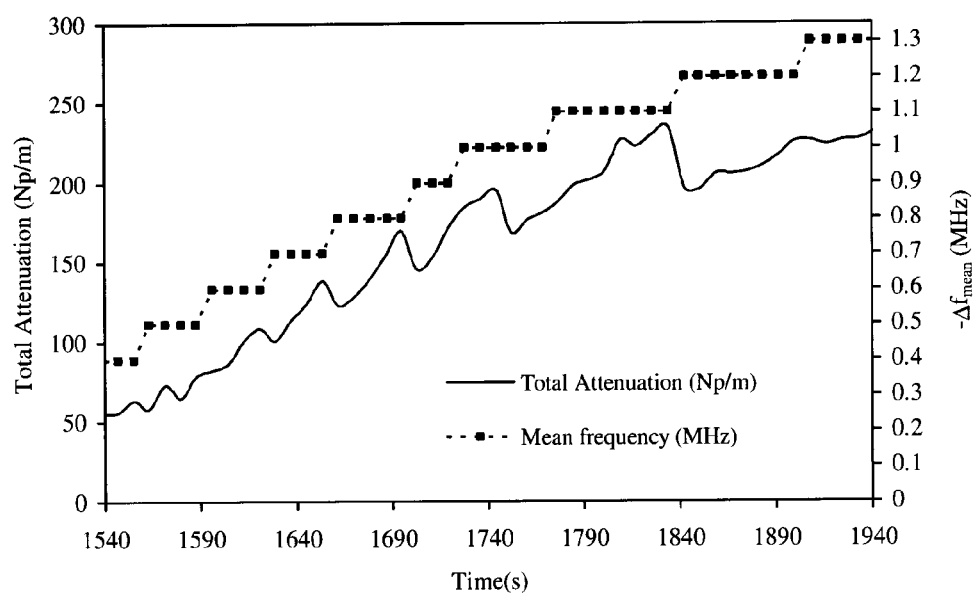
FIG. 32 shows the measured total attenuation and mean frequency during crystallization of paracetamol from paracetamol-isopropanol-water solution.

FIG. 31 shows the measured total pulse attenuation during crystallization of paracetamol. The gradual increase in attenuation up to ~1300 s is due to the increase in the intrinsic attenuation associated with the change in temperature of the paracetamol-isopropnaol-water solution. The figure also shows that the total attenuation shows a series of steep decrease as the crystallization progresses. These sudden drops in the total attenuation are associated with the shift in the power spectrum as its high frequency tail is attenuated. A change in the spectral composition of the ultrasonic pulse can be quantified using the mean frequency of the signal. FIG. 32 shows an expanded view of the irregularity in the total attenuation along with the measured decrease in mean frequency. The figure clearly illustrates that the decrease in mean frequency are closely associated with the sudden drops in the total attenuation.

Figure 33:
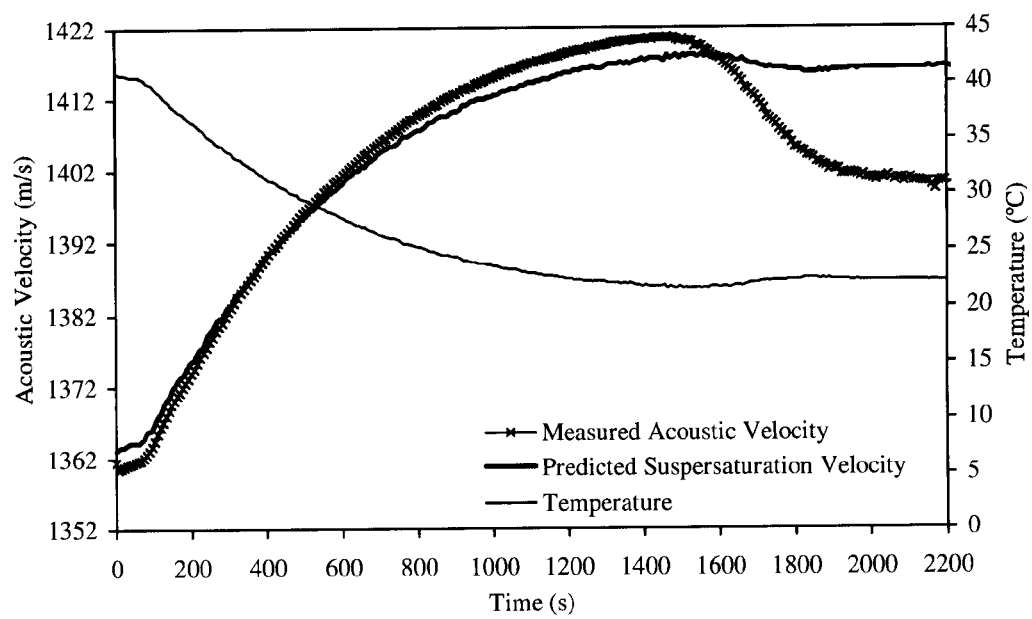
FIG. 33 plots the measured acoustic velocity and temperature change during crystallization of paracetamol from paracetamol-isopropanol-water solution.

FIG. 33 shows the change in measured acoustic velocity and temperature during crystallization of paracetamol. The temperature measurement was used to predict supersaturation acoustic velocity using the calibration technique and is also shown in the figure. The predicted supersaturation acoustic velocity is based on the total concentration of paracetamol at the measurement temperature and assumes no precipitation. The initial offset between measured and predicted acoustic velocity can be attributed to the system stabilization time (0-100 s) during which the cooling water circulation and mixing was started. The measured and predicted acoustic velocities showed good agreement up to 800 s followed by a gradual deviation of about 2 m/s till 1200 s. The difference in measured and calculated acoustic velocity remained constant from 1200 s to 1450 s. Thereafter the trend in measured velocity deviates significantly from the predicted supersaturation acoustic velocity and is due to the precipitation and growth of particles. The gradual deviation in acoustic velocity from 800 s to 1200 s when no precipitation was observed appears to be due to the empirical methodology in predicting acoustic velocity at high supersaturation levels. However, this error was less than 2 m/s and can be eliminated by increasing the data set used for the empirical model development.

Visual observation showed that small concentrations of particles were precipitated at ~1200 s indicating the onset of nucleation and hence a decrease in supersaturation. The acoustic velocity is expected to decrease with decrease in the supersaturation level, unlike the measurements obtained in FIG. 33. Literature shows that acoustic velocity increases with increase in particles concentration and decreases with increase in particle size[25,26,22]. Furthermore, the rate of increase in acoustic velocity with concentration also decreases with increase in particle size[27,19]. The higher measured acoustic velocity (~4 m/s) during nucleation can be attributed to the increase in particles concentration and its effect supersedes the effect of decrease in the supersaturation levels. The decrease in acoustic velocity measurements above 1450 s indicates a rapid growth in particle size. Hence, a comparison between the measured and predicted supersaturation velocities can be used to identify the region of nucleation as well as the region of rapid particle size growth.

Figure 34:
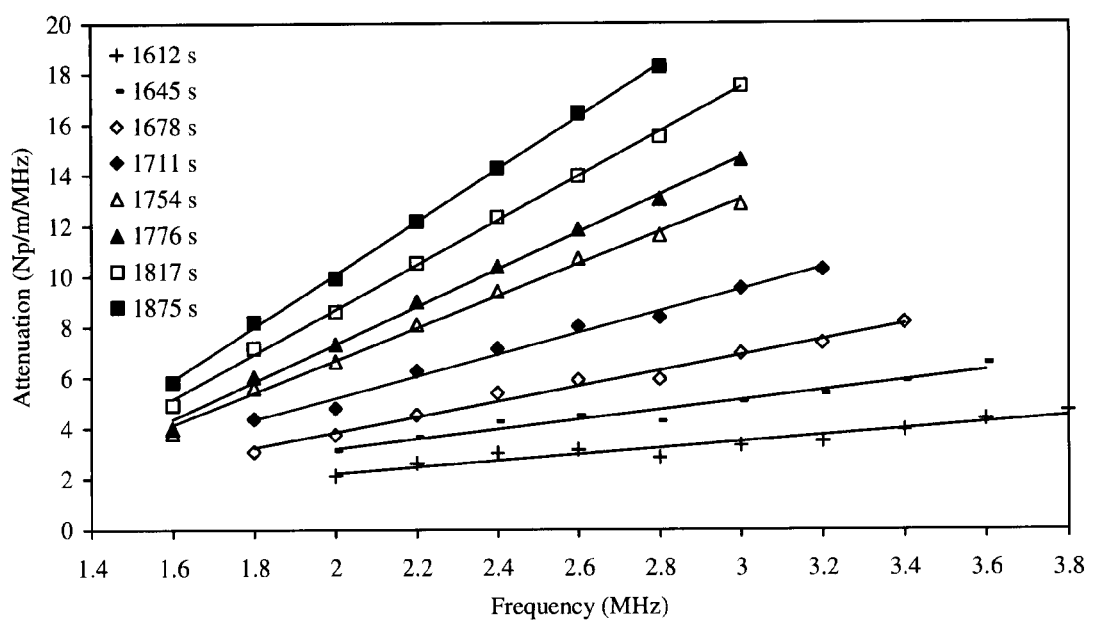
FIG. 34 plots the measured attenuation spectra during crystallization of paracetamol from 1612-1875 s.
Figure 35:
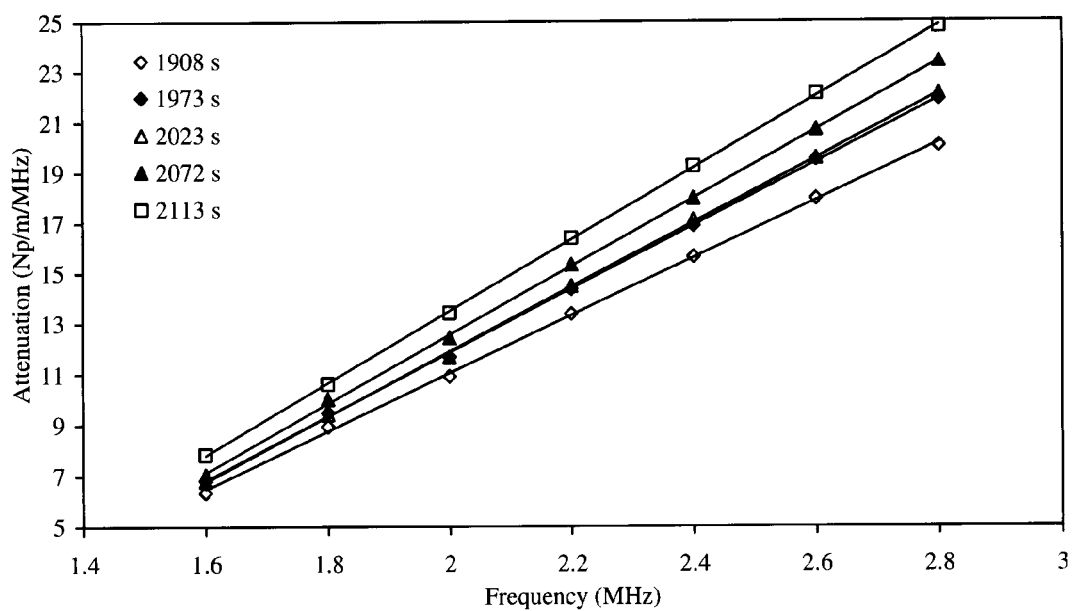
FIG. 35 plots the measured attenuation spectra during crystallization of paracetamol from 1908-2113 s.

FIGS. 34 and 35 show the measured attenuation spectra obtained at different times during the crystallization of paracetamol. Normalized attenuation (attenuation/frequency) is plotted in the figures to show the change in attenuation per unit frequency. The loss in higher frequencies contained in the ultrasonic pulse due to increase in particle size and concentration (with increase in crystallization time) is evident from the measured spectrums at 1612 s and 1875 s in FIG. 34. FIG. 35 shows that from 1908 s to 2113 s the spectral consistency remains unchanged.

Figure 36:
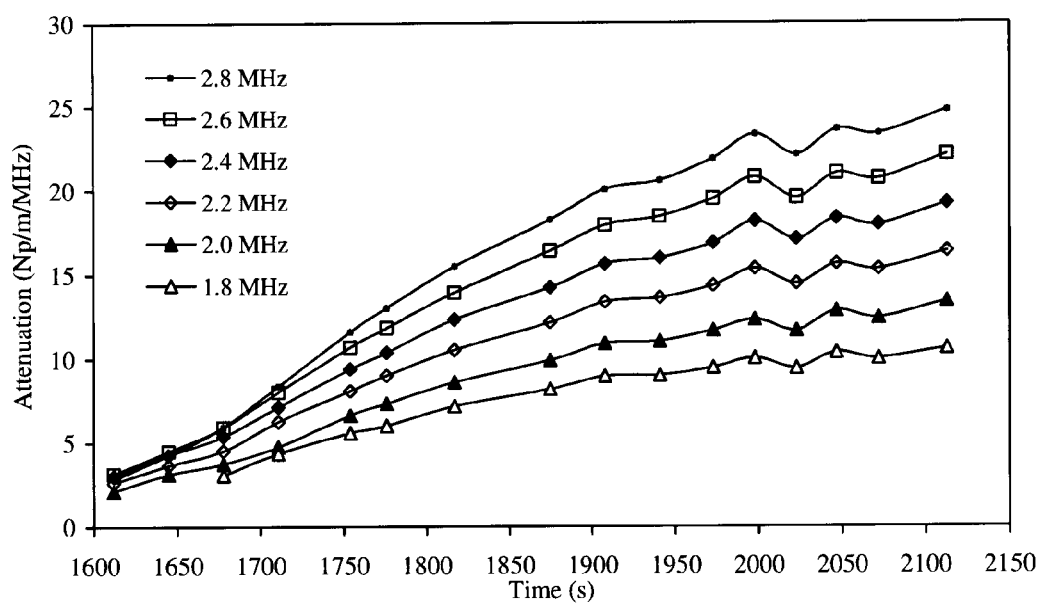
FIG. 36 shows the change in measured attenuation at each frequency over a span of 1 MHz (1.8 to 2.8 MHz) during crystallization of paracetamol.

The measured attenuation (Np/m/MHz) at any given time during crystallization showed a linear change with increase in frequency. Linear least-square fits to the various attenuation spectra showed an increase in slope with increase in crystallization time. The attenuation spectrum slope at any given time is dependent on the PSD and total concentration of particles. The quality of the spectral data is extremely good as shown by the fit parameter ('$R^2$' values ~0.99) during the entire duration of crystallization. FIG. 36 shows the change in measured attenuation at each frequency over a span of 1 MHz (1.8 to 2.8 MHz) with increase in crystallization time. It can be seen that the trend between two subsequent measurement times was similar for all frequencies and indicates that the spectral integrity was maintained during crystallization.

FIGS. 34, 35 and 36 also show that frequency increment of 0.2 MHz gives a good resolution in the measured attenuation. The deconvolution algorithm (discussed in Section 5 above) uses the total attenuation (Np/m) measured at each frequency for PSD calculations. The total attenuation varies from ~14 Np/m (1612 s) to ~45 Np/m (2113 s) over the average spectral width of 1.2 MHz. Hence, a single broadband transducer should be sufficient for measuring the PSD as long as the spectral quality is good (FIGS. 34, 35) and the theoretical attenuation model is able to operate in dense suspensions.

Figure 37:
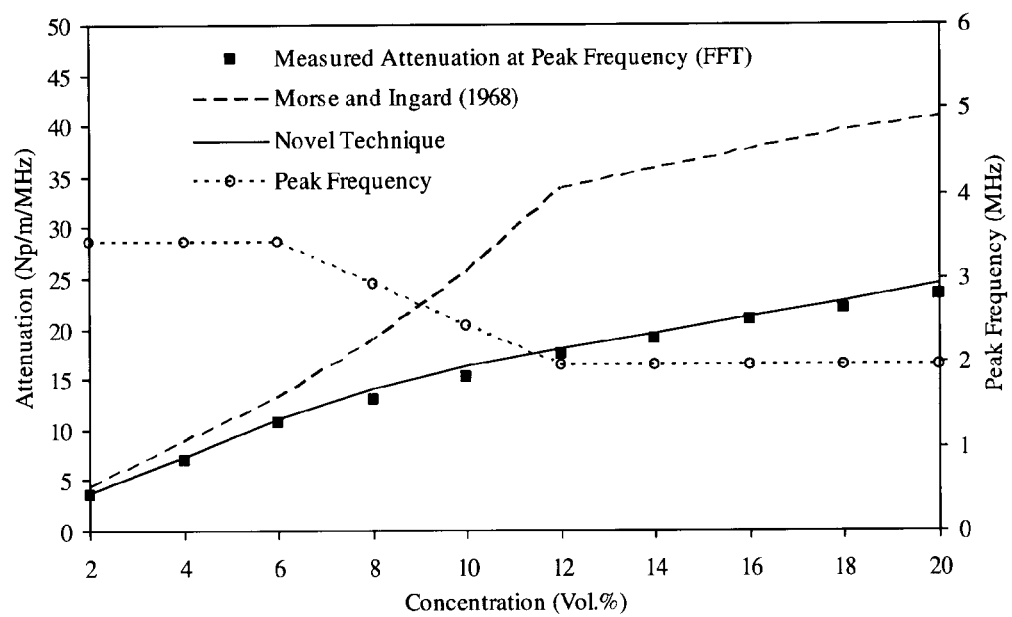
FIG. 37 provides a comparison of predicted attenuations using the original Morse and Ingard, (1968) model and the modified model at peak frequency for 114-μm glass beads with measured attenuation.

FIG. 37 shows the measured attenuation at the peak frequency for 114-μm glass particles from 2 to 20 vol. % concentration. In the intermediate wave regime the attenuation increases with increase in frequency. For broadband ultrasonic signals this can result in a shift of the peak frequency to a lower value as shown in FIG. 37. The measured peak frequency obtained from the FFT of the ultrasonic signal decreased from 3.4 MHz at 6 vol. % to 2 MHz at 12 vol. %. As expected the measured attenuation values also show a decrease in the rate of change in attenuation with drop in the peak frequency. Theoretical attenuation using the original[18] as well as the modified model according to embodiments of the invention were calculated at the peak frequency using offline PSD from laser diffraction (Malvern Mastersizer®). Good agreement between measured and calculated[18] attenuation was observed up to 4 vol. % concentration. However, unlike measured attenuation the calculated attenuation showed an increase in the attenuation rate with decrease in peak frequency. This observation clearly indicates that the model predictions rapidly deteriorate under dense conditions. In contrast, calculated attenuation values using the modifications of the Morse and Ingard[18] model according to embodiments of the present invention show good agreement with measured attenuation even at high concentrations.

Figure 38:
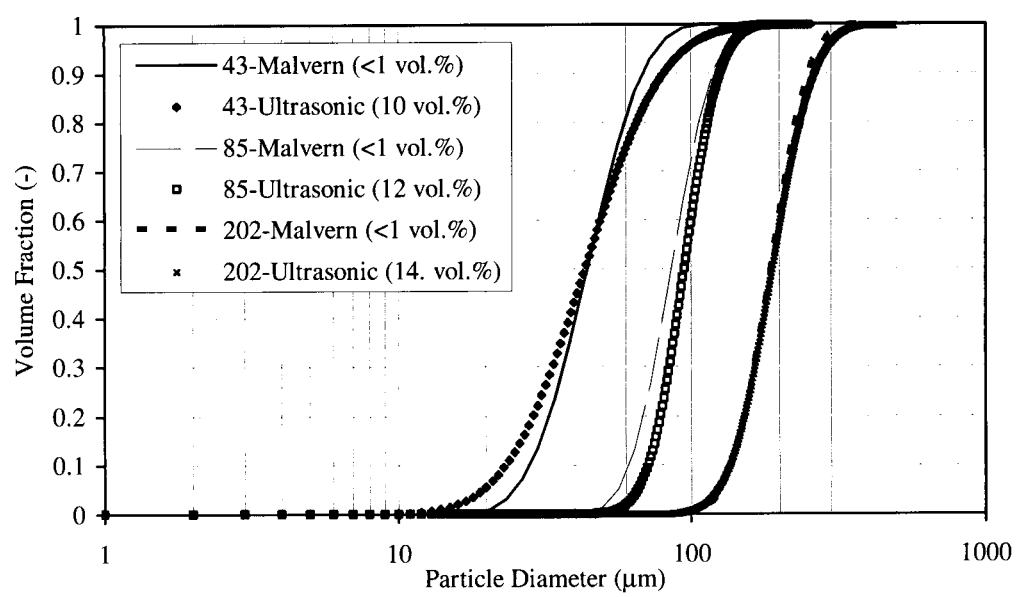
FIG. 38 Comparison of PSDs (46, 76, 202-μm) measured using modified attenuation spectroscopy technique at 10, 12 and 14 vol. %, respectively with offline laser diffraction (<1 vol. %) results (Malvern Mastersizer®) for glass beads suspended in water.

FIG. 38 shows a comparison of the PSDs measured using the novel ultrasonic attenuation spectroscopy technique disclosed herein and laser diffraction (Malvern Mastersizer®) for de-ionized (DI) water-glassbead suspension. The PSD measured using ultrasound was at 10, 12 and 14 vol. % concentration for 46, 76 and 202-μm particles, respectively as opposed to less than 1 vol. % for the Malvern Mastersizer®. The predicted PSDs in dense suspensions using ultrasonic attenuation spectroscopy showed a good agreement with the diluted sample measurements by laser diffraction. The model calculates the attenuation caused due to a single particle and the total attenuation is obtained using the superposition principle. Hence, for polydispersed particles the total attenuation can be calculated using Equation 39, where '$\alpha_{i,j}$' is the calculated attenuation according to the previously disclosed embodiments of the invention at frequency 'j' of the '$i^{th}$' particle size with concentration '$\Phi_i$'.

$$\alpha_T = \sum_{f=j}^{m} \sum_{r=i}^{n} \Phi_i \alpha_{i,j} \qquad (39)$$

The particle size distribution function can be separated from the total concentration by using the particle volume based size distribution instead of the total volume based size distribution. Hence, Equation 6 can be simplified and re-written as shown in Equation 7, which is a well accepted methodology for PSD representation.

$$\alpha_T = \Phi \sum_{f=j}^{m} \sum_{r=i}^{n} \phi_i \alpha_{i,j} \qquad (40)$$

In the above equation '$\phi_i$' represents the particle volume based concentration of '$i^{th}$' size and is optimized to obtain the best fit PSD. The method presented in this study assumes that the volume independent concentration of the various particle sizes follow a log-normal distribution. Hence, optimizing the log-normal distribution parameters ($\mu$, $\sigma$) to minimize the difference between measured and calculated attenuations will yield the best fit PSD.

The new model was used to measure the PSD from spectral attenuation measurements during crystallization of paracetamol. The deconvolution algorithm obtains the initial approximation of the total concentration '$\Phi$' from the solubility curve data of paracetamol in isopropanol-water (30 wt. %) solution[23]. During crystallization the solution is generally super saturated and the actual particles concentration will be less than the concentration obtained from the solubility data. This method ensures in setting the maximum limit of total concentration up to which the algorithm attempts to find the best fit PSD.

Figure 39:
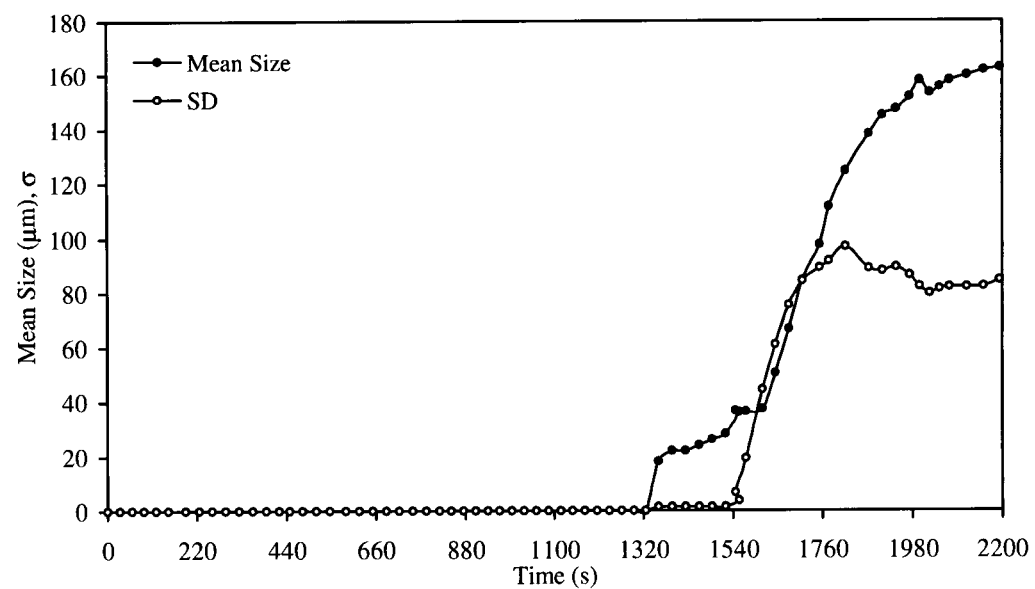
FIG. 39 plots online measurements of mean size and standard deviation during paracetamol crystallization using the modified ultrasonic attenuation technique.

FIG. 39 shows the change in mean particle size and standard deviation of the best fit log-normal PSD during crystallization of paracetamol. The PSD measurement technique reports the first PSD at ~1320 s. This is followed by a gradual increase in mean particle size up to 1540 s and a narrow distribution was predicted. From 1540 s to 1817 s the measured PSD showed a rapid increase in mean particle size as well as the standard deviation. From 1817 s-1990s the mean particle size continued to increase whereas a slight narrowing of the distribution was observed. Thereafter till the end of the experiment the distribution width remain fairly constant and the mean size showed a slight increase.

Visual observation revealed that precipitation started at about 1200 s, however the first PSD measurements were obtained at 1320 s. The primary reason for this blind zone in the measured PSD could be attributed to the attenuation caused by the change in the solution temperature. Capturing the reference pulse close to the beginning of nucleation will be useful in avoiding the effects caused due the intrinsic attenuation associated with the solution temperature. During the initial phase of crystallization the concentration as well as particle size is low and their attenuation can easily be shadowed by the intrinsic attenuation. The relatively low standard deviation up to 1540 s could also be caused due to the interference of the intrinsic attenuation. However, with increase in concentration the particle associated attenuation becomes significantly greater than the intrinsic attenuation and the full PSD measurements were obtained.

Figure 40:
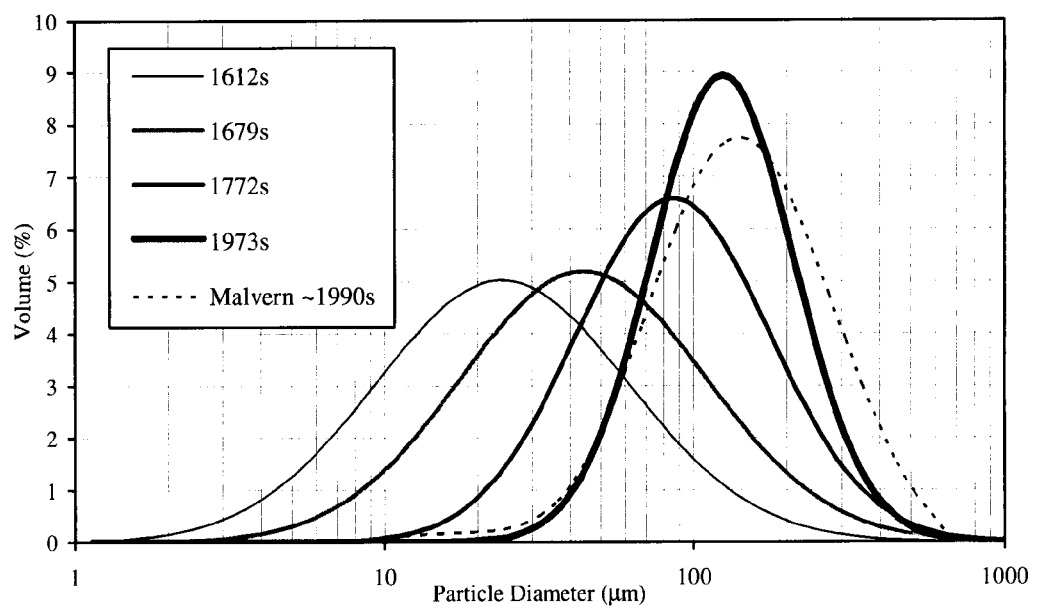
FIG. 40 plots online measurements of PSD using the modified ultrasonic attenuation technique at various times during crystallization. The offline measurement from Malvern Mastersizer® is also shown for comparison with the online ultrasonic PSD at the sample retrieval time.

A sample of the crystals was harvested at about 1990s for offline PSD analysis using laser diffraction. The retrieved crystal samples were filtered and subsequently washed using saturated paracetamol-water solution to terminate crystallization. The washed sample was then analyzed using laser diffraction (Malvern Mastersizer®) and the measured PSD is shown in FIG. 40 along with the online PSD results from ultrasonic attenuation spectroscopy at various measurement times. The figure shows that the PSD obtained using online ultrasonic technique (dense suspension) is in good agreement with the offline laser diffraction analysis which operates at concentrations less than 1 vol. %. The deviations in the two PSDs are most likely due to the sample retrieval and preparation process itself.

The applicability of a novel ultrasonic spectroscopy based PSD measurement technique in the intermediate wave regime was demonstrated during crystallization of paracetamol from paracetamol-isopropanol-water solution. The measurements were made in situ using a single broadband transducer. For estimating the liquid properties during crystallization, an acoustic velocity based method using under saturated paracetamol-isopropanol-water solution was developed. The PSD determined using the ultrasonic spectroscopy model showed good agreement with laser diffraction analysis of a sample retrieved from the crystallizer. The new technique shows promising potential for online measurement of PSD in dense and opaque suspensions of large particles.

SECTION 8

Embodiments of the Invention Involving Process Control

As discussed above, the preceding embodiments of the invention provide distinct advantages over prior art methods, particularly when measurements are made in the intermediate wave propagation regime. Experiments performed to date by the present inventors have shown that ultrasonic-based methods according to the invention can determine particle size distribution in suspensions of about 1 µm to about 1000 µm particles and wide range of concentrations (from about 1 to 30 vol. % or more). Most advantageously, the ultrasonic-based methods disclosed herein for the monitoring, determination and/or detection of particle size distribution may be applied to optically opaque and high suspension density where laser based method is unsuccessful.

The inventors have also found that embodiments of the present invention for the determination of particle size distribution typically provide greater accuracy than laser-based method, since the method of the present invention is based on the measurement of a more representative sample compared to laser based method. The laser based method only measures particles near the probe window (FBRM). Whereas, ultrasound has a penetration depth of 50 mm or more in suspensions of 20 vol. % and 25 mm or more in suspensions >30 vol. %. Furthermore, embodiments of the present invention that measures the volume weighted particle size distribution often provide superior results to compared to chord length distribution by the laser based method (FBRM). Additionally, unlike other prior art methods, the present embodiments are cost effective due to their model-based nature and do not require experimental calibration charts of attenuation coefficients with respect to particle size at different frequencies. Existing ultrasonic techniques applicable to large particles require such calibration charts over a wide range of frequencies for all particle size fractions (20 KHz-20 MHz or 1 MHz to 100 MHz). A further benefit of embodiments of the present invention is the use of a smaller set of ultrasonic frequencies, such as for example between 1 to 10 MHz, which makes it more efficient as significantly less computing power and time are required to perform the deconvolution algorithm. Furthermore, limiting the number of frequencies provides significant cost benefits due to reduced number of transducers and channels for measurement.

In one preferred embodiment, measurements of the peak attenuation frequency may be used to monitor a process involving a change in a particle size distribution of a mixture. An ultrasonic transducer system is employed to measure the attenuation spectrum of an ultrasonic pulse through a mixture. Preferably, such a method may be adapted to utilize the shift in frequency spectrum to detect particle size growth above a critical limit. Accordingly, such a method may include a means to generate warning signals/feedback for process control, such as an audible alarm or directly controlling process parameters such as mixing and/or temperature.

As demonstrated above in Section 2, broadband ultrasonic pulses show, for a specific ultrasonic frequency, a shift in the mean/peak frequency when particles above a specific size are present. Monitoring of the mean/peak frequency provides a natural alarm system for particle growth build-up when there is a shift in its value.

The inventors discovered that the frequency shift occurs at wavenumbers above about 0.3. As defined before, wavenumber is the ratio of particle size and ultrasonic frequency. Hence, an appropriate frequency can be selected (for example, by empirical methods), which results in a wavenumber above about 0.3 when a pre-selected particle size is reached in the medium. For particles below the critical size no change in the mean/peak frequency will be obtained. A shift in the mean/peak frequency will generate a warning alarm indicating particle build-up above the critical size.

Figure 41:
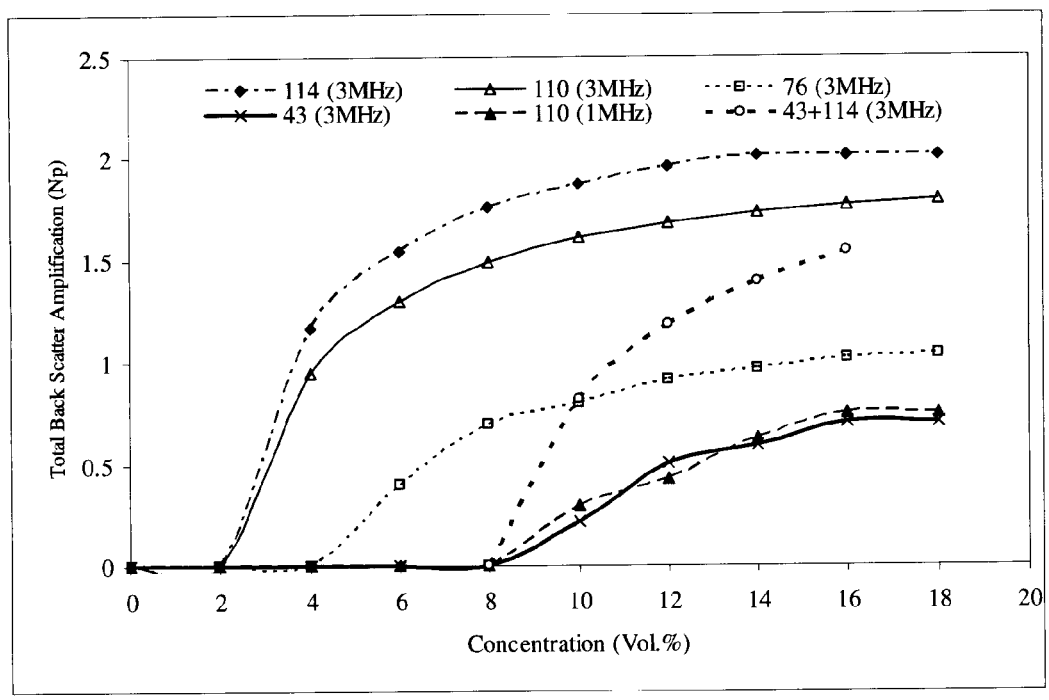
FIG. 41 shows the backscattered signal for various sized glass beads at different frequencies.

In a further aspect yet of the present invention is a method for estimating the particle shape within a particulate mixture. As shown in FIG. 41, the measurement of back scattered ultrasound signals provides information on particle size concentration and growth in particle size. Back scattered detection is a function of the wave number, which is a ratio of particle circumference and wavelength. For example, the wave number of a 110-µm particle at 1 MHz (0.25) is similar to that of 34-µm particle at 3 MHz (0.22) and produces a similar back scattered signal. Hence, appropriate frequency selection based on the critical particle size provides for the monitoring of particle size build-up.

Since back scattered signals are also shape dependent, in another aspect, the present invention provides a new method to provide information on the extent of deviation from spherical particle shape when used in conjunction with the measurement of transmitted signals. According to this aspect, the particle size distribution (PSD) is measured according to the previously disclosed embodiments of the invention. The calculated PSD can then be used with a scattering model to predict a spectrum at a secondary angle, which is an angle other than through the transmission direction. In preferred embodiments, the predicted spectrum may be any one of a power spectrum, amplitude spectrum, and attenuation spectrum. This same secondary angle can then be used to measure the corresponding spectrum of the scattered wave. In a preferred embodiment, the secondary angle could be that of the back scattered wave, which could be obtained when the same transducer acts as an emitter and receiver. In yet another embodiment, two or more secondary angles may be measured using an array of detectors, providing more than one single comparison for the determination of the appropriate shape.

The measured spectrum is compared with the calculated spectrum in order to obtain a difference factor. In a preferred embodiment, a weight factor may be employed as disclosed in section 4 for the suppression of noise. This difference factor can then be compared to a library of difference factors generated by particles of various shape factors. Such a library may be generated by one of many methods, for example, by simulations and by empirical measurement methods. Error minimization is conducted between the measured difference factor and those obtained from the library to identify the shape factor of particles in the medium.

In a related embodiment, the shape may be determined by varying the assumed shape from an initially assumed shape, and comparing the measured spectrum with the calculated spectrum. An improved estimate for the shape of the particles is obtained by selecting a shape that minimizes an error between the measured and calculated spectra.

In yet another embodiment of the invention, a method is provided for determining the onset and/or completion of dissolution based on ultrasonic measurements. While prior art methods using attenuation or acoustic velocity have been developed to monitor and/or measure properties of suspensions and solutions, they require extensive customization and are often impractical and/or expensive.

The present embodiment utilizes total attenuation, spectral attenuation and acoustic velocity measurements to monitor the dissolution process. The embodiment provides an improved method to detect when a dissolution process is complete and/or nearing completion. The integrated use of the ultrasonic parameters ensures robust and reliable performance by eliminating ambiguity caused due to factors other than dissolution on the measurements.

Preferably, the method according to the present embodiment of the invention is performed using an integrated assembly of the transmitting and receiving sensors, as illustrated in FIGS. 26-28. As previously discussed, the assembly can be inserted horizontally or at an angle in the process vessel. The separation between the transmitter and the receiver is preferably pre-selected based on the type of application. A larger separation ensures a more representative sample, however the initial size and concentration of the powders may induce excessive attenuation.

In a first step of the method, the time-dependent transmission of an ultrasonic pulse is measured. From this measurement, the time-of-flight of the ultrasonic pulse is determined. The acoustic velocity is then calculated from the measured flight-time of the pulse using Equation 41.

$$v = \frac{d}{t_{pulse}} \tag{41}$$

The total attenuation and attenuation spectrum are then obtained, preferably based on the aforementioned transmission measurement of the ultrasonic pulse, and also a transmission measurement of an ultrasonic pulse in a reference fluid that is preferably substantially free of particles. In one embodiment, spectral attenuation may be calculated from the Fast Fourier Transform of the received pulse using Equation 42 and the total attenuation is the sum of attenuations at each frequency component:

$$\alpha_f = -\frac{1}{d}\ln\left(\frac{A_{i,f}}{A_{R,f}}\right) \tag{42}$$

In the above equation 'd' is the distance between transmitter and receiver, '$t_{pulse}$' is the measured flight-time of the through transmitted pulse and 'v' is the acoustic velocity. $A_{R,f}$ is the amplitude in the reference fluid and $A_i$ is the measured amplitude during dissolution.

Acoustic velocity is affected by the operating temperature, physical properties of a medium as well as suspended solids. Literature shows that solids concentration can be monitored using independent acoustic velocity measurements in insoluble suspensions[28,29]. Acoustic velocity has also been used to measure the effect of dissolved solute concentration in solutions[30]. It generally decreases with decrease in solids concentration; however the effect of dissolved solute is dependent on the properties of the material. Hence, acoustic velocity, when measured alone, can cause ambiguity as the effect of decrease in solids can be masked by the effect of increase in dissolved solute concentration. Furthermore, changes in operating temperature due to process variables such as heat of solution will also affect the measurements.

Similar to acoustic velocity, spectral attenuation is also affected by the physical properties of the solids and the medium. However, the impact of temperature change on spectral attenuation is significantly less as compared to acoustic velocity over an ultrasonic frequency bandwidth of 1-2 MHz. Attenuation due to the medium properties (known as intrinsic attenuation) is also significantly lower compared to that of the solids and its frequency dependence is fairly small. Although ultrasonic attenuation spectroscopy is used to measure particle size distribution and concentration in precipitating systems, the reverse process can be unreliable in the region where solids attenuation becomes comparable to the intrinsic attenuation of the solution. This stage will invariably occur as the amount of un-dissolved solutes continues to decrease.

Figure 42:
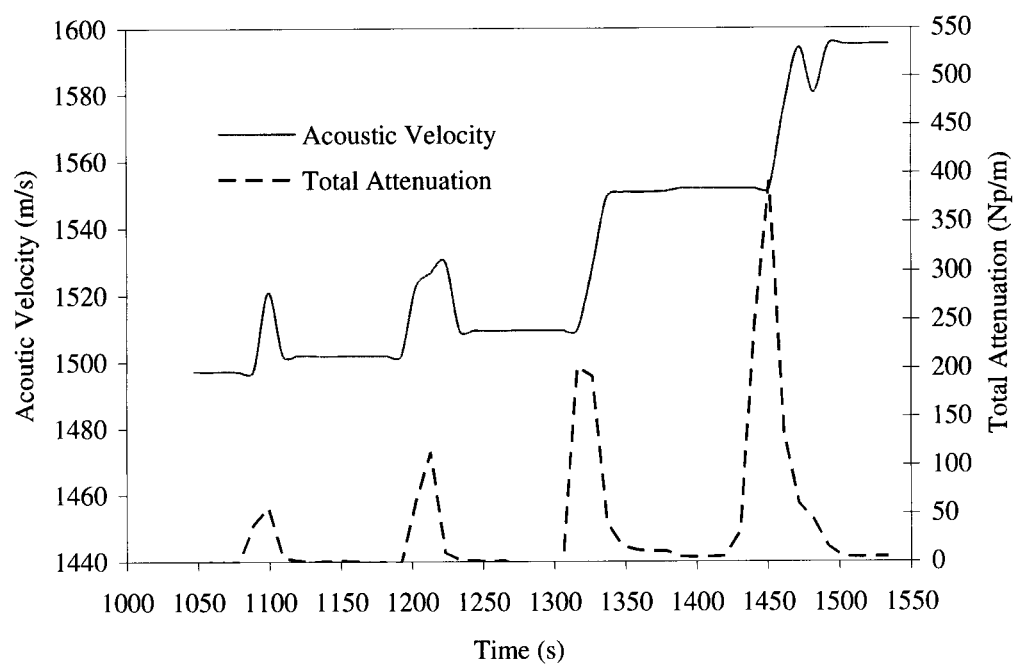
FIG. 42 plots acoustic velocity and total attenuation measurements during dissolution of sugar in water.

FIG. 42 shows the acoustic velocity and total attenuation measurements during dissolution of sugar in water. The step change in acoustic velocity and the peaks in total attenuation along the time axis correspond to sugar increments of 2, 3, 10 and 10 wt %. It is evident from the plot that acoustic velocity measurements tend to become constant after complete dissolution was achieved. Since attenuation is primarily affected by the concentration and size of the sugar crystals, it decreases and becomes constant once all the sugar has dissolved. However, the graphs indicate that attenuation does not reach zero values even after complete dissolution due to the increase in intrinsic attenuation of the sugar solution. These observations show that either acoustic velocity or attenuation measurement can be used for monitoring sugar dissolution. However, any change in solution temperature will change the acoustic velocity as well as the total intrinsic attenuation and may lead to ambiguity in detecting the end point of dissolution.

Figure 43:
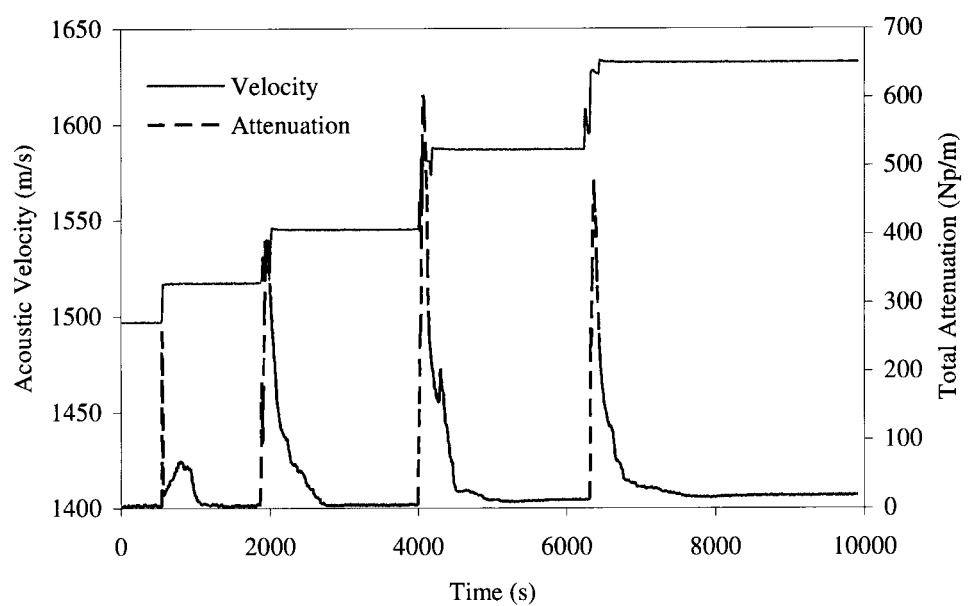
FIG. 43 shows acoustic velocity and total attenuation measurements during dissolution of salt in water FIG. 44 plots acoustic velocity and temperature measurements during dissolution of paracetamol in isopropanol-water solvent.

FIG. 43 shows the acoustic velocity and total attenuation measurements during dissolution of salt in water. The step change in acoustic velocity and the peaks in total attenuation along the time axis correspond to salt increments of 2, 3, 4 and 4 wt %. It is evident from the plot that acoustic velocity measurements tend to become constant before the attenuation values. Acoustic velocity decreases with decrease in solid salt concentration and increases with increase in dissolved salt content. This opposing effect appears to cause a steady state in acoustic velocity measurements much before all the solids have gone in to the solution (also confirmed visually). Hence, acoustic velocity measurements alone give an incorrect indication of complete dissolution. Similar to sugar dissolution, attenuation attains low values and becomes constant only after all the salt has dissolved. However, due to increase in the intrinsic attenuation of the solution, the total attenuation values do not achieve near zero values. Furthermore, this intrinsic attenuation becomes higher in magnitude with increase in the total concentration to 25 wt. %.

Figure 44:
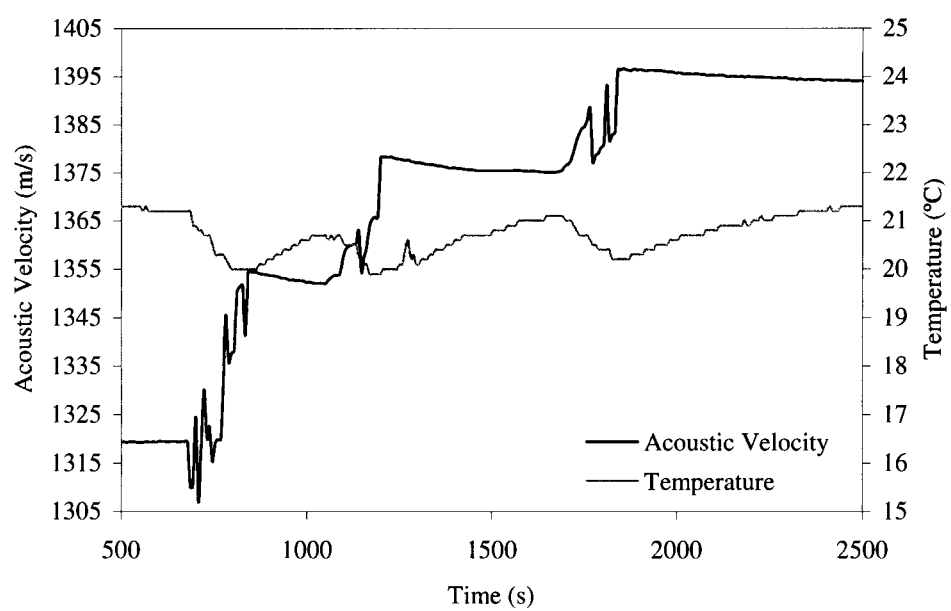
Figure 45:
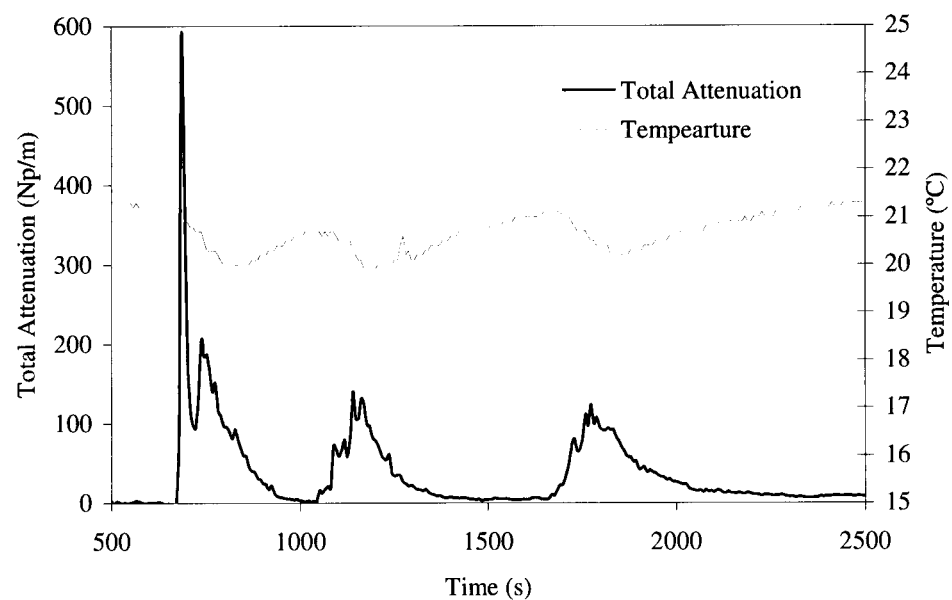
FIG. 45 shows the change in total attenuation and solution temperature during dissolution of paracetamol in isopropanol-water solvent.

FIG. 44 shows acoustic velocity and temperature measurements during dissolution of paracetamol in water+isopropanol solvent. The step changes indicate 40 g of paraceamol increments added to the solvent. This figure clearly shows that temperature fluctuations can significantly hinder the ability of acoustic velocity to indicate complete dissolution. Similar to the observations for salt and sugar, FIG. 45 shows that change in total attenuation is less affected by the solution temperature and is better suited to monitor dissolution. However, change in intrinsic attenuation of the solution can cause ambiguity in the detection of complete dissolution.

The above examples show that integrated use of acoustic velocity and attenuation can be used to detect complete dissolution with improved certainty when compared to methods involving only measurements of acoustic velocity. However, the intrinsic attenuation in solutions close to saturation may have a very high attenuation component. Hence, due to this attenuation and possible changes in solution temperature, it is required to monitor the ultrasonic parameters over larger time durations. This is to ensure that the solution has actually achieved steady state and all the solute has gone in to solution.

Figure 46:
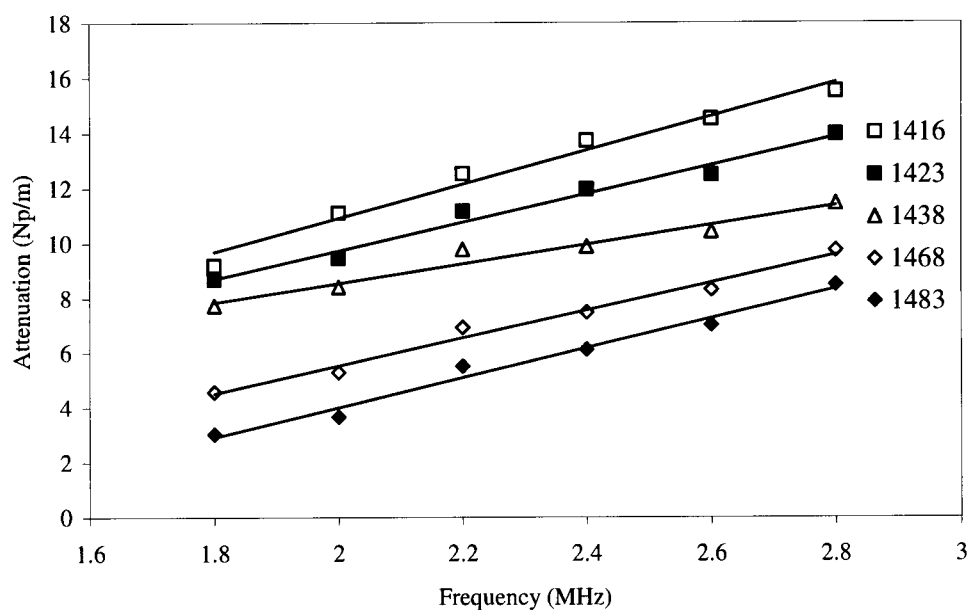
FIG. 46 plots spectral attenuation measurements with partial dissolution during dissolution of paracetamol in isopropanol-water solvent.

This problem can be resolved by using spectral attenuation instead of the total attenuation. Besides total particles concentration the spectral attenuation shows a very strong relationship with particle size. The attenuation contrast introduced due to the presence of particles can be clearly seen in FIG. 46. During this phase, the particle size distribution of the solids can additionally be obtained to provide further confirmation of the dissolution process using embodiments of the invention disclosed above.

Figure 47:
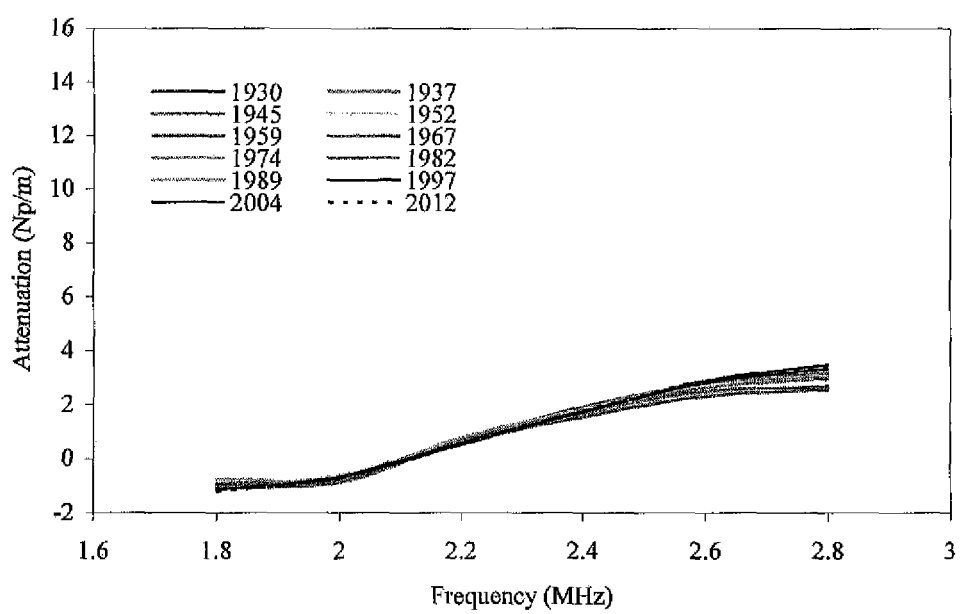
FIG. 47 plots spectral attenuation measurements after complete dissolution during dissolution of paracetamol in isopropanol-water solvent. The residual attenuation indicates is due to intrinsic losses of the solution.
Figure 48:
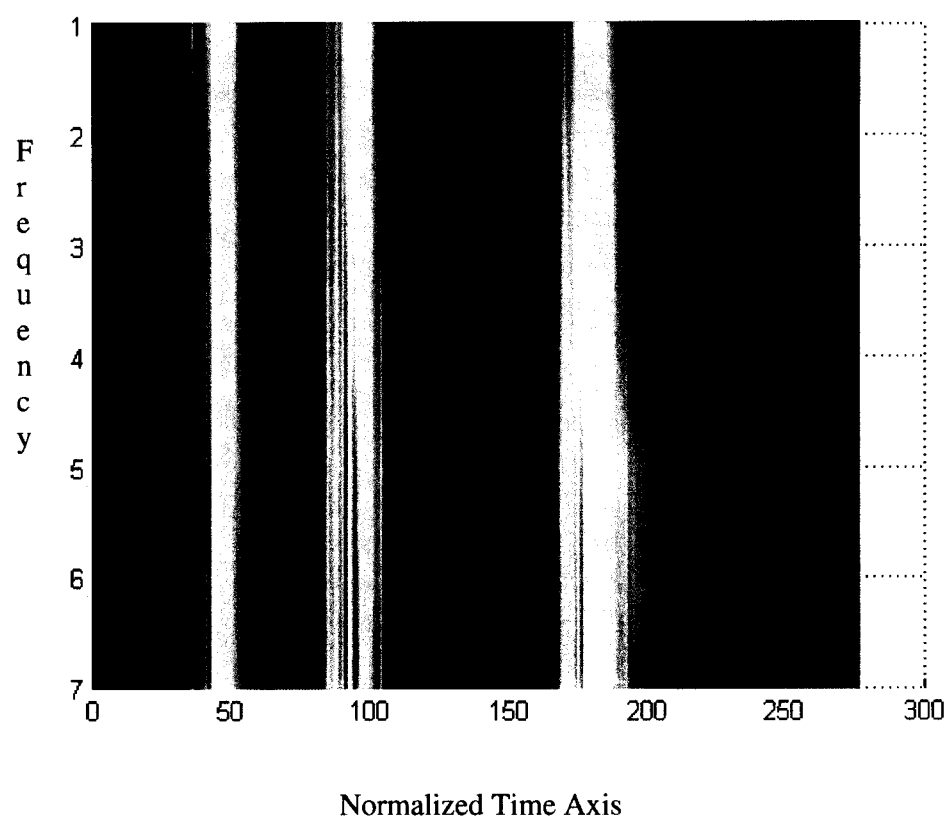
FIG. 48 shows a map plot showing dissolution of paracetamol in isopropanol-water solvent. The frequency axis corresponds to 1.8 to 3.2 MHz in increments of 0.2 MHz. Black indicates solids free solution.

FIG. 47 shows the spectral attenuation plots when only intrinsic losses are present in the solution. The effect of temperature fluctuations on attenuation at the various frequency components is small when considering a relatively narrow bandwidth (~1 MHz). FIG. 48 is a 2-D surface plot showing the dissolution process using spectral attenuation. Hence, spectral attenuation should be used along with total attenuation, acoustic velocity and preferably temperature measurements to detect complete dissolution.

Figure 49:
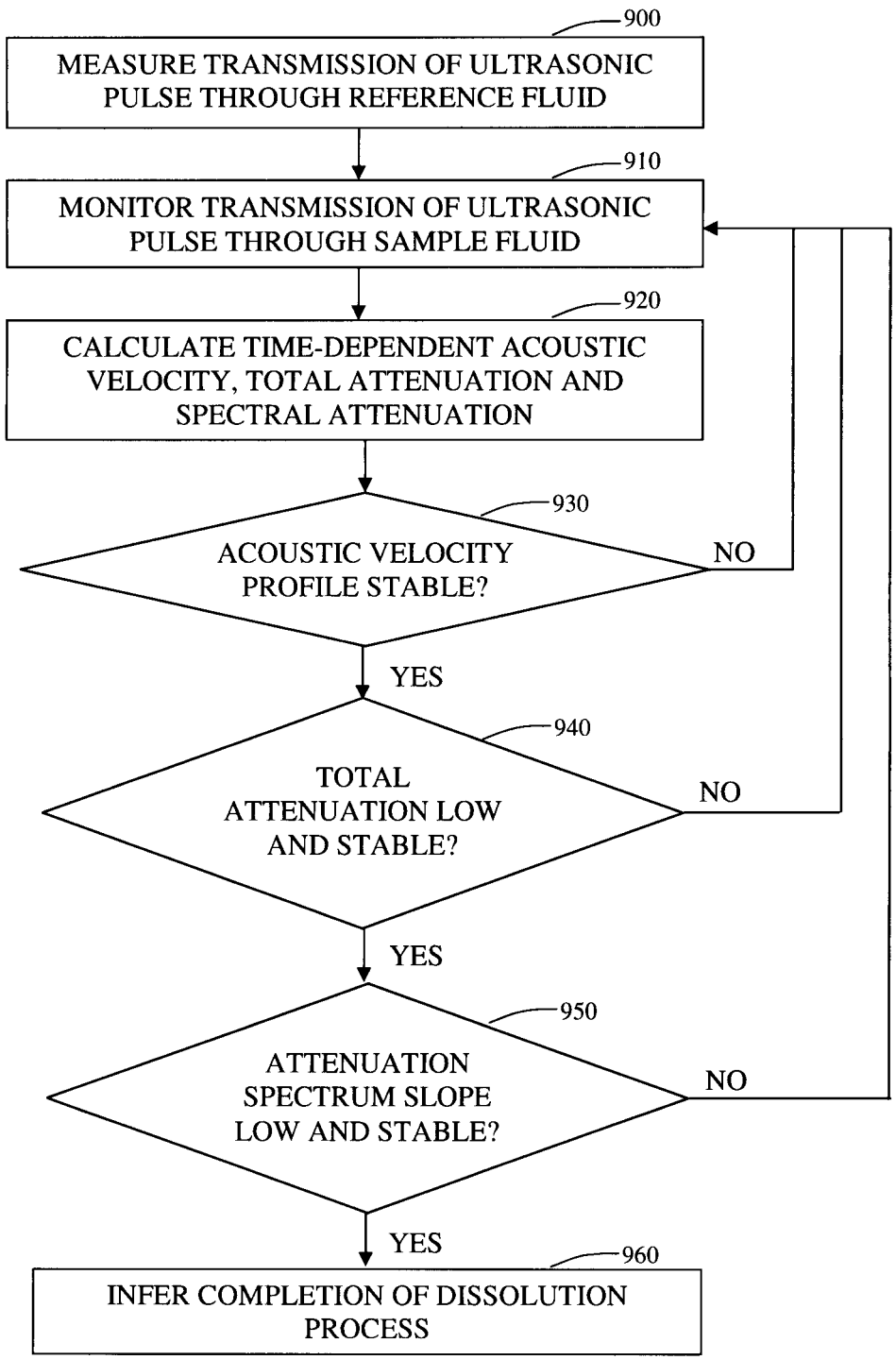
FIG. 49 provides a flow chart illustrating a method of determining the completion of a dissolution process.

Accordingly, a preferred embodiment of the invention is provided in the flow chart illustrated in FIG. 49. In step 900, the transmission of an ultrasonic pulse through a reference medium (preferably free of particles) is measured. Subsequently, in step 910, the transmission of an ultrasound pulse through a sample medium, in which a dissolution process is taking place, is monitored. The time-dependent acoustic velocity, total attenuation, and spectral attenuation profiles are obtained in step 920. Total attenuation may be obtained by summing all components of the attenuation spectrum. It is to be understood that while steps 930-950 are shown as being sequential, their order need to be as shown in FIG. 49.

The time-dependent acoustic velocity is subsequently assessed in step 930 to determine if its profile is substantially free of time-dependent changes. A non-limiting example of a criterion for determining that a substantially stable shape has been achieved is that a linear fit over a local time interval provides a slope of approximately zero. If sufficient stability in the time dependent profile has not been achieved, then a determination is made that the dissolution process has not yet been completed and step 910 is repeated.

The time-dependent total attenuation and spectral attenuation are then assessed in steps 940 and 950. In step 940, the total attenuation profile is assessed to determine whether or not the total attenuation has achieved a profile substantially free of time-dependent changes (for example, a linear fit over a local time interval provides a slope of approximately zero) and the attenuation is approaching a value that is approximately equal to a reference value (for example, the attenuation measured in a calibration step with a reference liquid having achieved complete dissolution). Similarly, in step 950, the attenuation spectrum is assessed to determine whether or not the time-dependent attenuation slope at two or more frequencies has reached a profile substantially free of time-dependent changes (for example, a linear fit over a local time interval provides a slope of approximately zero) and the spectral attenuation is approaching a value that is approximately equal to a reference value (for example, the spectral attenuation measured in a calibration step with a reference liquid having achieved complete dissolution). Provided that both of these conditions are met, and preferably also provided that the acoustic velocity profile has become stable, an inference is made that the dissolution process has completed.

In a preferred embodiment, the method is employed to provide feedback to the dissolution process. For example, the determination of the completion of the dissolution process may be used to arrest a mixing or thermal device used to control temperature of the process. Alternatively, if the process time is extending beyond a specified threshold, feedback may be provided to process equipment to increase the rate of dissolution. In yet another preferred embodiment, the particle size may be monitored, for example, according to previously disclosed embodiments of the invention. In a preferred embodiment, the dissolution process may further be confirmed to have achieved completion after a mean particle size has decreased below pre-determined particle size threshold.

Although the aforementioned embodiments of the invention have been described in the context of a liquid, the embodiments of the invention as recited above may be used for the monitoring of particles in additional types of media, included gases. In a preferred embodiment, the size distribution of particles within a gas is determined and/or monitored using ultrasound frequencies in the range of approximately 1 MHz. In another embodiment, the medium is a solid and the ultrasonic waves are transmitted primarily as longitudinal waves.

In embodiments of the invention involving the measurement and/or calculation of attenuation, total attenuation, and/or an attenuation spectrum, those skilled in the art will appreciate that such measurements and/or calculations may be substituted with transmission, total transmission, and/or a transmission spectrum.

The embodiments of the invention as disclosed above have been provided within the non-limiting context of particle size determination, precipitation and dissolution monitoring, and crystallization monitoring. It is to be understood that the embodiments of the present invention may be applied to a wide range of applications, including the non-limiting examples provided below.

Preferred applications of embodiments of the present invention involving particle analysis in the intermediate wave propagation regime include the following non-limiting list: pharmaceutical applications such as the detection of nucleation, measurement of crystal size distribution, monitoring of crystal growth and wet grinding, mineral processing applications such as separation/sedimentation monitoring, particle size distribution monitoring, critical size determination, and size reduction analysis, food processing applications including the detection of nucleation, measurement of crystal size distribution and monitoring of crystal growth, applications relating to chemical reactor technology such as the detection of particles segregation (for e.g. catalysts) and phase hold-up and concentration measurements in particulate suspensions, and bioprocesses applications such as growth/agglomeration monitoring. Embodiments of the present invention may be used for the monitoring and/or process control for materials such as, but not limited to, hydrosizers, thickeners, emulsions, aerosols, inks and pigments; systems such as, but not limited to, hydraulic transport systems, slurry pipelines, slurry reactors, turbidity measurement systems, and the detection of debris in hydraulic fluids; and processes such, but not limited to, as flocculation, deflocculation, coagulation, sedimentation or settling, segregation, separation, mineral processes, nucleation, suspension formation, aggregation, decantation, filtration/scrubbing, sieving, mixing, dispersion, agglomeration, de-agglomeration, peptization, comminution, heteroagglomeration, heterocoagulation, and heteroflocculation.

Moreover, although the embodiments described above are suitable for online characterization, they may additionally be applied to various offline applications, including the non-limiting example of quality testing and batch to batch variations for powders e.g. silica, glassbeads, alumina etc. Ultrasound is more representative of the particle size as it can make measurements in denser (higher particle count) suspensions as compared to light based techniques.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

SECTION 9

Glossary of Terms and Notation $A_{i-1}$ Initial amplitude (v)
$A_i$ Final amplitude (v)
c Acoustic velocity (m·s$^-$)
$C_{d,f}$ Calculated weighted attenuation (Np·m$^{-1}$)
d Particle diameter (μm)
$E^{\mu,\sigma}$ Total error in predicted attenuation
f Frequency (MHz)
$h_m$ Hankel function
$j_m$ Bessel function
kr Non-dimensional wavenumber (–)
m Integer (–)
N Number of particles (–)
$P_{i-1}$ Initial power
$P_i$ Final power
$\dot{P}_m$ Legendre function
r Particle radius (m)
$w_f$ Weighting factor for attenuation at constituent frequency (–)
x Path length of radiation in slurry (m)
Greek Symbols
α Attenuation (Np·m$^{-1}$)
$\alpha_M$ Measured attenuation (Np·m$^{-1}$)
$\alpha_{wf}^C$ Calculated weighted attenuation at each frequency (Np·m$^{-1}$)
$\alpha_{eff}^C$ Calculated effective attenuation of pulse (Np·m$^{-1}$)
$\alpha_{wf}^M$ Measured weighted attenuation at each frequency (Np·m$^{-1}$)
$\alpha_{eff}^M$ Measured effective attenuation of pulse (Np·m$^{-1}$)
$\alpha_{T,PD}$ Total Attenuation for polydispersed particles (Np·m$^{-1}$)
$\alpha_{T,MD}$ Total Attenuation for mono-dispersed particles (Np·m$^{-1}$)
$\alpha_i$ Attenuation due to $i^{th}$ size fraction (Np·m$^{-1}$)
$\alpha_{sc}$ Scattering attenuation (Np·m$^{-1}$)
$\alpha_t$ Thermal attenuation (Np·m$^{-1}$)
$\alpha_v$ Viscous attenuation (Np·m$^{-1}$)
$\beta_m$ Surface Admittance (–)
Δ Measurement angle
$\Delta_\phi$ Error between known and calculated volume fraction (–)
$\delta_v$ Viscous layer thickness (m)
ϕ Particle volume fraction in suspension (–)
$\phi^C$ Calculated total volume fraction
$\phi_d^{\mu,\sigma}$ Calculated volume fraction in log-normal distribution
κ Compressibility (m$^2$·N$^{-1}$)
λ Wavelength (m$^{-1}$)
μ Geometric mean size (μm)
$\mu_f$ Fluid viscosity (N·s·m$^{-2}$)
σ Geometric standard deviation
$\sigma_{Dist}$ Standard deviation of distribution
ω Angular frequency (rad·s$^{-1}$)
θ Scattering angle
$\rho_p$ Particles density (kg·m$^{-3}$)
$\rho_f$ Fluid density (kg·m$^{-3}$)
$\Sigma_a$ Absorption c/s area (m$^{-2}$)
$\Sigma_s$ Scattering c/s area (m$^{-2}$)
Subscripts
$_f$ Frequency (MHz)
$_i$ Particle size index (i=1 . . . n) or concentration index (i=1 . . . m)

REFERENCES

1. Zwietering T N. Suspension of solid particles in liquid by agitators. *Chemical Engineering Science.* 1958; 8:244-253.
2. Pellam J R, Galt J K. Ultrasonic propagation in liquids. I. Application of pulse technique to velocity and absorption measurements at 15 megacycles. *Journal of Chemical Physics.* 1946; 14:608-613.
3. Pinkerton J M M. A pulse method for measuring ultrasonic absorption in liquids. *Nature.* 1947; 160:128-129.
4. Andrea J, Joyce P. 30 to 230 megacycle pulse technique for ultrasonic absorption measurements in liquids. *British Journal of Applied Physics.* 1962; 13:462-467.
5. Holmes A K, Challis R E, Wedlock D J. A wide bandwidth study of ultrasound velocity and attenuation in suspensions: Comparison of theory and experimental measurements. *Journal of Colloid and Interface Science.* 1993; 156:261-268.
6. Riebel U. Methods of and an apparatus for ultrasonic measuring of the solids concentration and particle size distribution. 1987.
7. McClements D J. Ultrasonic characterization of emulsions and suspensions. *Adv. Colloid Interface Science.* 1991; 37:33-72.
8. Dukhin A S, Goetz P J. Ultrasound for characterizing colloids—particle sizing, zeta potential, rheology. In: Dukhin A S, Goetz P J (Eds.). Studies in interface science (Vol. 15). Boston: Elsevier, 2002

9. Epstein P S, Carhart R R. The absorption of sound in suspensions and emulsions. I. Water fog in air. *Journal of acoustical society of America.* 1941; 25:553
10. Allegra J R, Hawley S A. Attenuation of sound in suspensions and emulsions. *Journal of the Acoustical Society of America.* 1972; 51:1545-1564.
11. McClements J D, Hemar Y, Herrmann N. Incorporation of thermal overlap effects into multiple scattering theory. *Journal of the Acoustical Society of America.* 1999; 105: 915-918.
12. Waterman P S, Truell R. Multiple scattering of waves. *Journal of Mathematical Physics.* 1961; 2:512-537.
13. Lloyd P, Berry M V. Wave propagation through an assembly of spheres. *Proceedings of the Physical Society.* 1967; 91:678-688.
14. Harker A H, Temple J A G. Velocity and attenuation of ultrasound in suspensions of particles in fluids. *Journal of Physics D: Applied Physics.* 1988; 21:1576-1588.
15. Gibson R L, Toksoz M N. Viscous attenuation of acoustic waves in suspensions. *Journal of the Acoustical Society of America.* 1989; 85:1925-1934.
16. Temkin S. Viscous attenuation of sound in dilute suspensions of rigid particles. *Journal of the Acoustical Society of America.* 1996; 100:825-831.
17. Bohren C, Huffman D. Absorption and scattering of light by small particles. J. Wiley & Sons, 1983.
18. Morse P M, Ingard K U. Theoretical acoustics. New york: McGraw Hill 1968.
19. Stolojanu V, Prakash A. Characterization of slurry systems by ultrasonic techniques. *Chemical Engineering Journal.* 2001; 84:215-222.
20. Atkinson C M, Kyotomaa H K. Acoustic wave speed and attenuation in suspensions. *International Journal of Multiphase Flow.* 1992; 18:577-592.
21. Spelt P D M, Norato M A, Sangani A S, Tavlarides L L. Determination of particle size distributions from acoustic wave propagation measurements. *Physics of Fluids.* 1999; 11:1065-1080.
22. Shukla A. Size and concentration measurement in slurries by ultrasonic methods. M.E.Sc. Thesis Thesis. University of Western Ontario, London, 2003.
23. Hojjati H, Rohani S. Measurement and prediction of solubility of paracetamol in water-isopropanol solution. Part 1. Measurement and data analysis. *Organic Process Research & Development.* 2006; 10:1101-1109.
24. Wood A B. A textbook of sound. London: Bell and Sons, 1941.
25. Ament W S. Sound propagation in gross mixtures. *Journal of Acoustical Society of America.* 1953; 25:638-641.
26. Alizadeh-Khaivi S. Ultrasonic measurement techniques in slurries. M.E.Sc Thesis. University of Western Ontario, 2002.
27. Shukla A, Prakash A. Ultrasonic technique to determine particle size and concentration in slurry systems. *Chemical Engineering Science.* 2006; 61:2468-2475.

Therefore what is claimed is:

1. A method of determining a particle size distribution of particles within a sample medium, comprising the steps of:
providing an ultrasonic transmitter and receiver separated by a fixed path length for transmitting and receiving ultrasonic waves;
employing the ultrasonic transmitter and receiver to measure an ultrasonic attenuation spectrum of said sample medium;
calculating, with a computer processor, a simulated attenuation spectrum obtained from a model comprising the calculation of a scattering cross-section, wherein said scattering cross-section accounts for ultrasonic waves scattered into said receiver;
employing the computer processor to vary parameters of said model to minimize an error between said simulated attenuation spectrum and said measured attenuation spectrum, thereby obtaining optimized parameters; and
calculating, with the computer processor, said particle size distribution from said optimized parameters.

2. The method according to claim 1 wherein said measured attenuation spectrum is obtained by:
measuring a frequency spectrum of ultrasonic transmission through a reference medium substantially free of particles,
measuring a frequency spectrum of ultrasonic transmission through said sample medium; and
calculating, with the computer processor, a ratio of said frequency spectrum of said sample medium and said frequency spectrum of said reference medium.

3. The method according to claim 1 wherein a frequency spectrum of said ultrasonic waves and a size of said particles corresponds to an intermediate wave propagation regime.

4. The method according to claim 1 wherein a volume concentration of said particles in said medium exceeds 2%.

5. The method according to claim 1 wherein said sample medium is optically opaque.

6. The method according to claim 1 further comprising the step of measuring one or more physical properties related to said sample medium for input into said model, wherein said one or more physical properties are measured prior to said step of calculating said simulated attenuation spectrum.

7. The method according to claim 1 further comprising the step of calculating, with the computer processor, a frequency-dependent weight factor, said weight factor obtained by determining, at each frequency interval within said measured attenuation spectrum, a value related to a ratio of a transmitted ultrasonic power within said frequency interval to the total transmitted ultrasonic power, and wherein said measured attenuation spectrum and said calculated attenuation spectrum are multiplied by said weight factor prior to said step of varying parameters of said model to minimize an error between said simulated attenuation spectrum and said measured attenuation spectrum.

8. The method according to claim 7, wherein said value is said ratio of the transmitted ultrasonic power within said frequency interval to the total transmitted ultrasonic power.

9. The method according to claim 7 wherein said value is set to zero if it is less than a pre-defined threshold.

10. The method according to claim 1 wherein said transmitter and receiver are inserted into said sample medium at an angle relative to a vertical for preventing accumulation of particles on one or more of said transmitter and receiver.

11. The method according to claim 1 wherein said step of calculating a simulated attenuation spectrum obtained from a model comprising the calculation of a scattering cross-section comprises assuming a functional form of said particle distribution, and wherein said functional form comprises said parameters of said model.

12. The method according to claim 11 wherein said functional form is a log-normal distribution function and wherein said parameters are a mean particle size and standard deviation.

13. The method according to claim 1 wherein said model is a modified form of the Morse and Ingard model, and wherein said modified form of said model is obtained by accounting for ultrasonic waves scattered into said receiver when calculating said scattering cross-section.

14. The method according to claim 1 wherein said scattering cross-section is calculated by including scattered waves that do not propagate into the receiver.

15. The method according to claim 14 further comprising the step of determining a representative angle over which to exclude scattered waves when calculating said scattering cross-section.

16. The method according to claim 15 wherein said angle is estimated from the size of said receiver and a separation distance between said transmitter and receiver.

17. The method according to claim 15 wherein said angle is obtained by calculating an average angle subtended by a point lying on a circumference of said receiver to maximum and minimum points along an axis separating said transmitter and receiver.

18. The method according to claim 15, wherein prior to calculating said simulated attenuation spectrum, said angle is determined according to steps of:
provided a standard suspension having a known particle size distribution;
measuring an ultrasonic attenuation spectrum of said standard suspension;
providing an initial estimate for said angle;
calculating with the computer processor, a simulated attenuation spectrum of said standard suspension obtained from a model comprising the calculation of a scattering cross-section, wherein said scattering cross-section is obtained by excluding ultrasonic waves scattered within said angle, and wherein said simulated attenuation spectrum is calculated according to said known particle size distribution;
employing the computer processor to vary a value of said angle to minimize an error between said simulated attenuation spectrum of said standard suspension and said measured attenuation spectrum of said standard suspension, thereby obtaining an optimized value for said angle.

19. The method according to claim 1 further comprising repeating said steps over a time duration.

20. The method according to claim 19 comprising monitoring a process involving a change in the particle size distribution of said medium.

21. The method according to claim 20 comprising providing feedback to a process involving a change in the particle size distribution of said medium based on said determined particle size distribution.

22. The method according to claim 21 wherein said feedback comprises a variation in one of temperature, mixing intensity, process time, and a combination thereof.

23. The method according to claim 20 wherein said monitoring is performed online.

24. The method according to claim 19 comprising determining the completion of a process involving a change in the particle size distribution of said medium.

25. The method according to claim 1 wherein said ultrasonic waves are generated by a method selected from the list comprising pulse generation, tone burst generation, and chirp signal generation.

26. The method according to claim 1 further comprising estimating the shape of said particles according to the steps of:
measuring a scattering spectrum related to scattered ultrasound waves in said sample medium at an angle other than that of a transmission direction;
assuming a shape of particles within said sample medium;
calculating, with the computer processor, a simulated scattering spectrum obtained from a shape-dependent model comprising the calculation of a shape-dependent scattering cross-section, wherein said simulated scattering spectrum is calculated according to said particle size distribution obtained from said optimized parameters;
employing the computer processor to vary said assumed shape of said particles to minimize an error between said simulated scattering spectrum and said measured scattering spectrum, thereby obtaining an optimized shape of said particles.

27. The method according to claim 26 wherein said angle other than said transmission direction is a direction corresponding to direct backscattering.

28. The method according to claim 26, wherein said step of varying said assumed shape of said particles to minimize an error between said simulated scattering spectrum and said measured scattering spectrum comprises:
obtaining a measured difference spectrum, said measured difference spectrum obtained from the difference between said measured and simulated scattering spectra, and comparing said measured difference spectrum with a library of difference spectra corresponding to various particle shapes; and
employing said computer processor to estimate the shape as that corresponding to the difference spectrum from said library that provides the least error with respect to said measured difference spectrum.

29. The method according to claim 1 wherein said steps of calculating a simulated attenuation spectrum obtained from a model and varying parameters of said model comprises the steps of:
assuming a functional form of said particle distribution, and wherein said functional form comprises said parameters of said model;
determining a discrete set of possible values of said parameters;
calculating, with the computer processor, simulated attenuation spectra from said model using said set of possible values of said parameters; and
employing the computer processor to perform a global search to obtain optimal parameters that minimize an error between said calculated attenuation spectra and said measured attenuation spectrum.

30. A method of determining a particle size distribution of particles within a sample medium, comprising the steps of:
providing an ultrasonic transmitter and receiver separated by a fixed path length for transmitting and receiving ultrasonic waves;
employing the ultrasonic transmitter and receiver to measure an ultrasonic attenuation spectrum of said sample medium;
calculating, with a computer processor, a simulated attenuation spectrum obtained from a model comprising the calculation of a scattering cross-section;
calculating, with the computer processor, a frequency-dependent weight factor, said weight factor obtained by determining, at each frequency interval within said measured attenuation spectrum, a value related to a ratio of a transmitted ultrasonic power within said frequency interval to the total transmitted ultrasonic power;
employing the computer processor to multiple said measured attenuation spectrum and said calculated simulated attenuation spectrum by said weight factor;
employing the computer processor to vary parameters of a model to minimize an error between said multiplied simulated attenuation spectrum and said multiplied measured attenuation spectrum, thereby obtaining optimized parameters; and calculating, with the computer processor, said particle size distribution from said optimized parameters.

31. The method according to claim 30, wherein said value is said ratio of the transmitted ultrasonic power within said frequency interval to the total transmitted ultrasonic power.

32. The method according to claim 30 wherein said value is set to zero if it is less than a pre-defined threshold.

* * * * *